United States Patent
Ackermann et al.

(10) Patent No.: US 7,205,301 B2
(45) Date of Patent: Apr. 17, 2007

(54) MICROBIOCIDAL N-PHENYL-N-[4-(4-PYRIDYL)-2-PYRIMIDIN-2-YL]-AMINE DERIVATIVES

(75) Inventors: Peter Ackermann, Basel (CH); Daniel Stierli, Basel (CH); Pierre Marcel Joseph Jung, Basel (CH); Peter Maienfisch, Basel (CH); Fredrik Emil Malcolm Cederbaum, Basel (CH); Jean-Frederic Wenger, Basel (CH)

(73) Assignee: Syngenta Crop Protection, Inc., Greensboro, NC (US)

(*) Notice: Subject to any disclaimer, the term of this patent is extended or adjusted under 35 U.S.C. 154(b) by 495 days.

(21) Appl. No.: 10/497,974

(22) PCT Filed: Dec. 5, 2002

(86) PCT No.: PCT/IB02/05148

§ 371 (c)(1),
(2), (4) Date: Jun. 3, 2004

(87) PCT Pub. No.: WO03/047347

PCT Pub. Date: Jun. 12, 2003

(65) Prior Publication Data

US 2005/0085496 A1 Apr. 21, 2005

(30) Foreign Application Priority Data

Dec. 7, 2001 (GB) .................... 0129391.9

(51) Int. Cl.
*C07D 401/14* (2006.01)
*A01N 43/56* (2006.01)
*A01N 43/58* (2006.01)

(52) U.S. Cl. ............ 514/252.02; 514/252.03; 514/275; 544/238; 544/331

(58) Field of Classification Search ............... 544/238, 544/331; 514/252.02, 252.03, 275
See application file for complete search history.

(56) References Cited

FOREIGN PATENT DOCUMENTS

| EP | 0431421 | 6/1991 |
|----|---------|--------|
| WO | 9509847 | 4/1995 |
| WO | 0193682 | 12/2001 |
| WO | 02053560 | 7/2002 |

*Primary Examiner*—Deepak Rao
(74) *Attorney, Agent, or Firm*—William A. Teoli, Jr.

(57) ABSTRACT

Fungicidal compounds of Formula (I) wherein m is 0, 1, 2 or 3; n and p are independently of each other 0 or 1; $R_1$ is halogen, optionally substituted alkyl, optionally substituted alkoxy, optionally substituted alkenyloxy, optionally substituted alkynyloxy, optionally substituted thioalkyl optionally substituted aryl, $COOR_{11}$, $CONR_{12}R_{13}$, $S(O)_qR_{14}$, $SO_2NR_{15}R_{16}$ or $NR_{15a}R_{16a}$; q is 1 or 2; and $R_2$, $R_{2a}$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{15a}$, $R_{16a}$, are specified organic groups or a salt thereof; their preparation and compositions containing them

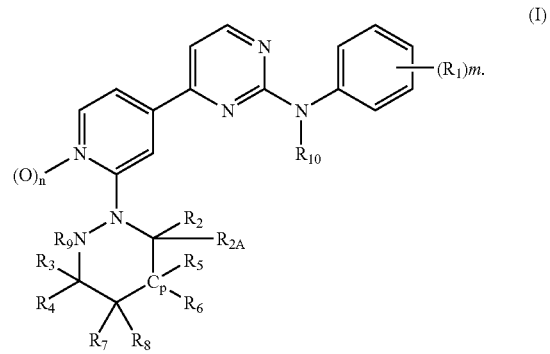

(I)

12 Claims, No Drawings

MICROBIOCIDAL N-PHENYL-N-[4-(4-PYRIDYL)-2-PYRIMIDIN-2-YL]-AMINE DERIVATIVES

This application is a 371 of International Application No. PCT/IB02/05148 filed Dec. 5, 2002, which claims priority to GB 0129391.9, filed Dec. 7, 2001, the contents of which are incorporated herein by reference.

The present invention relates to novel N-phenyl-[4-(4-pyridyl)-pyrimidin-2-yl]-amine derivatives, to a method of protecting plants against attack or infestation by phytopathogenic organisms, such as nematodes or insects or especially microorganisms, preferably fungi, bacteria and viruses, or combinations of two or more of these organisms, by applying a N-phenyl-[4-(4-pyridyl)-pyrimidin-2-yl]-amine derivative as specified hereinafter to a part and/or to the site of a plant, to the use of said derivative for protecting plants against said organisms, and to compositions comprising said derivative as the active component. The invention further relates to the preparation of these novel N-phenyl-[4-(4-pyridyl)-pyrimidin-2-yl]-amine derivatives.

Certain N-phenyl-4-(4-pyridyl)-2-pyrimidineamine derivatives have been described in the art as having pharmacological properties e.g. in the PCT patent applications WO 95/09851 and WO 95/09853, as tumor-inhibiting anticancer substances and in WO 97/19065 and WO98/18782 for the treatment of immune diseases.

Surprisingly, it has now been found that the new N-phenyl-[4-(4-pyridyl)-pyrimidin-2-yl]-amines are effective in plant protection and related areas, showing advantageous properties in the treatment of plant diseases caused by organisms.

The novel N-phenyl-[4-(4-pyridyl)-pyrimidin-2-yl]-amine derivatives according to the invention are those of the formula I

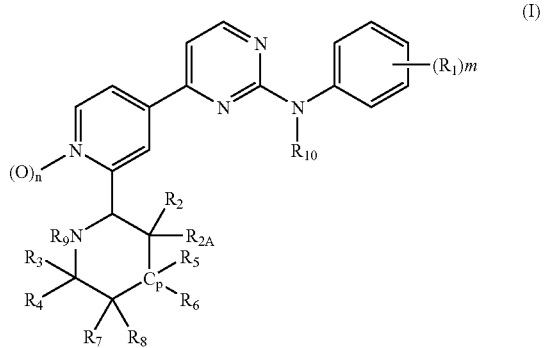

(I)

wherein
m is 0, 1, 2 or 3;
n and p are independently of each other 0 or 1;
$R_1$ is halogen, optionally substituted alkyl, optionally substituted alkoxy, optionally substituted alkenyloxy, optionally substituted alkynyloxy, optionally substituted thioalkyl optionally substituted aryl, $COOR_{11}$, $CONR_{12}R_{13}$, $S(O)_qR_{14}$, $SO_2NR_{15}R_{16}$ or $NR_{15a}R_{16a}$;
when there is more than on $R_1$ group, they may be the same or different;
q is 1 or 2;
$R_2$, $R_{2a}$, $R_3$, $R_4$, $R_5$, $R_6$, $R_7$, $R_8$ are each independently hydrogen, optionally substituted alkyl, $COR_{17}$, $COOR_{18}$ or optionally substituted aryl, and in addition $R_2$ and $R_3$ may also independently be optionally substituted alkoxy, optionally substituted alkenyloxy, optionally substituted alkynyloxy, or optionally substituted alkylthio, $COOR_{19}$, $CONR_{20}OR_{21}$, OH or SH;
$R_6$ and $R_7$ may also be independently halogen, optionally substituted alkoxy, optionally substituted alkenyloxy, optionally substituted alkynyloxy, optionally substituted alkenylamino, optionally substituted alkynylamino, optionally substituted alkylthio, optionally substituted cycloalkyl, optionally substituted heteroaryl, optionally substituted hetrocyclyl, optionally substituted cycloalkyloxy, OH, SH, $N_3$, $NR_{22}R_{23}$ or $N(R_{24})COR_{25}$; or the ring members $CR_3R_4$ or $CR_2R_{2A}$ are independently of each other a carbonyl group (C=O) or a thonyl group (C=S);
or one or two of the adjacent pairs of groups $R_9$ and $R_4$, $R_4$ and $R_5$, $R_5$ and $R_8$, or, if p is zero, $R_{2A}$ and $R_8$ may form a bond, provided that if there are 2 double bonds in the ring the double bonds are not adjacent each other;
or the pair of groups $R_7$ and $R_8$ or the pair of groups $R_6$ and $R_7$ together with the atom to which they are attached form a $C_3-C_7$ saturated ring;
$R_9$ is hydrogen, optionally substituted alkyl, optionally substituted alkenyl or optionally substituted alkynyl;
$R_{10}$ is hydrogen, $C_1-C_4$-alkyl, $C_3-C_4$-alkenyl, $C_3-C_4$-alkynyl, $-CH_2OR_{26}$, $CH_2SR_{27}$, $-C(O)R_{28}$, $-C(O)OR_{29}$, $SO_2R_{30}$, $SOR_{31}$ or $SR_{32}$;
$R_{26}$, $R_{27}$, $R_{28}$, $R_{29}$, $R_{30}$, $R_{31}$, $R_{32}$ are independently $C_1-C_8$-alkyl $C_1-C_8$-alkoxyalkyl, $C_1-C_8$ haloalkyl or phenyl$C_1-C_2$-alkyl wherein the phenyl may be substituted by up to three groups selected from halo or $C_1-C_4$-alkyl,
$R_{11}$, $R_{12}$, $R_{13}$, $R_{14}$, $R_{15}$, $R_{16}$ $R_{15a}$, $R_{16a}$, $R_{17}$, $R_{18}$, $R_{19}$, $R_{20}$, $R_{21}$, $R_{22}$, $R_{23}$, $R_{24}$, and $R_{25}$ are independently H or optionally substituted alkyl; or a salt thereof.

One group of preferred compounds are of those of formula (I') which are compounds of formula I wherein
m is 0, 1, 2 or 3;
n and p are independently of each other 0 or 1;
$R_1$ is halogen, optionally substituted alkyl, optionally substituted alkoxy, optionally substituted thioalkyl optionally substituted aryl, $COOR_{11}$, $CONR_{12}R_{13}$, $S(O)_qR_{14}$, $SO_2NR_{15}R_{16}$ or $NR_{15a}R_{16a}$; when there is more than on $R_1$ group, they may be the same or different;
q is 1 or 2;
$R_2$, $R_{2a}$, $R_3$, $R_4$, $R_5$, $R_6$, $R_7$, $R_8$ are each independently hydrogen, optionally substit alkyl, $COR_{17}$, $COOR_{18}$ or optionally substituted aryl, and in addition $R_2$ and $R_3$ may also independently be optionally substituted alkoxy or optionally substituted alkylthio, $COOR_{19}$, $CONR_{20}R_{21}$, OH or SH;
$R_6$ and $R_7$ may also be independently halogen, optionally substituted alkoxy, optionally substituted alkylthio, OH, SH, $N_3$, $NR_{22}R_{23}$ or $N(R_{24})COR_{25}$; or the ring members $CR_3R_4$ or $CR_2R_{2A}$ are independently of each other a carbonyl group (C=O) or a thiocarbonyl group (C=S);
or one or two of the adjacent pairs of groups $R_9$ and $R_4$, $R_4$ and $R_8$, $R_5$ and $R_8$, or, if p is zero, $R_{2A}$ and $R_8$ may form a bond, provided that if there are 2 double bonds in the ring the double bonds are not adjacent each other;
or the pair of groups $R_7$ and $R_8$ together with the atom to which they are attached form a $C_3-C_7$ saturated ring;
$R_9$ is hydrogen or optionally substituted alkyl;
$R_{10}$ is hydrogen, $C_1-C_4$-alkyl, $C_3-C_4$-alkenyl, $C_3-C_4$-alkynyl, $-CH_2OR_{26}$, $CH_2SR_{27}$, $-C(O)R_{28}$, $-C(O)OR_{29}$, $SO_2R_{30}$, $SOR_{31}$ or $SR_{32}$;
$R_{26}$, $R_{27}$, $R_{29}$, $R_{29}$, $R_{30}$, $R_{31}$, $R_{32}$ are independently $C_1-C_8$-alkyl $C_1-C_8$-alkoxyalkyl, $C_1-C_8$ haloalkyl or phenyl$C_1$–$C_2$-alkyl wherein the phenyl may be substituted by up to three groups selected from halo or $C_1$–$C_4$-alkyl, $R_{11}$, $R_{12}$, $R_{13}$, $R_{14}$, $R_{15}$, $R_{16}$ $R_{15a}$, $R_{16a}$, $R_{17}$, $R_{18}$, $R_{19}$, $R_{20}$, $R_{21}$, $R_{22}$, $R_{23}$, $R_{24}$, and $R_{25}$ are independently H or optionally substituted alkyl; or a salt thereof.

In the context of the present specification alkyl as a group per se and as a structural element of hydroxyalkyl, thioalkyl, alkoxy, alkenyl, alkenyloxy, alkynyl alkynyloxy or haloalkoxy—is preferably $C_1$–$C_6$-alkyl, more preferably lower alkyl, and is linear i.e. methyl, ethyl, propyl, butyl, pentyl or hexyl, or branched, e.g. isopropyl, isobutyl, sec.-butyl, tert.-butyl, isopentyl, neopentyl or isohexyl. Lower alkyl is preferably methyl or ethyl.

Specific examples of alkenyl and alkynyl include allyl, 2-butenyl, 3-butenyl, propargyl, 2-butinyl and 3 butynyl.

When present, the optional substituents on an alkyl, alkenyl or alkynyl moiety include one or more of halogen, nitro, cyano, oxo (and acetals and ketals formed therefrom), $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{3-10}$ alkoxy, $C_{3-10}$ alkoxy($C_{3-10}$)alkoxy, $C_{1-6}$ alkoxy-carbonyl($C_{3-10}$)alkoxy, $C_{3-10}$haloalkoxy, phenyl($C_{1-4}$)alkoxy (where the phenyl group is optionally substituted by one or more of $C_{1-6}$ alkyl, $C_{1-6}$ alkoxy, $C_{1-6}$ haloalkyl, CN, nitro or halogen), $C_{3-7}$ cycloalkyloxy (where the cycloalkyl group is optionally substituted with $C_{1-6}$ alkyl or halogen), $C_{3-10}$ alkenyloxy, $C_{3-10}$ alkynyloxy, SH, $C_{3-10}$ alkylthio, $C_{3-10}$ haloalkylthio, phenyl($C_{1-4}$)alkylthio (where the phenyl group is optionally substituted by one or more of $C_{1-6}$ alkyl, $C_{1-6}$ alkoxy, $C_{1-6}$ haloalkyl, CN, nitro or halogen), $C_{3-7}$ cycloalkylthio (where the cycloalkyl group is optionally substituted with $C_{1-6}$ alkyl or halogen), tri($C_{1-4}$)alkylsilyl($C_{1-6}$)alkylthio, phenylthio (where the phenyl group is optionally substituted by one or more of $C_{1-6}$ alkyl, $C_{1-6}$ alkoxy, $C_{1-6}$ haloalkyl, CN, nitro or halogen), $C_{1-6}$ alkylsulfonyl, $C_{1-6}$ haloalkylsulfonyl, $C_{1-6}$ alkylsulfinyl, $CO_{1-6}$haloalkylsulfinyl, phenylsulfonyl (where the phenyl group is optionally substituted by one or more of $C_{1-6}$ alkyl, $C_{1-6}$ alkoxy, $C_{1-6}$ haloalkyl, CN, nitro or halogen), tri($C_{1-4}$)alkylsilyl, phenyldi($C_{1-4}$)alkylsilyl, ($C_{1-4}$)alkyldiarylsilyl, triphenylsilyl, $C_{3-10}$ alkylcarbonyl, $HO_2C$, $C_{3-10}$ alkoxycarbonyl, aminocarbonyl, $C_{1-6}$ alkylaminocarbonyl, di($C_{1-6}$ alkyl)-aminocarbonyl, N-($C_{1-3}$ alkyl)-N-($C_{1-3}$ alkoxy)aminocarbonyl, $C_{1-6}$ alkylcarbonyloxy, phenylcarbonyloxy (where the phenyl group is optionally substituted by one or more of $C_{1-6}$ alkyl, $C_{1-6}$ alkoxy, $C_{1-6}$ haloalkyl, CN, nitro or halogen), di($C_{1-6}$)alkylaminocarbonyloxy, phenyl (itself optionally substituted by one or more of $C_{1-6}$ alkyl, $C_{1-6}$ alkoxy, $C_{1-6}$ haloalkyl, CN, nitro or halogen), naphthyl (itself optionally substituted by $C_{1-6}$ alkyl or halogen), heteroaryl (itself optionally substituted by $C_{1-6}$ alkyl or halogen), heterocyclyl (itself optionally substituted with $C_{1-6}$ alkyl or halogen), phenyloxy (where the phenyl group is optionally substituted by substituted by one or more of $C_{1-6}$ alkyl, $C_{1-6}$ alkoxy, $C_{1-6}$ haloalkyl, CN, nitro or halogen), naphthyloxy (where the naphthyl group is optionally substituted by $C_{1-6}$ alkyl or halogen), heteroaryloxy, (where the heteroaryl group is optionally substituted by $C_{1-6}$ alkyl or halogen), heterocyclyloxy (where the heterocyclyl group is optionally substituted with $C_{1-6}$ alkyl or halogen), amino, $C_{1-6}$ alkylamino, di($C_{1-6}$) alkylamino, $C_{1-6}$ alkylcarbonylamino and N-($C_{1-6}$)alkylcarbonyl-N-($C_{1-6}$)alkylamino.

Preferred substituents on an alkyl, alkenyl or alkynyl moiety include one or more of halogen, nitro, cyano, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{3-10}$ alkoxy, $C_{3-10}$ alkoxy($C_{3-10}$)alkoxy, $C_{1-6}$ Lkoxy-carbonyl($C_{3-10}$)alkoxy, $C_{3-10}$ haloalkoxy, phenyl($C_{1-4}$)alkoxy (where the phenyl group is optionally substituted by $C_{1-6}$ alkyl or halogen), $C_{3-7}$ cycloalkyloxy (where the cycloalkyl group is optionally substituted with $C_{1-6}$ alkyl or halogen), $C_{3-10}$alkenyloxy, $C_{3-10}$ alkynyloxy, SH, $C_{3-10}$ alkylthio, $C_{3-10}$haloalkylthio, phenyl($C_{1-4}$)alkylthio (where the phenyl group is optionally substituted by $C_{1-6}$ alkyl or halogen), $C_{3-7}$ cycloalkylthio (where the cycloalkyl group is optionally substituted with $C_{1-6}$ alkyl or halogen), tri($C_{1-4}$)alkylsilyl($C_{1-6}$)alkylthio, phenylthio (where the phenyl group is optionally substituted by $C_{1-6}$ alkyl or halogen), $C_{1-6}$ alkylsulfonyl, $C_{1-6}$ haloalkylsulfonyl, $C_{1-6}$ alkylsulfinyl, $C_{1-6}$ haloalkylsulfinyl, phenylsulfonyl (where the phenyl group is optionally substituted by $C_{1-6}$ alkyl or halogen), tri($C_{1-4}$)alkylsilyl, phenyldi($C_{1-4}$) alkylsilyl, ($C_{1-4}$)alkyldiarylsilyl, triphenylsilyl, $C_{3-10}$ alkylcarbonyl, $HO_2C$, $C_{3-10}$ alkoxycarbonyl, aminocarbonyl, $C_{1-6}$ alkylaminocarbonyl, di($C_{1-6}$ alkyl)-aminocarbonyl, N-($C_{1-3}$ alkyl)-N-($C_{1-3}$ alkoxy)aminocarbonyl, $C_{1-6}$ alkylcarbonyloxy, phenylcarbonyloxy (where the phenyl group is optionally substituted by $C_{1-6}$ alkyl or halogen), di($C_{1-6}$)alkylaminocarbonyloxy, phenyl (itself optionally substituted by $C_{1-6}$ alkyl or halogen), heteroaryl (itself optionally substituted by $C_{1-6}$ alkyl or halogen), heterocyclyl (itself optionally substituted with $C_{1-6}$ alkyl or halogen), phenyloxy (where the phenyl group is optionally substituted by $C_{1-6}$ alkyl or halogen), heteroaryloxy, (where the heteroaryl group is optionally substituted by $C_{1-6}$ alkyl or halogen), heterocyclyloxy (where the heterocyclyl group is optionally substituted with $C_{1-6}$ alkyl or halogen), amino, $C_{1-6}$ alkylamino, di($C_{1-6}$) alkylamino, $C_{1-6}$ alkylcarbonylamino and N-($C_{1-6}$) alkylcarbonyl-N—($C_{1-6}$)alkylamino.

More preferred substituents on an alkyl, alkenyl and alkynyl moiety include one or more of halogen, nitro, cyano, $C_{3-7}$ cycloalkyl (itself optionally substituted with $C_{1-6}$ alkyl or halogen), hydroxy, $C_{3-10}$ alkoxy, $C_{3-10}$ alkoxy($C_{3-10}$) alkoxy, $C_{1-6}$ alkoxy-carbonyl($C_{3-10}$)alkoxy, $C_{3-10}$haloalkoxy, SH, $C_{3-10}$alkylthio, $C_{3-10}$ haloalkylthio, $C_{1-6}$alkylsulfonyl, $C_{1-6}$ haloalkylsulfonyl, $C_{1-6}$ alkylsulfinyl, $C_{1-6}$ haloalkylsulfinyl, phenylsulfonyl (where the phenyl group is optionally substituted by $C_{1-6}$ alkyl or halogen), $HO_2C$, $C_{3-10}$ alkoxycarbonyl, aminocarbonyl, $C_{1-6}$ alkylaminocarbonyl, heteroaryl (itself optionally substituted by $C_{1-6}$ alkyl or halogen), heterocyclyl (itself optionally substituted with $C_{1-6}$ alkyl or halogen), phenyloxy (where the phenyl group is optionally substituted by $C_{1-6}$ alkyl or halogen), amino, $C_{1-6}$alkylamino and di($C_{1-6}$) alkylamino.

Aryl includes naphthyl, anthracyl, fluorenyl and indenyl but is preferably phenyl.

The term heteroaryl refers to an aromatic ring containing up to 10 atoms including one or more heteroatoms (preferably one or two heteroatoms) selected from O, S and N. Examples of such rings include pyridine, pyrimidine, furan, quinoline, quinazoline, pyrazole, thiophene, thiazole, oxazole and isoxazole.

The terms heterocycle and heterocyclyl refer to a non-aromatic ring containing up to 10 atoms including one or more (preferably one or two) heteroatoms selected from O, S and N. Examples of such rings include 1,3-dioxolane, tetrahydrofuran and morpholine.

When present, the optional substituents on heterocyclyl include $C_{1-6}$ alkyl as well as those optional substituents given above for an alkyl moiety.

Cycloalkyl includes cyclopropyl, cyclopentyl and cyclohexyl.

Cycloalkenyl includes cyclopentenyl and cyclohexenyl.

When present, the optional substituents on heteroaryl and aryl rings are selected, independently, from halogen, nitro, cyano, NCS—, $C_{1-6}$ alkyl, $C_{1-6}$ haloalkyl, $C_{1-6}$ alkoxy-$(C_{1-6})$ alkyl, $C_{2-6}$ alkenyl, $C_{2-6}$ haloalkenyl, $C_{2-6}$ alkynyl, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$alkoxy, $C_{1-10}$ alkoxy$(C_{1-10})$alkoxy, tri$(C_{1-4})$alkyl-silyl$(C_{1-6})$alkoxy, $C_{1-6}$ alkoxycarbonyl$(C_{1-10})$alkoxy, $C_{1-10}$ haloalkoxy, aryl$(C_{1-4})$ alkoxy (where the aryl group is optionally substituted), $C_{3-7}$ cycloalkyloxy (where the cycloalkyl group is optionally substituted with $C_{1-6}$ alkyl or halogen), $C_{1-10}$alkenyloxy, $C_{1-10}$ alkynyloxy, SH, $C_{1-10}$alkylthio, $C_{1-10}$ haloalkylthio, aryl$(C_{1-4})$alkylthio (where the aryl group may be further optionally substituted), $C_{3-7}$ cycloalkylthio (where the cycloalkyl group is optionally substituted with $C_{1-6}$ alkyl or halogen), tri$(C_{1-4})$alkylsilyl$(C_{1-6})$alkylthio, arylthio (where the aryl group is optionally substituted), $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl (where the aryl group is optionally substituted), tri$(C_{1-4})$alkylsilyl, aryldi$(C_{1-4})$alkylsilyl, $(C_{1-4})$ alkyldiarylsilyl, triarylsilyl, $C_{1-10}$alkylcarbonyl, $HO_2C$, $C_{1-10}$alkoxycarbonyl, aminocarbonyl, $C_{1-6}$ alkylaminocarbonyl, di$(C_{1-6}$ alkyl)aminocarbonyl, N-$(C_{1-3}$ alkyl)-N-$(C_{1-3}$ alkoxy)aminocarbonyl, $C_{1-6}$ alkylcarbonyloxy, arylcarbonyloxy (where the aryl group is optionally substituted), di$(C_{1-6})$alkylamino-carbonyloxy, aryl (itself optionally substituted), heteroaryl (which itself may be further optionally substituted), heterocyclyl (itself optionally substituted with $C_{1-6}$ alkyl or halogen), aryloxy (where the aryl group is optionally substituted), heteroaryloxy (where the heteroaryl group is optionally substituted), heterocyclyloxy (where the heterocyclyl group is optionally substituted with $C_{1-6}$ alkyl or halogen), amino, $C_{1-6}$ alkylamino, di$(C_{1-6})$alkylamino, $C_{1-6}$ alkylcarbonylamino and N-$(C_{1-6})$alkylcarbonyl-N-$(C_{1-6})$alkylamino.

For substituted phenyl and heteroaryl moieties it is preferred that one or more substituents are independently selected from halogen, $C_{1-6}$ alkyl, $C_{1-6}$ haloalkyl, $C_{1-6}$ alkoxy$(C_{1-6})$alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{2-6}$ alkenyl, $C_{2-6}$ haloalkenyl, $C_{2-6}$ alkynyl, $C_{3-7}$ cycloalkyl, nitro, cyano, $CO_2H$, $C_{1-6}$ alkylcarbonyl, $C_{1-6}$ alkoxycarbonyl, $R_{33}R_{34}N$ or $R_{35}R_{36}NC(O)$; wherein $R_{33}$, $R_{34}$, $R_{35}$ and $R_{36}$ are, independently, hydrogen or $C_{1-6}$ alkyl.

In the context of the specification the term halogen is fluorine, bromine, iodine or preferably chlorine; similarly haloalkyl is preferably $C_1$–$C_6$-alkyl, more preferably lower alkyl, that is linear or branched and is substituted by one or more, for example in the case of halo-ethyl up to five, halogen atoms, especially fluorine (an example is trifluoromethyl.

Haloalkoxy is preferably $C_1$–$C_6$-alkoxy, more preferably lower alkoxy, that is linear or branched and that is substituted by one or more, for example in the case of haloethyl up to five, halogen atoms, especially fluorine; trifluoromethoxy and 1,1,2,2-tetrafluoroethoxy are especially preferred.

The moiety attached to the 2-position of the pyridine ring in the compounds of the invention, namely the moiety

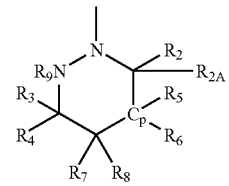

includes 5- and 6-membered ring systems, which are common in the art of heterocycles. Thus examples of the moieties include 2,4-dihydro-pyrazol-3-ones, 2,4-dihydro-pyrazole-3-thione, 1H-pyrazoles, 2H-pyridazin-3-ones, 4,5-dihydro-2H-pyridazin-3-ones, 1,2-dihydro-pyrazol-3-ones, 1,2-dihydro-pyrazole-3-thione, pyrazolidin-3-one, pyrazolidine-3-thione, 2H-pyridazin-3-thione and 4,5-dihydro-2H-pyridazin-3-thione.

More preferred ring systems for the moiety positioned at the 2-position of the pyridyl ring are those selected from the group comprising, 1H-pyrazoles, 2,4-dihydro-pyrazol-3-ones, 1,2-dihydro-pyrazol-3-ones, 4,5-dihydro-2H-pyridazin-3-ones.

The compounds of formula I can form acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid, oxalic acid or amino acids, such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxy-ethane-sulfonic acid, or aromatic sulfonic acids, for example benzene-, p-toluene- or naphthalene-2-sulfonic acid.

The pyridine-N-oxides of formula I can form acid addition salts with strong acids, such as hydrochloric acid, nitric acid, phosphoric acid or sulfonic acids, such as benzenesulfonic acid.

Formula I according to the invention shall include all the possible isomeric forms, as well as mixtures, e.g. racemic mixtures, and any mixtures of rotamers.

In view of the close relationship between the compounds of formula I in free form and in the form of their salts, including also salts that can be used as intermediates, for example in the purification of the compounds of formula I or in order to identify those compounds, herein-before and hereinafter any reference to the (free) compounds is to be understood as including also the corresponding salts, where appropriate and expedient.

Among the compounds of formula I according to the present invention the following groups of compounds are preferred. These groups are in any combination those wherein n is 0;

p is 0 or 1;

m is 1, 2 or 3 or m is 1 and $R_1$ is preferably at the 3- or 4-position of the phenyl ring, preferably at the 3-position.

$R_1$ is selected from the group comprising halogen, $C_{1-3}$ haloalkoxy, CH(OH)R, COR, $SO_2NRR'$, CH(NR'R")R, COORa or CONRbRc where Ra, Rb, Rc, R, R', R" are independently H or lower alkyl or $R_1$ is selected from the group comprising chlorine, fluorine, trifluoromethyl, trifluoromethoxy, or 1,1,2,2-tetrafluoroethoxy, or $R_1$ is 3-chloro;

$R_2$ is selected from the group comprising hydrogen, methyl, ethyl, methoxy, methoxymethyl, ethoxymethyl, or $R_2$ is selected from the group comprising hydrogen, methyl or methoxy or $R_2$ is methyl or the ring members $CR_2R_{2A}$ are a carbonyl group (C=O) or a thiocarbonyl group (C=S);

$R_{2A}$ is selected from the group comprising hydrogen, methyl, ethyl, methoxymethyl, ethoxymethyl, or $R_{2A}$ is hydrogen, methyl, or $R_{2A}$ forms a bond together with $R_8$;

$R_3$ and $R_4$ are independently selected from the group comprising hydrogen, methyl, ethyl, hydroxy, trifluoromethyl, methoxy, methoxymethyl, ethoxymethyl, or $R_3$ and $R_4$ are independently selected from the group comprising hydrogen methyl or methoxy or $R_3$ and $R_4$ are independently hydrogen or methyl or the ring members $CR_3R_4$ are a carbonyl group (C=O) or a thiocarbonyl group (C=S); or $R_4$ together with either $R_9$ or $R_8$ forms a bond;

$R_5$, $R_6$, $R_7$, $R_8$ are each independently hydrogen, methyl, trifluoromethyl, $R_6$ and $R_7$ may also be independently chloro, methoxy, ethoxy, diethylamine $R_7$ may also be formyl or the groups $R_7$ and $R_8$ together with the carbon atom to which they are attached form a cyclopropyl ring or $R_5$ together with $R_8$ form a bond or $R_5$, $R_6$, $R_7$, $R_8$ are each independently hydrogen, methyl;

$R_9$ is hydrogen or methyl;

$R_{10}$ is hydrogen, methyl, ethyl, allyl, propargyl, methoxymethyl, thiomethoxymethyl or ethoxymethyl, or $R_{10}$ is hydrogen or methoxymethyl.

In a further group of preferred compounds $R_2$, $R_{2A}$, $R_3$, $R_4$, $R_5$, $R_6$, $R_7$, $R_8$ and $R_9$ independently of each other are hydrogen or methyl;

In a further group of preferred compounds $R_7$ is hydrogen, methyl, ethyl, allyl, propargyl, methoxymethyl, thiomethoxymethyl or ethoxymethyl, more preferably hydrogen or methoxymethyl.

Preferred individual compounds of the formula I are:

(3-Chloro-phenyl)-{4-[2-(3,4,5-trimethyl-pyrazol-1-yl)-pyridin-4-yl]-pyrimidin-2-yl}-amine;

(3-Chloro-phenyl)-{4-[2-(5-methoxy-3-methoxymethyl-pyrazol-1-yl)-pyridin-4-yl]-pyrimidin-2-yl}-amine;

(3-Chloro-phenyl)-{4-[2-(5-methoxy-3-methoxymethyl-4-methyl-pyrazol-1-yl)-pyridin-4-yl]-pyrimidin-2-yl}-amine;

(3-Chloro-phenyl)-{4-[2-(5-methoxy-4-methyl-pyrazol-1-yl)-pyridin-4-yl]-pyrimidin-2-yl}-amine; (3-Chloro-phenyl)-{4-[2-(5-ethoxy-3,4-dimethyl-pyrazol-1-yl)-pyridin-4-yl]-pyrimidin-2-yl}-amine;

2-{4-[2-(3-Chloro-phenylamino)-pyrimidin-4-yl]-pyridin-2-yl}-5-methoxymethyl-1,4-dimethyl-1,2-dihydro-pyrazol-3-one;

2-(4-{2-[(3-Chloro-phenyl)-methoxymethyl-amino]-pyrimidin-4-yl}-pyridin-2-yl)-1,5-dimethyl-1,2-dihydro-pyrazol-3-one;

2-{4-[2-(3-Chloro-phenylamino)-pyridin-4-yl]-pyridin-2-yl}-1-ethyl-4,5-dimethyl-1,2-dihydro-pyrazol-3-one;

2-{4-[2-(3-Chloro-phenylamino)-pyridin-4-yl]-pyridin-2-yl}-1,4-dimethyl-1,2-dihydro-pyrazol-3-one;

2-{4-[2-(3-Chloro-phenylamino)-pyrimidin-4-yl]-pyridin-2-yl}-1,5-dimethyl-1,2-dihydro-pyrazol-3-one;

2-{4-[2-(3-Chloro-phenylamino)-pyrimidin-4-yl]-pyridin-2-yl}-5-methoxymethyl-4,4-dimethyl-2,4-dihydro-pyrazol-3-one;

2-{4-[2-(3-Chloro-phenylamino)-pyrimidin-4-yl]-pyridin-2-yl}-4,4-dimethyl-2,4-dihydro-pyrazol-3-one;

2-{4-[2-(3-Chloro-phenylamino)-pyrimidin-4-yl]-pyridin-2-yl}4,4,5-trimethyl-2,4-dihydro-pyrazole-3-thione;

5-{4-[2-(3-Chloro-phenylamino)-pyrimidin-4-yl]-pyridin-2-yl}-7-methyl-5,6-diaza-spiro[2.4]hept-6-en-4-one;

2-{4-[2-(3-Chloro-phenylamino)-pyrimidin-4-yl]-pyridin-2-yl}-4-ethyl-4,5-dimethyl-2,4-dihydro-pyrazol-3-one;

(3-Chloro-phenyl)-{4-[2-(5-methoxy-3-methyl-pyrazol-1-yl)-pyridin-4-yl]-pyrimidin-2-yl}-amine;

2{-4-[2-(3-Chloro-phenylamino)-pyrimidin-4-yl]-pyridin-2-yl}-1,4,5-trimethyl-1,2-dihydro-pyrazol-3-one;

2-{4-(3-Chloro-phenylamino)-pyridin-4-yl-pyridin-2-yl}-4,4,5-trimethyl-2,4-dihydro-pyrazol-3-one;

2-{4-[2-(3-Chloro-phenylamino)-pyrimidin-4-yl]-pyridin-2-yl}-1,5-dimethyl-1,2-dihydro-pyrazol-3-one;

4,5-Dichloro-2-{4-[2-(3-chloro-phenylamino)-pyridin-4-yl]-pyridin-2-yl}-2H-pyridazin-3-one;

2-{4-[2-(3-Chloro-phenylamino)-pyrimidin-4-yl]-pyridin-2-yl}-6-methyl-2H-pyridazin-3-one;

2-{4-[2-(3-Chloro-phenylamino)-pyrimidin-4-yl]-pyridin-2-yl}-6-methyl-4,5-dihydro-2H-pyridazin-3-one;

2-{4-[2-(3-Chloro-phenylamino)-pyrimidin-4-yl]-pyridin-2-yl}-6-Phenyl-4,5-dihydro-2H-pyridazin-3-one;

4-Chloro-2-{4-[2-(3-chloro-phenylamino)-pyrimidin-4-yl]-pyridin-2-yl}-5-ethoxy-2H-pyridan-3-one;

4-Chloro-2-{4-[2-(3-chloro-phenylamino)-pyrimidin-4-yl]-pyridin-2-yl}-5-ethylsulfanyl-2H-pyridazin-3-one;

5-Azido-4-chloro-2-{4-[2-(3-chloro-phenylamino)-pyridin-4-yl]-pyridin-2-yl}-2H-pyridazin-3-one;

1-{4-[2-(3-Chloro-phenylamino)-pyrimidin-4-yl]-pyridin-2-yl}-2-methyl-pyrazolidin-3-one;

(3-Chloro-phenyl)-{4-[2-(5-methoxy-3,4-dimethyl-pyrazol-1-yl)-pyridin-4-yl]-pyrimidin-2-yl}-amine;

2-{4-[2-(3-Chloro-phenylamino)-pyrimidin-4-yl]-pyridin-2-yl}-5-methoxymethyl-1-methyl-1,2-dihydro-pyrazol-3-one;

2-{4-[2-(3-Chloro-phenylamino)-pyrimidin-4-yl]-pyridin-2-yl}-1,5-dimethyl-3-oxo-2,3-dihydro-1H-pyrazole-4-carbaldehyde;

5-Chloro-2-{4-[2-(3-chloro-phenylamino)-pyrimidin-4-yl]-pyridin-2-yl}-4-(oxetan-3-yloxy)-2H-pyridazin-3-one; and 4-Chloro-2-{4-[2-(3-chloro-phenylamino)-pyrimidin-4-yl]-pyridin-2-yl}-5-(tetrahydro-furan-2-ylmethoxy)-2H-pyridazin-3-one.

The compounds according to the invention may be prepared according to methods per se known in the art (this does mean, however, that, where novel compounds are produced, the respective process of manufacture is also novel). The procedures for the preparation of compounds of formula I may be outlined as follows:

A) reacting a compound of the formula (II)

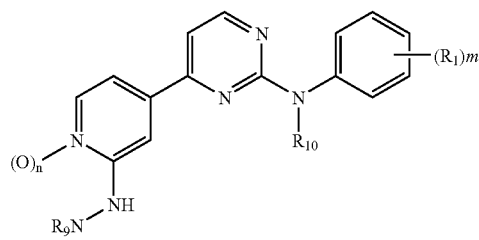

(or a salt thereof) with β-ketoester of the formula III to V under acid catalysed conditions

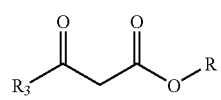

III

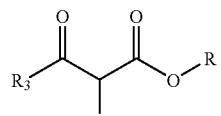

IV

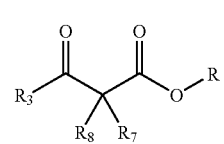

V wherein R is H or optionally substituted alkyl and the other moieties in II to V have the meanings given for a compound of formula I thus obtaining a compound of the sub-formula Ia

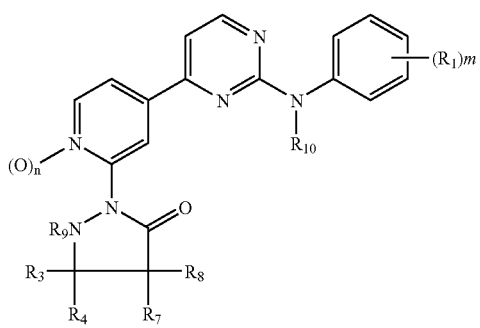

Ia

Compounds of formula II may be prepared by the methods described in WO 01/93682 and illustrated in Synthesis Example 1.

B) reacting a compound of subformula Ia with a thionating reagent such as for example Lawesson reagent to obtain a compound of subformula Ib

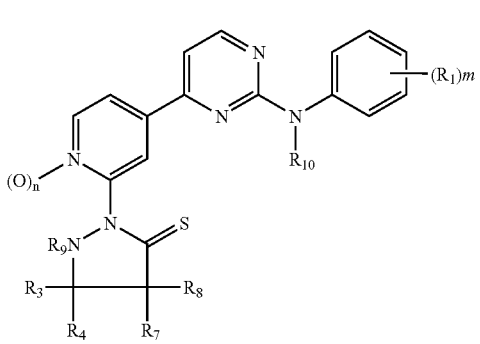

Ib

C) compounds of sub-formula Ia and Ib can be mono- or bis-alkylated to form compounds of structure I wherein p is 0 and all the other moieties have the meanings given for a compound of formula I D) reacting a compound of the formula II (or a salt thereof)

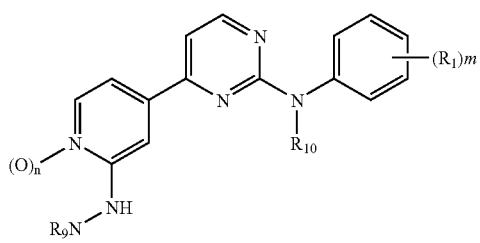

II with a substituted acrylate of formula VI

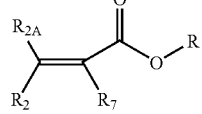

VI or with an alkyl propiolate of formula VII

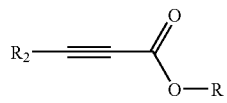

VII thus obtaining a compound of subformula Ic wherein the moieties have the meanings given for a compound of formula I

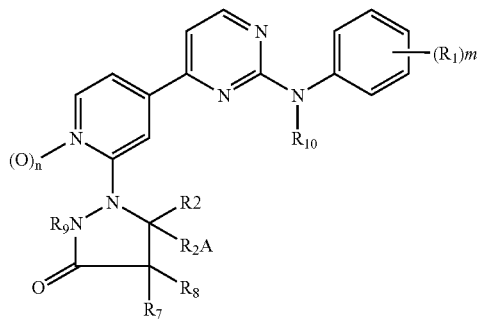

Ic

E) Conversion of the C=O group into the corresponding C=S group in subformula Ic can be achieved by reacting Ic with a thionating reagent such as e.g. Lawesson reagent thus producing compounds of subformula Id

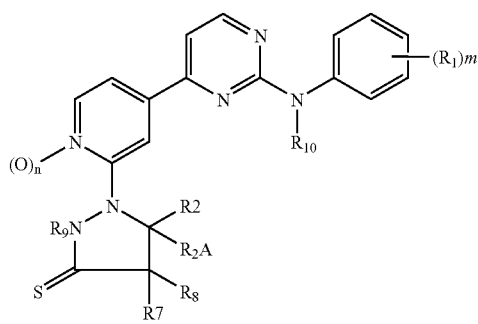

Id

F) compounds of subformula Ic and Id can be alkylated to form compounds of structure I wherein p is 0, R3 is optionally substituted alkoxy or optionally substituted alkylthio and all the other moieties have the meanings given for a compound of formula I G) reacting a compound of the formula II (or a salt thereof)

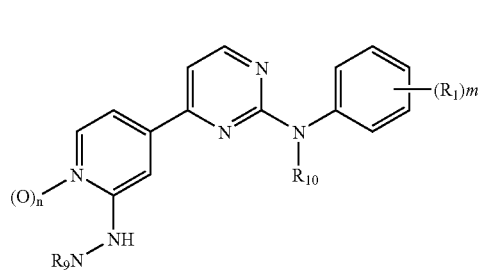

II with a substituted 1,3 dicarbonyl compound of formula VIII

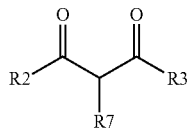

VIII

H) reacting a compound of the formula II (or a salt thereof)

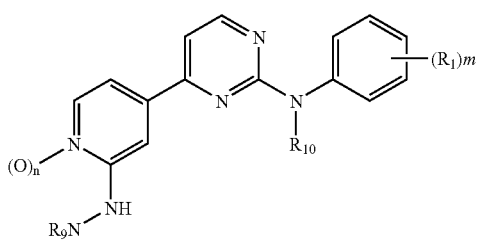

II with a 1,4 dicarbonyl compounds of formula IX or X wherein R is H or optionally substituted alkyl

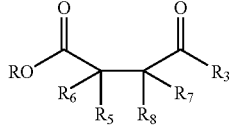

IX

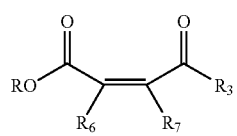

X

I) reacting a compound of the formula I.6 (or a salt thereof)

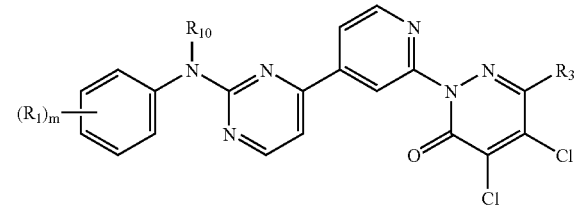

I.6

With a nucleophile to form compounds of formula I

Compounds of forumla I.6 are prepared by the methods of W Davey and D J Tivey, J Chem Soc 1958, p1230 and illustrated in Example 7.

J) reacting a compound of the formula XI (or a salt thereof) with a cyclic hydrazine system of formula XII in the presence of a base and a metal catalyst, such as palladium(II) or palladium(O) complexes commonly used for Buchwald-Hartwig aminations

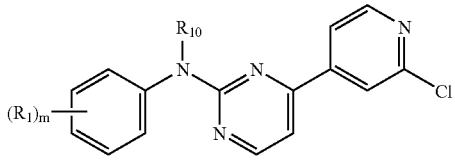

XI

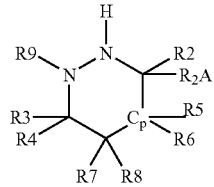

XII

The R group moieties in compounds VIII, IX, X, XI and XII are as for those defined for compounds of formula I.

Compounds of formula III to XII inclusive are known compounds or may be prepared by compounds known processes.

The reaction types A to J and additional methods which can be applied per se or as analogous procedures for the synthesis of compounds of formula I are described for example in:

For 5-membred heterocylces:
J. Bernstein; et al.; J. Am. Chem. Soc. 1947, 69, 1157;
H. Priewe, A. Poljak; Chem. Ber. 1955, 88, 1932;
Patent Application CH 77-10606 19770831 (1982);
EP0680954A2;

For 6 membered heterocycles
Francis, John E.; Doebel, Karl. J.; Schutte, Paula M. Bachmann, Ernst F. Can. J. Chem. 1982, 60, 1214–1232.
Sauter, Fritz; Stanetty, Peter; Blaschke, Alfred; Vyplel, Hermann J. Chem Miniprint, 4, 1981, 1087–1096.
Mikhailovskii, A. Chem. Hetreocycl. Compd. (Engl. Trans.), 1998, 34, 2, 163–166. J. Med. Chem. 1999, 42, 6, 1088–1099. Krutosikova, Alzbeta; Dandarova, Miloslava; Konecny, Vaclav; Collect.Czech.Chem.Commun.; EN; 55; 11; 1990; 2707–2714. Benjamin, Louis E. Earley James V. Gilman Normnan W. J. Heterocyclic. Chem. 1986, 23, 119–124. Patent, Chem. Fabr. Schering, DE 406214. Gregory; Wiggins; J.Chem.Soc.; 1949; 2546, 2549. Lancelot, Jean-Charles; Robba, Max; Chem.Pharm.Bull. 36; 7; 1988; 2381–2385.

Example on Phenylhydrazine: Bourel, Line; Tartar, Andre; Melnyk, Patricia; TELEAY; Tetrahedron Lett.; 37; 24; 1996; 41454148. Sawhney, S. N., Bhutani Sanjay, Vir, Indian J.Chem.Sect.B; 26, 5; 1987, 348–350. P. Coudert, J. Couquelet, P. Tronche J. of Heterocyclic. Chem. 1988, 25, 799.

The chloro atoms of formula I.6 can be substituted by aryl groups under palladium catalysed conditions according to procedures described in: Bert U. W. Maes, Omar 'kyek, Janez Komrlj, Guy L. F. Lemiére, Eddy Esmans, Jef Rozenski, Roger A. Dommisse and Achiel Haemers Tetrahedron, 2001, 57(7), 1323–1330.

β-Ketoesters of formula III–V are known or can be prepared according to procedures described in:
Hyoung R. K. Synlett 1998, 789–791; Freskos J. N. Tetrahedron letters, Vol. 35, No. 6, pp. 835–838 (1994);
J. Chem. Soc., Perkin Trans. 1, (4), 839–61 (1988); Bull. Soc. Chim. Belg., 94(7), 449–56 (1985);
Collins D. J. Aust. J. Chem., 43, 617–22 (1990);

Procedures for the alkylation of compounds of the subformula Ia to Id are described in the experimental section using Williamson conditions.

Conversion of C=O groups (in Ia and Ic) into C=S groups (subformulas Ib and Id) is described in the experimental section using Lawesson reagent under standard conditions or according to procedures given in Ley, Steven V.; Leach, Andrew G.; Storer, R. Ian. J. Chem. Soc., Perkin Trans. 1 (2001), (4), 358–361.

Procedures for the palladium catalysed C—N linkage reaction (Burchwald-Hartwig amination) of compounds of formula XI with cyclic hydrazine ring systems of formula XII are given in the experimental part and are described in PCT/IB01/02821.

EXAMPLES

The subsequent examples are intended to illustrated the invention, without however limiting the scope thereof.

Synthesis Example 1

(3-Chloro-phenyl)-[4-(2-hydrazino-pyridin-4-yl)-pyrimidin-2-yl]-amine

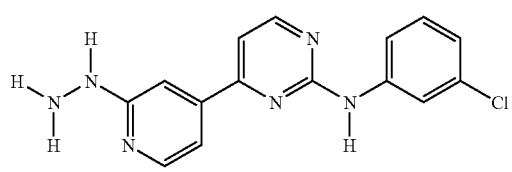

(I)

A mixture of (3-chloro-phenyl)-[4-(2-chloro-pyridin-4-yl)-pyrimidin-2-yl]-amine (4.8 g, 0.015 mol) in hydrazine (20 ml, 0.41 mol) is refluxed for 90 minutes. The reaction is poured into ethanol (300 ml) with efficient stirring. The resulting precipitate is filtered with suction to yield the title compound, m.p. 201–203° C.

Synthesis Example 2

2-{4-[2-(3-Chloro-phenylamino)-pyrimidin-4-yl]-pyridin-2-yl}-5-methyl-2.4-dihydro-pyrazol-3-one

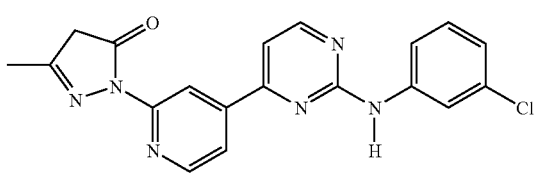

(II)

A mixture of (3-Chloro-phenyl)-[4-(2-hydrazino-pyridin-4-yl)-pyrimidin-2-yl]-amine (3.14 g, 0.010 mol) and Methyl acetoacetate (1.28 g, 0.010 mol) in EtOH (30 ml) and Acetic acid (30 ml) is stirred at reflux for one hour. At room temperature the resulting precipitate is filtered with suction to yield the title compound,(3.50 g, 92%) m.p. 149–150° C.

Synthesis Example 3

A mixture of 2-{4-[2-(3-Chloro-phenylamino)-pyrimidin-4-yl]-pyridin-2-yl}-5-methyl-2,4-dihydro-pyrazol-3-one (3.42 g, 0.009 mol), iodomethane (2.52 g, 0.018 mol) and potassium carbonate anhydrous (3.78 g, 0.027 mol) in DMF (30 ml) is stirred at room temperature for three hours. After stirring the resulting is partitioned between ethyl acetate and water. The organic phase is separated, dried over magnesium sulfate, filtered and evaporated under reduced pressure. The residue is purified twice by silicagel chromatography to give all possible Isomers of the title compounds IIIa to IIIf. IIIa (0.10 g, 2.8%) m.p. 185–188° C.,
IIIb (0.29 g, 8.1%) m.p. 163–166° C.,
IIIc (0.52 g, 14.1%) m.p. 192–194° C.,
IIId (0.53 g, 14.4%) m.p. 89–94° C.,
IIIe (0.29 g, 8.0%) m.p. 149–150° C.,
IIIf (0.11 g, 3.0%) m.p. 149–150° C.,

Synthesis Example IIIa

2-{4-[2-(3-Chloro-phenylamino)-pyrimidin-4-yl]-pyridin-2-yl}-4,5-dimethyl-2,4-dihydro-pyrazol-3-one (IIIa)

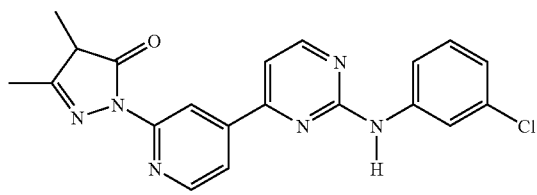

Synthesis Example IIIb

2-{4-[2-(3-Chloro-phenylamino)-pyrimidin-4-yl]-pyridin-2-yl}-4,4,5-trimethyl-2,4-dihydro-pyrazol-3-one (IIIb)

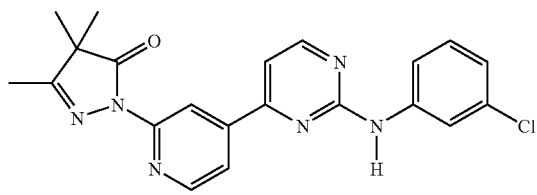

Synthesis Example IIIc

2-{4-[2-(3-Chloro-phenylamino)-pyrimidin-4-yl]-pyridin-2-yl}-1,5-dimethyl-1,2-dihydro-pyrazol-3-one (IIIc)

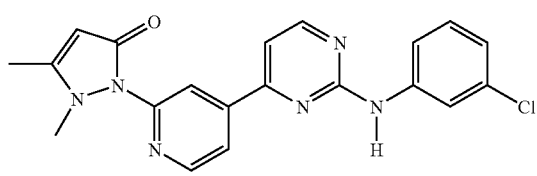

Synthesis Example IIId

2-{4-[2-(3-Chloro-phenylamino)-pyrimidin-4-yl]-pyridin-2-yl}-1,4,5-trimethyl-1,2-dihydro-pyrazol-3-one (IIId)

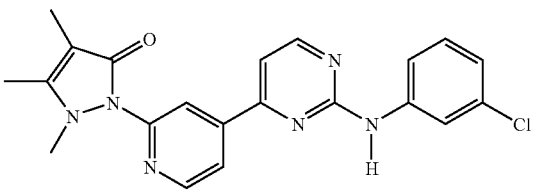

Synthesis Example IIIe (3-Chloro-phenyl)-{4-[2-(5-methoxy-3-methyl-pyrazol-1-yl)-pyridin-4-yl]-pyrimidin-2-yl}-amine (IIIe)

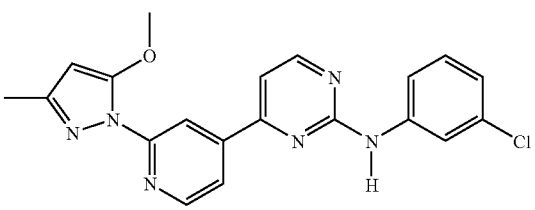

Synthesis Example IIIf (3-Chloro-phenyl)-{4-[2-(5-methoxy-3,4-dimethyl-pyrazol-1-yl)-pyridin-4-yl]-pyrimidin-2-yl}-amine (IIIf)

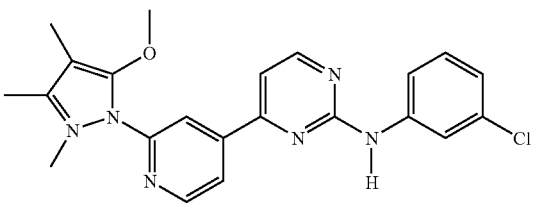

Synthesis Example 4

Synthesis Example IVb

2-{4-[2-(3-Chloro-phenylamino)-pyrimidin-4-yl]-pyridin-2-yl}-4,4,5-trimethyl-2,4-dihydro-pyrazole-3-thione (IVb)

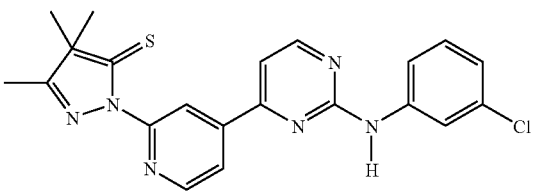

A mixture of 2-{4-[2-(3-Chloro-phenylamino)-pyrimidin-4-yl]-pyridin-2-yl}-4,4,5-trimethyl-2,4-dihydro-pyrazol-3-one (0.21 g, 0.0005 mol) and Lawesson reagent (0.22 g 0.0005 mol) in toluene (3 ml) is stirred at 100° C. for one hour. After cooling the resulting solution is directly purified by silicagel column chromatography to the title compounds (IVb) (0.19 g, 88.1%) m.p. 167–168° C.,

Synthesis Example 5

Synthesis Example V

1-{4-[2-(3-Chloro-phenylamino)-pyrimidin-4-yl]-pyridin-2-yl}-4,5-dihydro-1H-pyrazol-3-ol

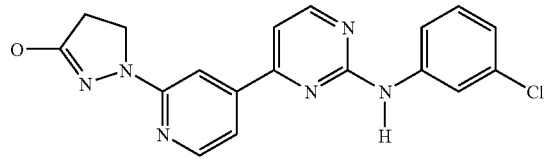

To a mixture of (3-Chloro-phenyl)-[4-(2-hydrazino-pyridin-4-yl)-pyrimidin-2-yl]-amine (7.82 g, 0.025 mol) and Methyl acrylate (2.58 g, 0.030 mol) in tert BuOH (80 ml) is added Potassium tert-butoxyde (5.6 g, 0.05 mol) in portions at 25° C. After stirring for two hours the resulting brown solution is poured in water (500 ml), acidified with acetic acid and partitioned between ethyl acetate and water. The organic phase is separated, dried over magnesium sulfate, filtered and evaporated under reduced pressure. The residue is purified by crystallizing from acetone. The resulting precipitate is filtered with suction to yield the title compound. (1.55 g, 16.9%) m.p. 222–226° C.

Synthesis Example 6

A mixture of 1-{4-[2-(3-Chloro-phenylamino)-pyrimidin-4-yl]-pyridin-2-yl}-4,5-dihydro-1H-pyrazol-3-ol (0.734 g, 0.0020 mol), iodomethane (175 µl, 0.0028 mol) and potassium carbonate anhydrous (0.497 g, 0.0036 mol) in acetonitrile (4 ml) and DMF (2 ml) is stirred at 45° C. for seven hours. After stirring the resulting is partitioned between ethyl acetate and water. The organic phase is separated, dried over magnesium sulfate, filtered and evaporated under reduced pressure. The residue is purified by silicagel chromatography to give both possible Isomers of the title compounds.

VIa (0.192 g, 25.2%) mp. 143–144° C.
VIb (0.036 g, 4.7%) mp. 202–205° C.

Synthesis Example VIa

1-{4-[2-(3-Chloro-phenylamino)-pyrimidin-4-yl]-pyridin-2-yl}-2-methyl-pyrazolidin-3-on

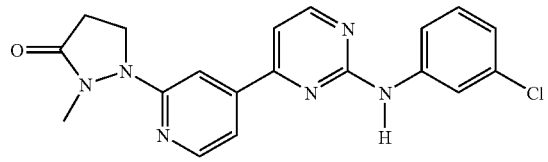

Synthesis Example VIb (3-Chloro-phenyl)-{4-[2-(3-methoxy-4,5-dihydro-pyrazol-1-yl)-pyridin-4-yl]-pyrimidin-2-yl}-amine

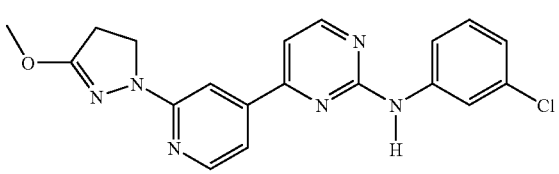

Synthesis Example 7

4,5-Dichloro-2-{4-[2-(3-chloro-phenylamino)-pyrimidin-4-yl]-pyridin-2-yl}-2H-pyridazin-3-one

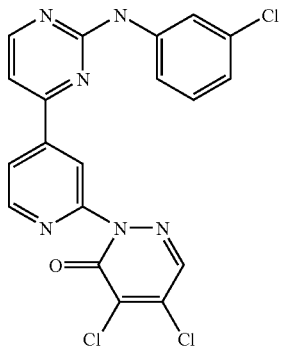

To a suspension of (3-Chloro-phenyl)-[4-(2-hydrazino-pyridin-4-yl)-pyrimidin-2-yl]-amine (5 g) in acetic acid (80 mL) was added 2.8 g of Mucochloric acid. The mixture was heated at 125° C. for 4 h. The solvent was concentrated and the crude was poured into water (500 mL). The suspension was neutralised by addition of solid potassium carbonate until pH 7. The aqueous phase was extracted with ethyl acetate (3×200 mL). The organic phases were combined, dried over MgSO4, and concentrated. Flash silica chromatography, eluting with ethyl acetate-tetrahydrofuran (1-0 to 1-1), afforded the title compound as a solid (3.11 g, 44%). Mp 238–240° C., 1H NMR (DMSO-d6) 10.3 (1H, s, NH), 8.84 (1H, d, 5 Hz), 8.76 (1H, d, 5 Hz), 8.42 (1H, s), 8.38 (1H, s), 8.28 (1H, 2 Hz, 5 Hz), 8.04 (1H, t, 2 Hz), 7.74 (1H, dd), 7.62 (1H, d, 5 Hz), 7.32 (1H, t, 8 Hz), 7.02 (1H, dd, 2 Hz, 8 Hz). 13CNMR DMSO-d6) 160.3, 160.2, 159.9, 155.5, 153.5, 150.2, 146.6, 141.7, 136.7, 136.6, 134.0, 132.9, 130.1, 121.9, 121.1, 118.7, 118.2, 117.3, 109.3.

Synthesis Example 8

2-{4-[2-(3-Chloro-phenylamino)-pyrimidin-4-yl]-pyridin-2-yl}-6-methyl-2H-pyridazin-3-one

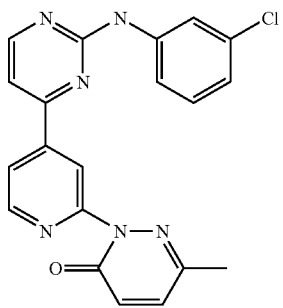

To a suspension of (3-Chloro-phenyl)-[4-(2-hydrazino-pyridin-4-yl)-pyrimidin-2-yl]-amine (2 g) in acetic acid (40 mL) was acetate (3×200 mL).). The organic phase were combined, dried over MgSO4, and concentrated. Flash silica chromatography, eluting with ethyl acetate-tetrahydrofuran (1-0 to 1-1), afforded the title compound as a solid (1.39 g, 55%). Mp 187–189° C., 1H NMR (DMSO-d6) 9.8 (1H, s, NH), 8.86 (1H, d, 5 Hz), 8.80 (1H, d, 5 Hz), 8.35 (1H, s), 8.28 (1H, dd, 2 Hz, 5 Hz), 8.14 (1H, t, 2Hz), 7.73 (1H, m), 7.7.48 (1H, d, 10 Hz), 7.36 (1H, t, 8 Hz), 7.14 (1H, d, 10 Hz), 7.08 (1H, dd, 1 Hz, 7 Hz), 2.39 (3H,s), 13CNMR (DMSO-d6) 160.8, 160.5, 160.3, 159.0, 154.8, 150.5, 146.7, 145.4, 142.2, 135.4, 133.3, 130.8, 130.5, 121.5, 119.2, 118.6, 117.7, 109.6, 20.58.

Synthesis Example 9

2-{4-[2-(3-Chloro-phenylamino)-pyrimidin-4-yl]-pyridin-2-yl}-6-methyl-4,5-dihydro-2H-pyridazin-3-one

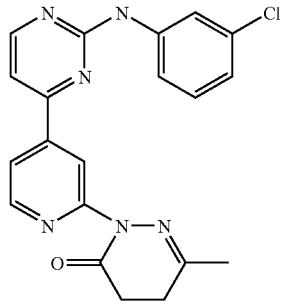

To a suspension of (3-Chloro-phenyl)-[4-(2-hydrazino-pyridin-4-yl)-pyrimidin-2-yl]-amine (2 g) in n-Butanol (40 mL) was added of 0.744 g of levulinic acid. The mixture was heated at reflux. After 3 h, the mixture was cooled at 0° C. and the 4-({4-[2-(3-Chloro-phenylamino)-pyrimidin-4-yl]-pyridin-2-yl}-hydrazono)-4-methyl-butyric acid (1.92 g, 73%) was recovered by filtration. Mp 218–220° C., 1H NMR DMSO-d6) 12.1 (1H, OHacid), 9.93 (1H, s, NH), 9.48 (1H, s, NH), 8.64 (1H, d, 5 Hz), 8.24 (1H, d, 5 Hz), 8.0 (1H, s), 7.76 (2H, m), 7.46 (1H, d, 5 Hz), 7.38 (1H, dd, 2 Hz, 5 Hz), 7.30 (1H, t, 8 Hz), 6.98 (1H, dd, 1 Hz, 8 Hz), 2.51 (4H, s), 1.92 (3H, s), $^{13}$C NMR (DMSO-d6 176.2, 164.6, 161.6, 161.2, 150.5, 150.1, 147.5, 144.0, 134.9, 132.1, 122.97, 120.13, 119.2, 113.7, 111.1, 105.9, 35.33 (CH2), 32.56 (CH2), 18.09 (CH3), MS (ES−) 409 (M−1, 100), 819 (2M−1, 30). The 4-({4-[2-(3-Chloro-Phenylamino)-pyrimnidin-4-yl]-pyridin-2-yl}-hydrazono)-4-methyl-butyric acid (1.5 g) was dissolved in acetic acid (40 mL). The solution was stirred at 110° C. for 3 h then the solution was poured in a mixture of water and ice (250 mL) and neutralised with a solution saturated of sodium hydrogenocarbonate until pH 7. The mixture was extracted with ethyl acetate (3×100 mL). The organic phase were combined, dried over MgSO4, and concentrated. Flash silica chromatography, eluting with ethyl acetate-tetrahydrofuran (3-1), afforded the title compound as a solid (0.7263 g, 51%). Mp 189–192° C., 1H NMR (DMSO-d6) 10.07(1H, NH), 8.73 (1H, d, 5 Hz), 8.69 (1H, d, 5 Hz), 8.16 (1H, s), 8.06 (2H, m), 7.73 (1H, dd, 3 Hz, 10 Hz), 7.60 (1H, d, 5 Hz), 7.31 (1H, t, 8 Hz), 7.03(1H, dd, 3 Hz, 8 Hz), 2.63 (4H, m), 2.07 (3H, s). $^{13}$C NMR (DMSO-d6) 165.3, 160.3, 159.6, 159.3, 154.9, 153.9, 149.0, 141.1, 132.5, 129.7, 120.7, 119.2, 117.8, 117.6, 116.7, 108.66, 26.4, 25.3, 22.0. MS (ES+) 393 (MH+, 100), 785 (2 MH+, 60).

Synthesis Example 10

2-{(4[2-(3-Chloro-phenylamino)-pyrimidin-4-yl]-pyridin-2-yl}-6-Phenyl-4,5-dihydro-2H-pyridazin-3-one

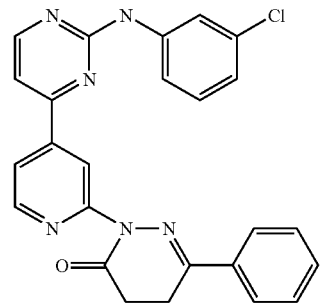

To a suspension of (3-Chloro-phenyl)-[4-(2-hydrazino-pyridin-4-yl)-pyrimidin-2-yl]-amine (2 g) in n-Butanol (40 mL) was added of 1.14 g of 3-benzoylpropionic acid. The mixture was heated at reflux. After 3 h, the mixture was cooled at 0° C. and the 4-({4[2-(3-Chloro-phenylamino)-pyrimidin-4-yl]-pyridin-2-yl}-hydrazono)-4-phenyl-butyric acid (2.19 g, 72%) was recovered by filtration. Mp 144–146° C., 1H NMR (DMSO-d6).12.0 (1H, OH), 10.4 (1H, s, NH), 10.1 (1H, s, NH), 8.77 (1H, d, 5 Hz), 8.42 (1H, d, 5 Hz) 8.12 (1H, s), 8.06 (1H, s), 7.80 (3H, m), 7.6 (1H, d, 5 Hz) 7.53 (1H, d, 5 Hz), 7.45 (3H, m), 7.34 (1H, t, 8 Hz), 7.08 (1H, m) 3.4 (2H, m), 2.95 (2H, m), MS (ES+) 473 (MH+, 100),. MS (ES−) 471 (M−1, 100). To a solution of 4-({4-[2-(3-Chloro-phenylamino)-pyrimidin-4-yl]-pyridin-2-yl}-hydrazono)-4-phenyl-butyric acid (0.48 g) in tetrahydrofuranne (40 mL) was additionned N,N'-dicyclohexylcarbodiimide (0.23 g) and 1-Hydroxybenzotriazole (0.1401 g). The solution was stirred at reflux for 2 h then the solvent was evaporated. The crude was chromatographied, eluting with ethyl acetate to gave the title compound as a solid (0.3366 g, 78%). Mp 165–167° C., 1H NMR (CDCl3) 9.6 (1H,s, NH), 8.76 (1H, d, 5 Hz), 8.59 (1H, d, 5 Hz), 8.21 (1H, s), 7.86 (4H, m), 7.44 (4H, m), 7.26 (2H, m), 7.01 (1H, m), 3.18 (2H, t, 8 Hz), 2.87 (2H, t, 8 Hz). 13C NMR (CDCl3) 166.3, 162.4, 160.4, 159.8, 154.8, 152.9, 150.1, 146.7, 140.9, 135.7, 134.9, 130.5, 130.3, 129.0, 126.7, 122.9, 120.1, 119.6, 118.8, 117.55, 109.6, 28.4, 23.6. MS (ES+) 455 (MH+, 100), 909 (2 MH+, 10).

Synthesis Example 11

4-Chloro-2-{4-[2-(3-chloro-phenylamino)-pyrimidin-4-yl]-pyridin-2-yl}-5-ethoxy-2H-pyridazin-3-one

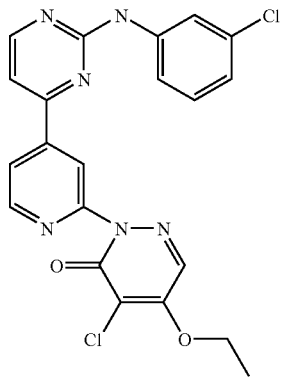

To a suspension of 4,5-Dichloro-2-{4-[2-(3-chloro-phenylamino)-pyrimidin-4-yl]-pyridin-2-yl}-2H-pyridazin-3- one (0.3 g) in ethanol (10 mL) was added of 0.220 mg of potassium carbonate. The mixture was heated to reflux for 4 h. The suspension was poured into water (50 mL) and extracted with ethyl acetate (2×100 mL). The organic phase were combined, dried over MgSO$_4$, and concentrated. Flash silica chromatography, eluting with ethyl acetate-hexane (9:1), afforded the title compound as a solid (0.130 g, 35%). Mp 196–198° C., 1H NMR (CDCl$_3$) 8.80 (1H, d, 3 Hz), 8.60 (1H, d, 6 (1H, s), 8.02 (2H, d, m), 7.93 (1H, s), 7.46 (1H, dd, 6 Hz, 3 Hz), 7.31 (1H,m), 7.29 (1H, d 3 Hz), 7.28 (1H, s), 4.43 (2H, q, 6 Hz), 1.56 (3H, t, 6 Hz).

Synthesis Example 12

4-Chloro-2-{4-[2-(3-chloro-phenylamino)-pyrimidin-4-yl]-pyridin-2-yl}-5-ethylsulfanyl-2H-pyridazin-3-one

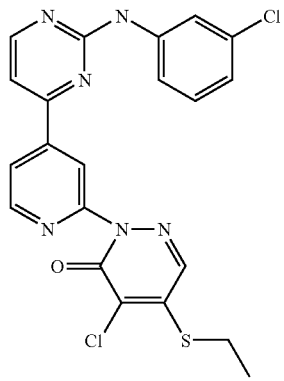

To a suspension of 4,5-Dichloro-2-{4-[2-(3-chloro-phenylamino)-pyrimidin-4-yl]-pyridin-2-yl}-2H-pyridazin-3-one (0.3 g) in acetonitrile (10 mL) was added of 0.15 mL of ethylmercaptan and 0.280 mg of potassium carbonate. The mixture was heated to reflux for 2 h. The suspension was filtered and the solid was washed with ethyl acetate to gave the title compound (0.220 g, 46%). Mp 80–100° C., 1H NMR (DMSO-d6) 8.8 (1H, d, 3 Hz), 859 (1H, d, 6 Hz), 8.37 (1H, s, NH), 7.98 (1H, d, 6 Hz, 3 Hz), 7.92 (1H, t, 3 Hz), 7.86 (1H, s), 7.46 (1H, d, 9 Hz, 3 Hz), 7.40 (1H,s), 7.27(2H, m), 7.04(1H, d, 9 Hz), 3.12 (2H, q, 6 Hz), 1.47 (3H, t, 6 Hz).

Synthesis Example 13

5-Azido-4-chloro-2-{4-[2-(3-chloro-phenylamino)-pyrimidin-4-yl]-pyridin-2-yl}-2H-pyridazin-3-one

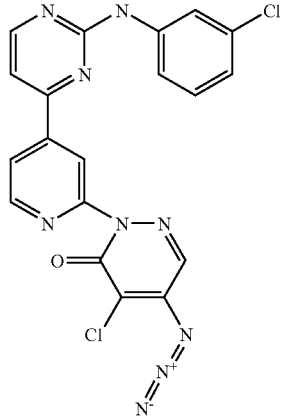

To a suspension of 4,5-Dichloro-2-{4-[2-(3-chloro-phenylamino)-pyrimidin-4-yl]-pyridin-2-yl}-2H-pyridazin-3-one (0.3 g) in acetonitrile (10 mL) was added of 0.09 g of sodium azide. The mixture was heated to reflux for 4 h. The suspension was filtered to give the title compound as a solid (0.280 g, 95%). Mp 184–186° C., 1H NMR (DMSO-d6) 10.1 (1H, s, NH), 8.75 (1H, d, 6 Hz), 8.67 (1H, d, 3 Hz), 8.28 (1H, s), 8.27 (1H, s), 8.18(1H, dd, 1 Hz, 3 Hz), 7.97 (1H, m), 7.65 (1H, dd), 7.57(1H, d, 6 Hz), 7.25 (1H, t, 9 Hz), 6.94 (1H, dd).

Synthesis Example 14

5-Chloro-4-cyclopropylamin-2-{4-[2-(3-chloro-phenylamino)-pyrimidin-4-yl]-pyridin-2-yl}-2H-pyridazin-3-one and 5-Cyclopropylamin-4-chloro-2-{4-[2-(3-chloro-phenylamino)-pyrimidin-4-yl]-pyridin-2-yl)-2H-pyridazin-3-one

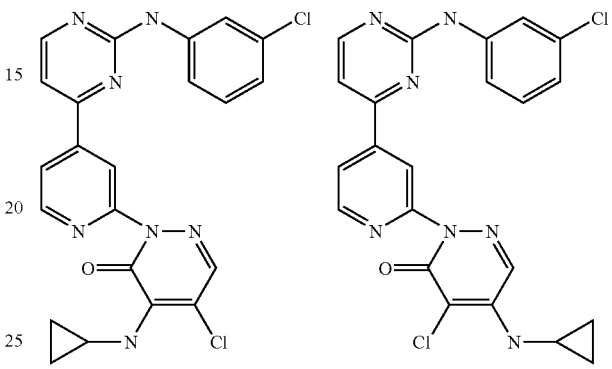

A suspension of 4,5-Dichloro-2-{4-[2-(3-chloro-phenylamino)-pyrimidin-4-yl]-pyridin-2-yl}-2H-pyridazin-3-one (0.3 g) in cyclopropylamine (10 mL) was heated at reflux for 2 h. The solvent was evaporated under vacuum. Flash silica chromatography, eluting with ethyl acetate-hexane (1:1), afforded the 5-Chloro-4-cyclopropylamin-2-{4-[2-(3-chloro-phenylamino)-pyrimidin-4-yl]-pyridin-2-yl}-2H-pyridazin-3-one as a solid (Mp 117–121° C., 0.082 g, 26%) and the 5-cyclopropylamin-4-chloro-2-{4-[2-(3-4-yl]-pyridin-2-yl}-2H-pyridazin-3-one (Mp 90–100° C., 0.180 g, 58%) as a solid.

Synthesis Example 15

5-Chloro-4-butanol-2-(4-[2-(3-chloro-phenylamino)-pyrimidin-4-yl]-pyridin-2-yl}-2H-pyridazin-3-one

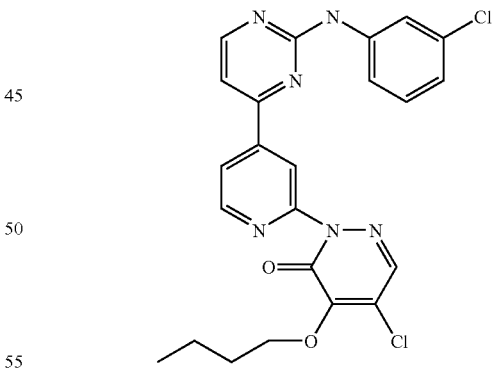

To a solution of butanol (0.18 mL) in tetrahydrofuran (40 mL) was added a solution of Lithium diisopropylamide (1.5 M, 1.3 mL) at room temperature. The solution was stirred for 15 minutes followed by the addition of 4,5-Dichloro-2-{4-[2-(3-chloro-phenylamino)-pyrimidin-4-yl]-pyridin-2-yl}-2H-pyridazin-3-one (0.7 g). The mixture was heated at 85° C. for 1 h. The suspension was poured into brine (200 mL) and extracted with ethyl acetate (3×100 mL). The organic phase were combined, dried over MgSO4, and concentrated under vacuum. Flash silica chromatography, eluting with ethyl acetate-cyclohexane (1:1), afforded the title compound as a solid (0.4128 g, 55%). Mp 118-127° C.

Synthesis Example 16

1-{4-[2-(3-Chloro-phenylamino)-pyrimidin-4-yl]-pyridin-2-yl}-2-methyl-tetrahydro-pyridazine-3,6-dione

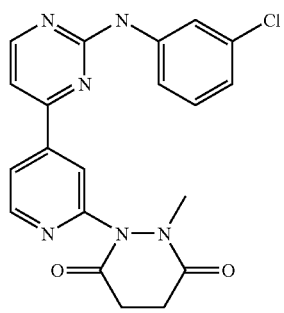

To a solution of succinic anhydride (2.16 g) in chloroform (60 mL) 1.16 mL of methyl hydrazine were added at room temperature. The solution was stirred 2 h at room temperature then heated at reflux for 1 h. The solvent was evaporated. 1 g of the obtained solid was dissolved in tetrahydrofuran (10 mL) followed by the addition of 1.55 g of N,N'-dicyclohexylcarbodiimide and 1.01 g of 1-hydroxybenzotriazole. The mixture was heated at reflux for 1 h. The mixture was cooled to 0° C. and a solution of oxalic acid (0.617 g) in methanol was added. The suspension was filtered and the solvent was evaporated. Flash silica chromatography, eluting with ethyl acetate-methanol (5%), afforded the 1-Methyl-tetrahydro-pyridazine-3,6-dione as a solid (0.4128 g, 24%). 0.014 g of Pd(dba)3 and xantphos (0.018 g) were dissolved in toluene (2 mL). The mixture was stirred at room temperature for 20 minutes. Then the 1-Methyl-tetrahydro-pyridazine-3,6-dione, the (3-Chloro-phenyl)-[4-(2-chloro-pyridin-4-yl)-pyrimidin-2-yl]-amine (0.2 g) and sodium terbutanolate (0.085 g) were added. The mixture was heated at reflux for 2 h. The suspension was poured into water (50 mL) and extracted with ethyl acetate (3×100 mL). The organic phase was separated, dried over MgSO4, filtered and concentrated. Flash silica chromatography, eluting with ethyl acetate, afforded the title compound as a solid (0.169 g, 65%). Mp 201–204° C.

The compounds in the following Tables further illustrate the invention

TABLE 1

Compounds of the general structure I.1 wherein $R_1$ to $R_{10}$, m, n, and p correspond with a line of table A and B1

I.1

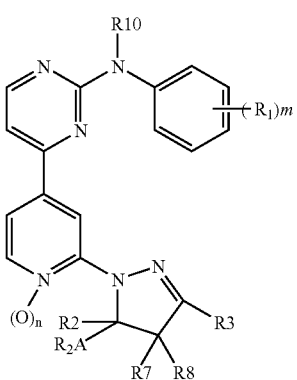

TABLE 2

Compounds of the general structure I.2 wherein $R_1$ to $R_{10}$, m, n, and p correspond with a line of table A and B2

I.2

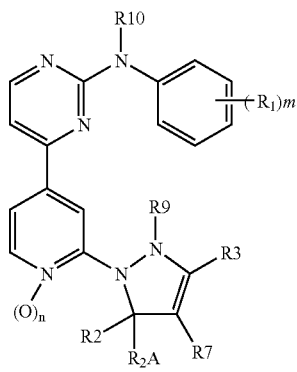

TABLE 3

Compounds of the general structure I.3 wherein $R_1$ to $R_{10}$, m, n, and p correspond with a line of table A and B3

I.3

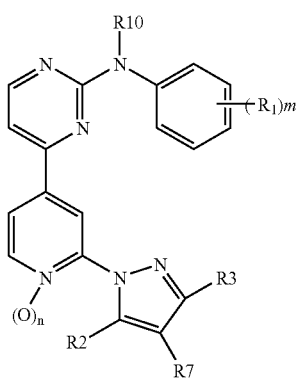

TABLE 4

Compounds of the general structure I.4 wherein $R_1$ to $R_{10}$, m, n, and p correspond with a line of table A and B4

I.4

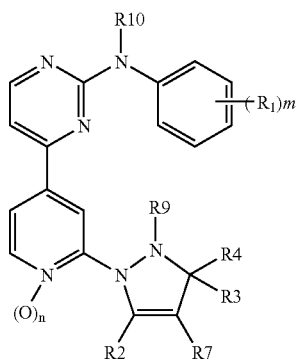

TABLE 5

Compounds of the general structure I.5 wherein $R_1$ to $R_{10}$, m, n, and p correspond with a line of table A and B5

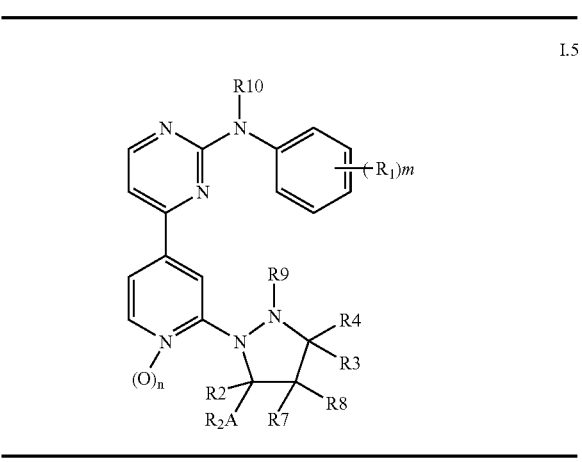

I.5

TABLE 6

Compounds of the general structure I.6 wherein $R_1$ to $R_{10}$, m, n, and p correspond with a line of table A and B6

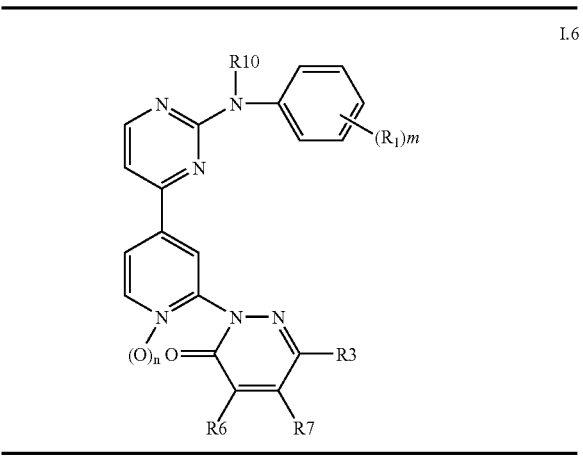

I.6

TABLE 7

Compounds of the general structure I.7 wherein $R_1$ to $R_{10}$, m, n, and p correspond with a line of table A and B7

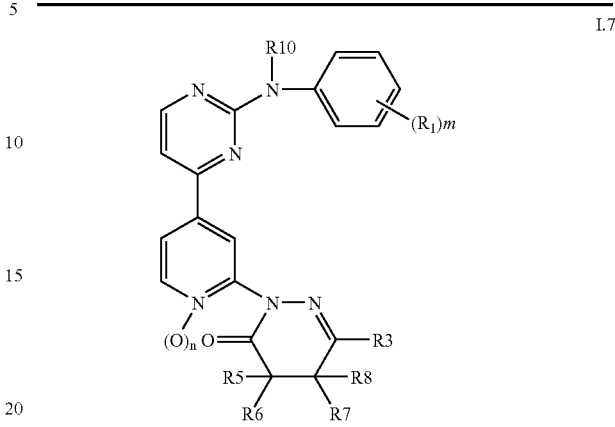

I.7

TABLE 8

Compounds of the general structure I.8 wherein R1 to R10, m, n, and p correspond with a line of table A and B8

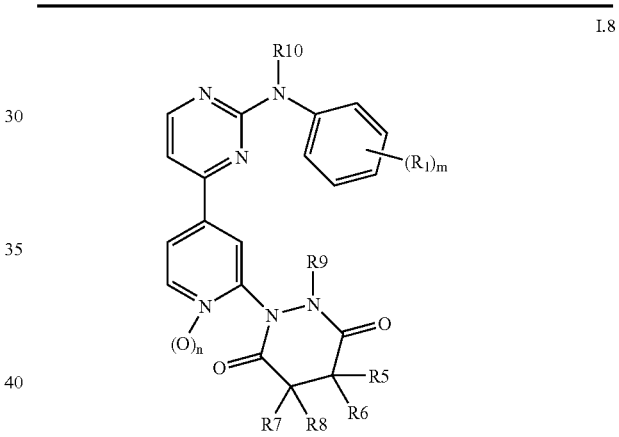

I.8

Compounds of general structure I are any combination of the definitions given in Table A and the appropriate Table B, wherein n, $R_{10}$, m and $R_1$ correspond with a line of Table A and wherein $R_2$–$R_9$ and p correspond with a line of the appropriate Table B.

TABLE A

| No. | n | $R_{10}$ | 2-$R_1$ | 3-$R_1$ | 4-$R_1$ | 5-$R_1$ | 6-$R_1$ |
|---|---|---|---|---|---|---|---|
| 001 | 0 | $CH_3$ | H | OH | H | H | F |
| 002 | 0 | $CH_3$ | H | OH | H | F | H |
| 003 | 0 | $CH_3$ | $CH_3$ | H | H | H | H |
| 004 | 0 | $CH_3$ | H | Cl | H | H | F |
| 005 | 0 | $CH_3$ | H | Cl | H | H | $CH_3$ |
| 006 | 0 | $CH_3$ | H | $CH_3$ | Cl | H | H |
| 007 | 0 | $CH_3$ | F | H | Cl | H | H |
| 008 | 0 | $CH_3$ | H | Cl | H | H | H |
| 009 | 0 | $CH_3$ | H | C(O)H | H | H | H |
| 010 | 0 | $CH_3$ | H | $CH_2OH$ | H | H | H |
| 011 | 0 | $CH_3$ | H | $CH(OH)CH_3$ | H | H | H |
| 012 | 0 | $CH_3$ | H | F | H | H | H |
| 013 | 0 | $CH_3$ | H | $CH_3$ | H | H | H |
| 014 | 0 | $CH_3$ | H | H | H | $CF_3$ | H |
| 015 | 0 | $CH_3$ | H | H | H | $OCF_3$ | H |
| 016 | 0 | $CH_3$ | H | $N(CH_3)_2$ | H | H | F |

TABLE A-continued

| No. | n | R$_{10}$ | 2-R$_1$ | 3-R$_1$ | 4-R$_1$ | 5-R$_1$ | 6-R$_1$ |
|---|---|---|---|---|---|---|---|
| 017 | 0 | CH$_3$ | H | SO$_2$N(CH$_3$)$_2$ | H | H | H |
| 018 | 0 | CH$_3$ | H | H | H | CONH$_2$ | H |
| 019 | 0 | CH$_3$ | H | H | H | OCH$_2$C≡CH | H |
| 020 | 0 | CH$_3$ | H | SC$_4$H$_9$ | H | H | H |
| 021 | 0 | H | H | OH | H | F | H |
| 022 | 0 | H | H | OH | H | H | F |
| 023 | 0 | H | CH$_3$ | H | H | H | H |
| 024 | 0 | H | H | Cl | H | H | F |
| 025 | 0 | H | H | Cl | H | H | CH$_3$ |
| 026 | 0 | H | H | CH$_3$ | Cl | H | H |
| 027 | 0 | H | F | H | Cl | H | H |
| 028 | 0 | H | H | Cl | H | H | H |
| 029 | 0 | H | H | C(O)H | H | H | H |
| 030 | 0 | H | H | CH$_2$OH | H | H | H |
| 031 | 0 | H | H | CH(OH)CH$_3$ | H | H | H |
| 032 | 0 | H | H | F | H | H | H |
| 033 | 0 | H | H | CH$_3$ | H | H | H |
| 034 | 0 | H | H | H | H | CF$_3$ | H |
| 035 | 0 | H | H | H | H | OCF$_3$ | H |
| 036 | 0 | H | H | N(CH$_3$)$_2$ | H | H | F |
| 037 | 0 | H | H | SO$_2$N(CH$_3$)$_2$ | H | H | H |
| 038 | 0 | H | H | H | H | CONH$_2$ | H |
| 039 | 0 | H | H | H | H | OCH$_2$C≡CH | H |
| 040 | 0 | H | H | SC$_4$H$_9$ | H | H | H |
| 041 | 0 | CH$_2$OCH$_3$ | H | OH | H | H | F |
| 042 | 0 | CH$_2$OCH$_3$ | H | OH | H | F | H |
| 043 | 0 | CH$_2$OCH$_3$ | CH$_3$ | H | H | H | H |
| 044 | 0 | CH$_2$OCH$_3$ | H | Cl | H | H | F |
| 045 | 0 | CH$_2$OCH$_3$ | H | Cl | H | H | CH$_3$ |
| 046 | 0 | CH$_2$OCH$_3$ | H | CH$_3$ | Cl | H | H |
| 047 | 0 | CH$_2$OCH$_3$ | F | H | Cl | H | H |
| 048 | 0 | CH$_2$OCH$_3$ | H | Cl | H | H | H |
| 049 | 0 | CH$_2$OCH$_3$ | H | C(O)H | H | H | H |
| 050 | 0 | CH$_2$OCH$_3$ | H | CH$_2$OH | H | H | H |
| 051 | 0 | CH$_2$OCH$_3$ | H | CH(OH)CH$_3$ | H | H | H |
| 052 | 0 | CH$_2$OCH$_3$ | H | F | H | H | H |
| 053 | 0 | CH$_2$OCH$_3$ | H | CH$_3$ | H | H | H |
| 054 | 0 | CH$_2$OCH$_3$ | H | H | H | CF$_3$ | H |
| 055 | 0 | CH$_2$OCH$_3$ | H | H | H | OCF$_3$ | H |
| 056 | 0 | CH$_2$OCH$_3$ | H | N(CH$_3$)$_2$ | H | H | F |
| 057 | 0 | CH$_2$OCH$_3$ | H | SO$_2$N(CH$_3$)$_2$ | H | H | H |
| 058 | 0 | CH$_2$OCH$_3$ | H | H | H | CONH$_2$ | H |
| 059 | 0 | CH$_2$OCH$_3$ | H | H | H | OCH$_2$C≡CH | H |
| 060 | 0 | CH$_2$OCH$_3$ | H | SC$_4$H$_9$ | H | H | H |
| 061 | 0 | CH$_2$OCH$_3$ | H | OH | H | H | F |
| 062 | 0 | CH$_2$OCH$_3$ | H | Cl | H | H | H |
| 063 | 0 | CH$_2$OCH$_3$ | H | C(O)H | H | H | H |
| 064 | 0 | CH$_2$OCH$_3$ | H | CH$_2$OH | H | H | H |
| 065 | 0 | CH$_2$OCH$_3$ | H | CH(OH)CH$_3$ | H | H | H |
| 066 | 0 | CH$_2$OCH$_3$ | H | F | H | H | H |
| 067 | 0 | CH$_2$OCH$_3$ | H | CH$_3$ | H | H | H |
| 068 | 0 | CH$_2$OCH$_3$ | H | H | H | CF$_3$ | H |
| 069 | 0 | CH$_2$OCH$_3$ | H | H | H | OCF$_3$ | H |
| 070 | 0 | CH$_2$OCH$_3$ | H | N(CH$_3$)$_2$ | H | H | F |
| 071 | 0 | CH$_2$OCH$_3$ | H | SO$_2$N(CH$_3$)$_2$ | H | H | H |
| 072 | 0 | CH$_2$OCH$_3$ | H | H | H | CONH$_2$ | H |
| 073 | 0 | CH$_2$SCH$_3$ | H | OH | H | H | F |
| 074 | 0 | CH$_2$SCH$_3$ | H | Cl | H | H | H |
| 075 | 0 | CH$_2$SCH$_3$ | H | C(O)H | H | H | H |
| 076 | 0 | CH$_2$SCH$_3$ | H | CH$_2$OH | H | H | H |
| 077 | 0 | CH$_2$SCH$_3$ | H | CH(OH)CH$_3$ | H | H | H |
| 078 | 0 | CH$_2$SCH$_3$ | H | F | H | H | H |
| 079 | 0 | CH$_2$SCH$_3$ | H | CH$_3$ | H | H | H |
| 080 | 0 | CH$_2$SCH$_3$ | H | H | H | CF$_3$ | H |
| 081 | 0 | CH$_2$SCH$_3$ | H | H | H | OCF$_3$ | H |
| 082 | 0 | CH$_2$SCH$_3$ | H | N(CH$_3$)$_2$ | H | H | F |
| 083 | 0 | CH$_2$SCH$_3$ | H | SO$_2$N(CH$_3$)$_2$ | H | H | H |
| 084 | 0 | CH$_2$SCH$_3$ | H | H | H | CONH$_2$ | H |
| 085 | 0 | CH$_2$CH=CH$_2$ | H | OH | H | H | F |
| 086 | 0 | CH$_2$CH=CH$_2$ | H | Cl | H | H | H |
| 087 | 0 | CH$_2$CH=CH$_2$ | H | C(O)H | H | H | H |
| 088 | 0 | CH$_2$CH=CH$_2$ | H | CH$_2$OH | H | H | H |
| 089 | 0 | CH$_2$CH=CH$_2$ | H | CH(OH)CH$_3$ | H | H | H |
| 090 | 0 | CH$_2$CH=CH$_2$ | H | F | H | H | H |
| 091 | 0 | CH$_2$CH=CH$_2$ | H | CH$_3$ | H | H | H |
| 092 | 0 | CH$_2$CH=CH$_2$ | H | H | H | CF$_3$ | H |
| 093 | 0 | CH$_2$CH=CH$_2$ | H | H | H | OCF$_3$ | H |

TABLE A-continued

| No. | n | R₁₀ | 2-R₁ | 3-R₁ | 4-R₁ | 5-R₁ | 6-R₁ |
|---|---|---|---|---|---|---|---|
| 094 | 0 | CH₂CH=CH₂ | H | N(CH₃)₂ | H | H | F |
| 095 | 0 | CH₂CH=CH₂ | H | SO₂N(CH₃)₂ | H | H | H |
| 096 | 0 | CH₂CH=CH₂ | H | H | H | CONH₂ | H |
| 097 | 0 | CH₂C≡CH | H | OH | H | H | F |
| 098 | 0 | CH₂C≡CH | H | Cl | H | H | H |
| 099 | 0 | CH₂C≡CH | H | C(O)H | H | H | H |
| 100 | 0 | CH₂C≡CH | H | CH₂OH | H | H | H |
| 101 | 0 | CH₂C≡CH | H | CH(OH)CH₃ | H | H | H |
| 102 | 0 | CH₂C≡CH | H | F | H | H | H |
| 103 | 0 | CH₂C≡CH | H | CH₃ | H | H | H |
| 104 | 0 | CH₂C≡CH | H | H | H | CF₃ | H |
| 105 | 0 | CH₂C≡CH | H | H | H | OCF₃ | H |
| 106 | 0 | CH₂C≡CH | H | N(CH₃)₂ | H | H | F |
| 107 | 0 | CH₂C≡CH | H | SO₂N(CH₃)₂ | H | H | H |
| 108 | 0 | CH₂C≡CH | H | H | H | CONH₂ | H |
| 109 | 0 | CH₂C≡CH | H | OH | H | H | F |
| 110 | 0 | CH₂Ph | H | Cl | H | H | H |
| 111 | 0 | CH₂Ph | H | C(O)H | H | H | H |
| 112 | 0 | CH₂Ph | H | CH₂OH | H | H | H |
| 113 | 0 | CH₂Ph | H | CH(OH)CH₃ | H | H | H |
| 114 | 0 | CH₂Ph | H | F | H | H | H |
| 115 | 0 | CH₂Ph | H | CH₃ | H | H | H |
| 116 | 0 | CH₂Ph | H | H | H | CF₃ | H |
| 117 | 0 | CH₂Ph | H | H | H | OCF₃ | H |
| 118 | 0 | CH₂Ph | H | N(CH₃)₂ | H | H | F |
| 119 | 0 | CH₂Ph | H | SO₂N(CH₃)₂ | H | H | H |
| 120 | 0 | H | H | Cl | CH₃ | H | H |
| 121 | 0 | H | H | Cl | CH₃ | H | H |
| 122 | 0 | H | H | Cl | OCH₃ | H | H |
| 123 | 0 | H | H | F | H | F | H |
| 124 | 0 | H | H | Cl | H | Cl | H |
| 125 | 0 | H | H | Br | H | H | H |

TABLE B-1

I.1

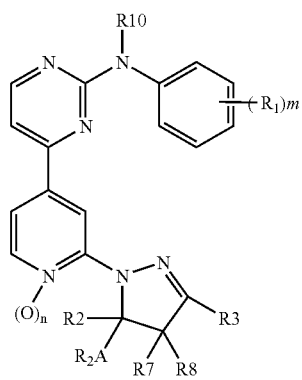

| No. | R₂ | R₂A | R₃ | R₇ | R₈ | R₉ |
|---|---|---|---|---|---|---|
| 01 | C=O | | CH₃ | CH₃ | CH₃ | |
| 02 | C=S | | CH₃ | CH₃ | H | |
| 03 | C=O | | CH₃ | CH₃ | CH₂CH₃ | |
| 04 | C=O | | CH₃ | CH₂—CH₂ | | |
| 05 | C=O | | CH₃ | CH₃ | Ph | |
| 06 | C=S | | CH₃ | CH₃ | CH₃ | |
| 07 | C=O | | H | CH₃ | CH₃ | |
| 08 | C=O | | CH₂OCH₃ | CH₃ | CH₃ | |
| 09 | C=O | | CH₃ | CH₃ | CH₂Ph | |
| 010 | C=O | | CH₃ | CH₂CH₂OC(O)CH₃ | H | |
| 011 | C=O | | CH₃ | CO₂Et | H | |
| 012 | C=O | | CH₃ | CHO | H | |
| 013 | C=O | | CH₃ | CF₃ | H | |
| 014 | C=O | | CF₃ | CF₃ | H | |
| 015 | C=O | | CF₃ | H | H | |
| 016 | C=O | | CH₂CH₃ | H | H | |
| 017 | C=O | | CH₂CH₃ | CH₃ | H | |
| 018 | C=O | | n-C₄H₉ | CH₃ | H | |

TABLE B-1-continued

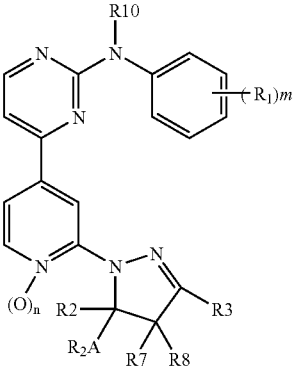

I.1

| No. | R₂ | R₂ₐ | R₃ | R₇ | R₈ | R₉ |
|---|---|---|---|---|---|---|
| 019 | C=O | | Ph | CH₃ | H | |
| 020 | C=S | | n-C₄H₉ | CH₃ | H | |
| 021 | C=S | | CH₃ | CH₃ | CH₂CH₃ | |
| 022 | C=S | | CH₃ | CH₂—CH₂ | | |
| 023 | C=S | | CH₃ | CH₃ | Ph | |
| 024 | C=S | | H | CH₃ | CH₃ | |
| 025 | C=S | | CH2OCH3 | CH₃ | CH₃ | |
| 026 | C=S | | CH₃ | CH₃ | CH₂Ph | |
| 027 | C=S | | CH₃ | CH₂CH₂OC(O)CH₃ | H | |
| 028 | C=S | | CH₃ | CO₂Et | H | |
| 029 | C=S | | CH₃ | CHO | H | |
| 030 | C=S | | CH₃ | CF₃ | H | |
| 031 | C=S | | CF₃ | CF₃ | H | |
| 032 | C=S | | CF₃ | H | H | |
| 033 | C=S | | CH₂CH₃ | H | H | |
| 034 | C=S | | CH₂CH₃ | CH₃ | H | |
| 035 | C=S | | Ph | CH₃ | H | |
| 036 | C=O | | CH₃ | CO₂Et | CH₃ | |
| 037 | C=O | | CH₃ | CHO | CH₃ | |
| 038 | C=O | | CH₃ | CF₃ | CH₃ | |
| 039 | C=O | | CF₃ | CF₃ | CH₃ | |
| 040 | C=O | | CF₃ | CH₃ | H | |
| 041 | C=O | | CH₂CH₃ | CF₃ | H | |
| 042 | C=O | | CH₂CH₃ | CH₃ | H | |
| 043 | C=S | | CH₃ | CO₂Et | CH₃ | |
| 044 | C=S | | CH₃ | CHO | CH₃ | |
| 045 | C=S | | CH₃ | CF₃ | CH₃ | |
| 046 | C=S | | CF₃ | CF₃ | CH₃ | |
| 047 | C=S | | CF₃ | CH₃ | H | |
| 048 | C=S | | CH₂CH₃ | CF₃ | H | |
| 049 | C=S | | CH₂CH₃ | CH₃ | H | |
| 050 | H | H | OCH₃ | H | H | |
| 051 | H | H | OCH₂Ph | H | H | |
| 052 | H | H | OCH₂CCH | H | H | |
| 053 | H | H | 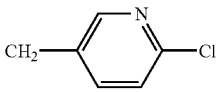 | H | H | |

TABLE B-2

I.2

Structure with R10, R1)m, R9, R3, R2, R2A, R7, (O)n substituents on pyrimidine-pyridine-pyrazole scaffold.

| No. | R$_2$ | R$_{2A}$ | R$_3$ | R$_7$ | R$_9$ |
|---|---|---|---|---|---|
| 01 | C=O | | CH$_3$ | C(O)$_2$Me | CH$_3$ |
| 02 | C=O | | CH$_3$ | CH$_3$ | CH$_3$ |
| 03 | C=O | | CH$_3$ | H | CH$_3$ |
| 04 | C=O | | CH$_3$ | CHO | CH$_3$ |
| 05 | C=O | | H | CH$_3$ | CH$_3$ |
| 06 | C=O | | CH$_3$ | CH$_3$ | CH$_2$—CH$_3$ |
| 07 | C=O | | CH$_3$ | CH$_3$ | CH$_2$PH |
| 08 | C=O | | CH$_3$ | H | CH$_3$ |
| 09 | C=O | | CH$_2$OCH$_3$ | CH$_3$ | CH$_3$ |
| 010 | C=O | | CH$_3$ | CH$_3$ | Ac |
| 011 | C=O | | CH$_2$OCH$_3$ | H | CH$_3$ |
| 012 | C=S | | CH$_3$ | H | CH$_3$ |
| 013 | C=S | | CH$_3$ | C(O)$_2$Me | CH$_3$ |
| 014 | C=S | | CH$_3$ | CH$_3$ | CH$_3$ |
| 015 | C=S | | CH$_3$ | CHO | CH$_3$ |
| 016 | C=S | | H | CH$_3$ | CH$_3$ |
| 017 | C=S | | CH$_3$ | CH$_3$ | CH$_2$—CH$_3$ |
| 018 | C=S | | CH$_3$ | CH$_3$ | CH$_2$PH |
| 019 | C=S | | CH$_3$ | H | CH$_3$ |
| 020 | C=S | | CH$_2$OCH$_3$ | CH$_3$ | CH$_3$ |
| 021 | C=S | | CH$_3$ | CH$_3$ | Ac |
| 022 | C=S | | CH$_2$OCH$_3$ | H | CH$_3$ |
| 023 | C=O | | CH$_2$Ph | CH$_3$ | CH$_3$ |
| 024 | C=O | | n-C$_4$H$_9$ | CH$_3$ | CH$_3$ |
| 025 | C=O | | CH$_2$CH$_3$ | CH$_3$ | CH$_2$CH$_3$ |
| 026 | C=O | | CH$_2$CH$_3$ | CH$_3$ | CH$_3$ |
| 027 | C=O | | CF$_3$ | n-C$_4$H$_9$ | CH$_3$ |
| 028 | C=O | | CH$_2$Ph | H | CH$_3$ |
| 029 | C=O | | n-C$_4$H$_9$ | H | CH$_3$ |
| 030 | C=O | | CH$_2$CH$_3$ | CH$_2$Ph | CH$_2$CH$_3$ |
| 031 | C=O | | CH$_2$CH$_3$ | H | CH$_3$ |
| 032 | C=O | | CF$_3$ | CH$_3$ | CH$_3$ |
| 033 | C=S | | CH$_2$Ph | CH$_3$ | CH$_3$ |
| 034 | C=S | | n-C$_4$H$_9$ | CH$_3$ | CH$_3$ |
| 035 | C=S | | CH$_2$CH$_3$ | CH$_3$ | CH$_2$CH$_3$ |
| 036 | C=S | | CH$_2$CH$_3$ | CH$_3$ | CH$_3$ |
| 037 | C=S | | CF$_3$ | n-C$_4$H$_9$ | CH$_3$ |
| 038 | C=S | | CH$_2$Ph | H | CH$_3$ |
| 039 | C=S | | n-C$_4$H$_9$ | H | CH$_3$ |
| 040 | C=S | | CH$_2$CH$_3$ | CH$_2$Ph | CH$_2$CH$_3$ |
| 041 | C=S | | CH$_2$CH$_3$ | H | CH$_3$ |
| 042 | C=S | | CF$_3$ | CH$_3$ | CH$_3$ |

TABLE B-3

I.3

Structure with R10, R1)m, R3, R2, R7, (O)n substituents on pyrimidine-pyridine-pyrazole scaffold.

| No. | R$_2$ | R$_3$ | R$_7$ |
|---|---|---|---|
| 01 | OCH3 | CH$_3$ | H |
| 02 | Oac | CH$_3$ | CH$_3$ |
| 03 | OC$_2$H$_5$ | CH$_3$ | CH$_3$ |
| 04 | OC$_2$H$_5$ | H | CH$_3$ |
| 05 | OC$_2$H$_5$ | CH$_3$ | H |
| 06 | OC$_2$H$_5$ | H | Ph |
| 07 | OC$_2$H$_5$ | CH$_2$OCH$_3$ | CH$_3$ |
| 08 | OC$_2$H$_5$ | CH$_2$OCH$_3$ | CH$_2$CH$_3$ |
| 09 | OH | CH$_2$OCH$_3$ | CH$_3$ |
| 010 | OH | CH$_2$OCH$_3$ | CH$_2$CH$_3$ |
| 011 | OH | CH$_2$OCH$_3$ | H |
| 012 | OCH3 | H | CH$_3$ |
| 013 | OCH3 | CH$_2$OCH$_3$ | CH$_3$ |
| 014 | OCH3 | CH$_2$OCH$_3$ | H |
| 015 | OH | CH$_3$ | CH$_2$CH$_3$ |
| 016 | OH | H | CH$_3$ |
| 017 | CH$_3$ | CH$_3$ | CH$_3$ |
| 018 | OAc | CH$_3$ | H |
| 019 | OH | CH$_3$ | H |
| 020 | OCH$_2$Ph | CH$_3$ | CH$_3$ |
| 021 | SCH3 | CH$_3$ | CH$_3$ |
| 022 | SCH3 | CH$_3$ | CH$_2$CH$_3$ |
| 023 | SCH3 | CH$_3$ | H |
| 024 | SCH3 | CH$_3$ | CH$_2$CH$_3$ |
| 025 | SCH3 | H | H |
| 026 | SCH3 | H | CH$_3$ |
| 027 | CH$_3$ | CH$_3$ | |
| 028 | CH$_3$ | CH$_3$ | CH$_3$ |
| 029 | CH$_3$ | CH$_3$ | C(O)$_2$Et |
| 030 | CH(CH$_3$)$_2$ | CH(CH$_3$)$_2$ | H |
| 031 | CH$_3$ | CH$_3$ | Cl |
| 032 | H | OCH$_3$ | H |
| 033 | CH$_2$OCH$_3$ | H | C(O)$_2$Me |
| 034 | CH$_2$OCH$_3$ | H | CONHMe |
| 035 | c-C$_3$H$_5$ | CH$_3$ | H |
| 036 | I—C$_3$H$_7$ | CH$_3$ | C(O)$_2$Et |
| 037 | CH$_3$ | CH$_3$ | Ph |
| 038 | CH$_3$ | CF$_3$ | H |
| 039 | H | OH | H |
| 040 | 2,4-F$_2$—Ph | C(O)$_2$Me | H |
| 041 | 2,4-F$_2$—Ph | CONHMe | H |
| 042 | SCH3 | CH$_2$OCH$_3$ | CH$_3$ |
| 043 | SCH3 | CH$_2$OCH$_3$ | H |
| 044 | SH | CH$_3$ | CH$_2$CH$_3$ |
| 045 | SH | H | CH$_3$ |
| 046 | SCH3 | CH$_3$ | H |
| 047 | SCH$_2$Ph | CH$_3$ | CH$_3$ |
| 048 | SC$_2$H$_5$ | CH$_3$ | CH$_3$ |
| 049 | SC$_2$H$_5$ | H | CH$_3$ |
| 050 | SC$_2$H$_5$ | CH$_3$ | H |
| 051 | SC$_2$H$_5$ | H | Ph |
| 052 | SC$_2$H$_5$ | CH$_2$OCH$_3$ | CH$_3$ |
| 053 | SC$_2$H$_5$ | CH$_2$OCH$_3$ | CH$_2$CH$_3$ |

TABLE B-4

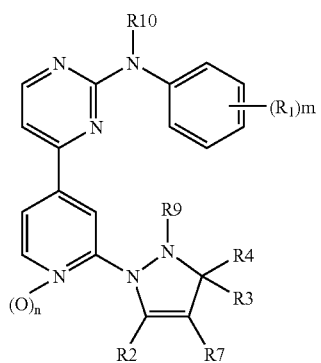

| No. | R₂ | R₃ | R₄ | R₇ | R₉ |
|---|---|---|---|---|---|
| 01 | H | C=O | | H | CH₃ |
| 02 | H | C=O | | H | 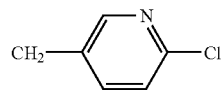 |
| 03 | H | C=O | | H | Benzyl |
| 04 | H | C=O | | H | CH₂C≡CH |
| 05 | CH₃ | C=O | | H | CH₃ |
| 06 | CH₃ | C=O | | H | CH₂CH₃ |
| 07 | CH₃ | C=O | | H | n-C₄H₉ |
| 08 | CH₃ | C=O | | H | CH₂Ph |
| 09 | CH₂CH₃ | C=O | | H | CH₃ |
| 010 | CH₂CH₃ | C=O | | H | CH₃ |
| 011 | Ph | C=O | | H | CH₃ |
| 012 | Ph | C=O | | H | CH₂CH₃ |
| 013 | Ph | C=O | | H | Ph |
| 014 | Ph | C=O | | H | n-C₄H₉ |
| 015 | H | C=S | | H | CH₃ |
| 016 | H | C=S | | H | Benzyl |
| 017 | H | C=S | | H | CH₂C≡CH |
| 018 | CH₃ | C=S | | H | CH₃ |
| 019 | CH₃ | C=S | | H | CH₂CH₃ |
| 020 | CH₃ | C=S | | H | n-C₄H₉ |
| 021 | CH₃ | C=S | | H | CH₂Ph |
| 022 | CH₂CH₃ | C=S | | H | CH₃ |
| 023 | CH₂CH₃ | C=S | | H | CH₃ |
| 024 | Ph | C=S | | H | CH₃ |
| 025 | Ph | C=S | | H | CH₂CH₃ |
| 026 | Ph | C=S | | H | Ph |
| 027 | Ph | C=S | | H | n-C₄H₉ |

TABLE B-5

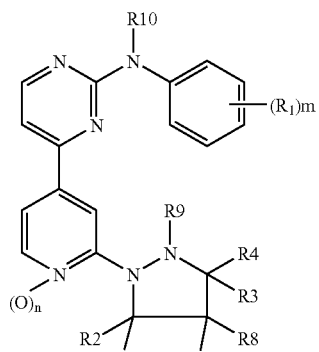

| No. | R₂ | R₂A | R₃ | R₄ | R₇ | R₈ | R₉ |
|---|---|---|---|---|---|---|---|
| 01 | H | H | C=O | | H | H | CH₃ |
| 02 | H | H | C=O | | H | H | 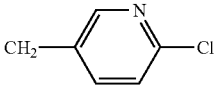 |
| 03 | H | H | C=O | | H | H | Benzyl |
| 04 | H | H | C=O | | H | H | CH₂C≡CH |
| 05 | CH₃ | H | C=O | CH₃ | | H | CH₂Ph |
| 06 | CH₃ | H | C=O | CH₃ | | H | CH₂C≡CH |
| 07 | CH₃ | H | C=O | CH₃ | | H | CH₂CH=CH₂ |
| 08 | CH₃ | H | C=O | CH₃ | | H | CH₃ |
| 09 | CH₃ | H | C=O | CH₃ | | H | CH₂CH₃ |
| 010 | CH₃ | H | C=O | | H | H | CH₂Ph |
| 011 | CH₃ | H | C=O | | H | H | CH₂C≡CH |
| 012 | CH₃ | H | C=O | | H | H | CH₂CH=CH₂ |
| 013 | CH₃ | H | C=O | | H | H | CH₃ |
| 014 | CH₃ | H | C=O | | H | H | CH₂CH₃ |
| 015 | CH₃ | CH₃ | C=O | | H | H | CH₂Ph |
| 016 | CH₃ | CH₃ | C=O | | H | H | CH₂C≡CH |
| 017 | CH₃ | CH₃ | C=O | | H | H | CH₂CH=CH₂ |
| 018 | CH₃ | CH₃ | C=O | | H | H | CH₃ |
| 019 | CH₃ | CH₃ | C=O | | H | H | CH₂CH₃ |
| 020 | CH₃ | H | C=S | | H | H | CH₂Ph |
| 021 | CH₃ | H | C=S | | H | H | CH₂C≡CH |
| 022 | CH₃ | H | C=S | | H | H | CH₂CH=CH₂ |
| 023 | CH₃ | H | C=S | | H | H | CH₃ |
| 024 | CH₃ | H | C=S | | H | H | CH₂CH₃ |
| 025 | CH₃ | CH₃ | C=S | | H | H | CH₂Ph |
| 026 | CH₃ | CH₃ | C=S | | H | H | CH₂C≡CH |
| 027 | CH₃ | CH₃ | C=S | | H | H | CH₂CH=CH₂ |
| 028 | CH₃ | CH₃ | C=S | | H | H | CH₃ |
| 029 | CH₃ | CH₃ | C=S | | H | H | CH₂CH₃ |
| 030 | C=O | | H | H | H | H | CH₃ |

TABLE B-6

I.6

[Structure: pyrimidine substituted with N(R10)-phenyl-(R1)m group and connected to a pyridine with (O)n on nitrogen, linked to a pyridazinone bearing R3, R6, R7 substituents]

| | R₃ | R₆ | R₇ |
|---|---|---|---|
| 1. | H | H | H |
| 2. | H | Cl | Cl |
| 3. | H | Cl | NHCH₃ |
| 4. | H | Cl | NHBu |
| 5. | H | Cl | N(CH₃)₂ |
| 6. | H | Cl | NBu₂ |
| 7. | H | Cl | NCH₃Bu |
| 8. | H | Cl | NEt₂ |
| 9. | H | Cl | NEtBu |
| 10. | H | Cl | SCH₃ |
| 11. | H | Cl | SBu |
| 12. | H | Cl | OCH₃ |
| 13. | H | Cl | OBu |
| 14. | H | Cl | CF₃ |
| 15. | H | Cl | OPh |
| 16. | H | Cl | CH₂OCH₃ |
| 17. | H | Cl | OCF₃ |
| 18. | H | Cl | OCF₂CF₃ |
| 19. | H | Cl | Ph |
| 20. | H | Cl | N₃ |
| 21. | H | H | I |
| 22. | H | H | CH₃ |
| 23. | H | H | Bu |
| 24. | H | H | OCH₃ |
| 25. | H | H | OBu |
| 26. | H | H | SCH₃ |
| 27. | H | H | SBu |
| 28. | H | H | NHCH₃ |
| 29. | H | H | NHBu |
| 30. | H | H | N(CH₃)₂ |
| 31. | H | H | NBu₂ |
| 32. | H | H | NCH₃Bu |
| 33. | H | H | NEt₂ |
| 34. | H | H | NEtBu |
| 35. | H | H | CF₃ |
| 36. | H | H | OPh |
| 37. | H | H | CH₂OCH₃ |
| 38. | H | H | OCF₃ |
| 39. | H | H | OCF₂CF₃ |
| 40. | H | H | Ph |
| 41. | H | H | N₃ |
| 42. | H | CH₃ | CH₃ |
| 43. | H | CH₃ | Bu |
| 44. | H | CH₃ | OCH₃ |
| 45. | H | CH₃ | OBu |
| 46. | H | CH₃ | SCH₃ |
| 47. | H | CH₃ | SBu |
| 48. | H | CH₃ | NHCH₃ |
| 49. | H | CH₃ | NHBu |
| 50. | H | CH₃ | N(CH₃)₂ |
| 51. | H | CH₃ | NBu₂ |
| 52. | H | CH₃ | NCH₃Bu |
| 53. | H | CH₃ | NEt₂ |
| 54. | H | CH₃ | NEtBu |
| 55. | H | CH₃ | CF₃ |
| 56. | H | CH₃ | OPh |

TABLE B-6-continued

I.6

|  | R₃ | R₆ | R₇ |
|---|---|---|---|
| 57. | H | CH₃ | CH₂OCH₃ |
| 58. | H | CH₃ | OCF₃ |
| 59. | H | CH₃ | OCF₂CF₃ |
| 60. | H | CH₃ | Ph |
| 61. | H | CH₃ | N₃ |
| 62. | H | nBu | CH₃ |
| 63. | H | nBu | Bu |
| 64. | H | nBu | OCH₃ |
| 65. | H | nBu | OBu |
| 66. | H | nBu | SCH₃ |
| 67. | H | nBu | SBu |
| 68. | H | nBu | NHCH₃ |
| 69. | H | nBu | NHBu |
| 70. | H | nBu | N(CH₃)₂ |
| 71. | H | nBu | NBu₂ |
| 72. | H | nBu | NCH₃Bu |
| 73. | H | nBu | NEt₂ |
| 74. | H | nBu | NEtBu |
| 75. | H | nBu | CF₃ |
| 76. | H | nBu | OPh |
| 77. | H | nBu | CH₂OCH₃ |
| 78. | H | nBu | OCF₃ |
| 79. | H | nBu | OCF₂CF₃ |
| 80. | H | nBu | Ph |
| 81. | H | nBu | N₃ |
| 82. | H | I | H |
| 83. | H | CH₃ | H |
| 84. | H | Bu | H |
| 85. | H | OCH₃ | H |
| 86. | H | OBu | H |
| 87. | H | SCH₃ | H |
| 88. | H | SBu | H |
| 89. | H | NHCH₃ | H |
| 90. | H | NHBu | H |
| 91. | H | N(CH₃)₂ | H |
| 92. | H | NBu₂ | H |
| 93. | H | NCH₃Bu | H |
| 94. | H | NEt₂ | H |
| 95. | H | NEtBu | H |
| 96. | H | CF₃ | H |
| 97. | H | OPh | H |
| 98. | H | CH₂OCH₃ | H |
| 99. | H | OCF₃ | H |
| 100. | H | OCF₂CF₃ | H |
| 101. | H | Ph | H |
| 102. | H | N₃ | H |
| 103. | H | CH₃ | CH₃ |
| 104. | H | Bu | CH₃ |
| 105. | H | OCH₃ | CH₃ |
| 106. | H | OBu | CH₃ |
| 107. | H | SCH₃ | CH₃ |
| 108. | H | SBu | CH₃ |
| 109. | H | NHCH₃ | CH₃ |
| 110. | H | NHBu | CH₃ |
| 111. | H | N(CH₃)₂ | CH₃ |
| 112. | H | NBu₂ | CH₃ |

TABLE B-6-continued

I.6

[Structure: pyrimidine linked via NR10 to phenyl(R1)m; pyrimidine 4-position linked to pyridine (with (O)n on N); pyridine linked to pyridazinone bearing R3, R6, R7]

| | R$_3$ | R$_6$ | R$_7$ |
|---|---|---|---|
| 113. | H | NCH$_3$Bu | CH$_3$ |
| 114. | H | NEt$_2$ | CH$_3$ |
| 115. | H | NEtBu | CH$_3$ |
| 116. | H | CF$_3$ | CH$_3$ |
| 117. | H | OPh | CH$_3$ |
| 118. | H | CH$_2$OCH$_3$ | CH$_3$ |
| 119. | H | OCF$_3$ | CH$_3$ |
| 120. | H | OCF$_2$CF$_3$ | CH$_3$ |
| 121. | H | Ph | CH$_3$ |
| 122. | H | N$_3$ | CH$_3$ |
| 123. | H | CH$_3$ | nBu |
| 124. | H | nBu | nBu |
| 125. | H | OCH$_3$ | nBu |
| 126. | H | OBu | nBu |
| 127. | H | SCH$_3$ | nBu |
| 128. | H | SBu | nBu |
| 129. | H | NHCH$_3$ | nBu |
| 130. | H | NHBu | nBu |
| 131. | H | N(CH$_3$)$_2$ | nBu |
| 132. | H | NBu$_2$ | nBu |
| 133. | H | NCH$_3$Bu | nBu |
| 134. | H | NEt$_2$ | nBu |
| 135. | H | NEtBu | nBu |
| 136. | H | CF$_3$ | nBu |
| 137. | H | OPh | nBu |
| 138. | H | CH$_2$OCH$_3$ | nBu |
| 139. | H | OCF$_3$ | nBu |
| 140. | H | OCF$_2$CF$_3$ | nBu |
| 141. | H | Ph | nBu |
| 142. | H | N$_3$ | nBu |
| 143. | H | NHCH$_3$ | Cl |
| 144. | H | NHBu | Cl |
| 145. | H | N(CH$_3$)$_2$ | Cl |
| 146. | H | NBu$_2$ | Cl |
| 147. | H | NCH$_3$Bu | Cl |
| 148. | H | NEt$_2$ | Cl |
| 149. | H | NEtBu | Cl |
| 150. | H | SCH$_3$ | Cl |
| 151. | H | SBu | Cl |
| 152. | H | OCH$_3$ | Cl |
| 153. | H | OBu | Cl |
| 154. | H | CF$_3$ | Cl |
| 155. | H | OPh | Cl |
| 156. | H | CH$_2$OCH$_3$ | Cl |
| 157. | H | OCF$_3$ | Cl |
| 158. | H | OCF$_2$CF$_3$ | Cl |
| 159. | H | Ph | Cl |
| 160. | H | N$_3$ | Cl |
| 161. | H | NHCH$_3$ | NHCH$_3$ |
| 162. | H | NHBu | NHBu |
| 163. | H | N(CH$_3$)$_2$ | N(CH$_3$)$_2$ |
| 164. | H | NBu$_2$ | NBu$_2$ |
| 165. | H | NCH$_3$Bu | NCH$_3$Bu |
| 166. | H | NEt$_2$ | NEt$_2$ |
| 167. | H | NEtBu | NEtBu |
| 168. | H | SCH$_3$ | SCH$_3$ |

TABLE B-6-continued

I.6

|  | R₃ | R₆ | R₇ |
|---|---|---|---|
| 169. | H | SBu | SBu |
| 170. | H | OCH₃ | OCH₃ |
| 171. | H | OBu | OBu |
| 172. | H | CF₃ | CF₃ |
| 173. | H | OPh | OPh |
| 174. | H | CH₂OCH₃ | CH₂OCH₃ |
| 175. | H | OCF₃ | OCF₃ |
| 176. | H | OCF₂CF₃ | OCF₂CF₃ |
| 177. | H | Ph | Ph |
| 178. | H | N₃ | N₃ |
| 179. | CH₃ | H | H |
| 180. | CH₃ | Cl | Cl |
| 181. | CH₃ | Cl | NHCH₃ |
| 182. | CH₃ | Cl | NHBu |
| 183. | CH₃ | Cl | N(CH₃)₂ |
| 184. | CH₃ | Cl | NBu₂ |
| 185. | CH₃ | Cl | NCH₃Bu |
| 186. | CH₃ | Cl | NEt₂ |
| 187. | CH₃ | Cl | NEtBu |
| 188. | CH₃ | Cl | SCH₃ |
| 189. | CH₃ | Cl | SBu |
| 190. | CH₃ | Cl | OCH₃ |
| 191. | CH₃ | Cl | OBu |
| 192. | CH₃ | Cl | CF₃ |
| 193. | CH₃ | Cl | OPh |
| 194. | CH₃ | Cl | CH₂OCH₃ |
| 195. | CH₃ | Cl | OCF₃ |
| 196. | CH₃ | Cl | OCF₂CF₃ |
| 197. | CH₃ | Cl | Ph |
| 198. | CH₃ | Cl | N₃ |
| 199. | CH₃ | H | I |
| 200. | CH₃ | H | CH₃ |
| 201. | CH₃ | H | Bu |
| 202. | CH₃ | H | OCH₃ |
| 203. | CH₃ | H | OBu |
| 204. | CH₃ | H | SCH₃ |
| 205. | CH₃ | H | SBu |
| 206. | CH₃ | H | NHCH₃ |
| 207. | CH₃ | H | NHBu |
| 208. | CH₃ | H | N(CH₃)₂ |
| 209. | CH₃ | H | NBu₂ |
| 210. | CH₃ | H | NCH₃Bu |
| 211. | CH₃ | H | NEt₂ |
| 212. | CH₃ | H | NEtBu |
| 213. | CH₃ | H | CF₃ |
| 214. | CH₃ | H | OPh |
| 215. | CH₃ | H | CH₂OCH₃ |
| 216. | CH₃ | H | OCF₃ |
| 217. | CH₃ | H | OCF₂CF₃ |
| 218. | CH₃ | H | Ph |
| 219. | CH₃ | H | N3 |
| 220. | CH₃ | CH₃ | CH₃ |
| 221. | CH₃ | CH₃ | Bu |
| 222. | CH₃ | CH₃ | OCH₃ |
| 223. | CH₃ | CH₃ | OBu |
| 224. | CH₃ | CH₃ | SCH₃ |

TABLE B-6-continued

I.6

|  | $R_3$ | $R_6$ | $R_7$ |
|---|---|---|---|
| 225. | CH$_3$ | CH$_3$ | SBu |
| 226. | CH$_3$ | CH$_3$ | NHCH$_3$ |
| 227. | CH$_3$ | CH$_3$ | NHBu |
| 228. | CH$_3$ | CH$_3$ | N(CH$_3$)$_2$ |
| 229. | CH$_3$ | CH$_3$ | NBu$_2$ |
| 230. | CH$_3$ | CH$_3$ | NCH$_3$Bu |
| 231. | CH$_3$ | CH$_3$ | NEt$_2$ |
| 232. | CH$_3$ | CH$_3$ | NEtBu |
| 233. | CH$_3$ | CH$_3$ | CF$_3$ |
| 234. | CH$_3$ | CH$_3$ | OPh |
| 235. | CH$_3$ | CH$_3$ | CH$_2$OCH$_3$ |
| 236. | CH$_3$ | CH$_3$ | OCF$_3$ |
| 237. | CH$_3$ | CH$_3$ | OCF$_2$CF$_3$ |
| 238. | CH$_3$ | CH$_3$ | Ph |
| 239. | CH$_3$ | CH$_3$ | N$_3$ |
| 240. | CH$_3$ | nBu | CH$_3$ |
| 241. | CH$_3$ | nBu | Bu |
| 242. | CH$_3$ | nBu | OCH$_3$ |
| 243. | CH$_3$ | nBu | OBu |
| 244. | CH$_3$ | nBu | SCH$_3$ |
| 245. | CH$_3$ | nBu | SBu |
| 246. | CH$_3$ | nBu | NHCH$_3$ |
| 247. | CH$_3$ | nBu | NHBu |
| 248. | CH$_3$ | nBu | N(CH$_3$)$_2$ |
| 249. | CH$_3$ | nBu | NBu$_2$ |
| 250. | CH$_3$ | nBu | NCH$_3$Bu |
| 251. | CH$_3$ | nBu | NEt$_2$ |
| 252. | CH$_3$ | nBu | NEtBu |
| 253. | CH$_3$ | nBu | CF$_3$ |
| 254. | CH$_3$ | nBu | OPh |
| 255. | CH$_3$ | nBu | CH$_2$OCH$_3$ |
| 256. | CH$_3$ | nBu | OCF$_3$ |
| 257. | CH$_3$ | nBu | OCF$_2$CF$_3$ |
| 258. | CH$_3$ | nBu | Ph |
| 259. | CH$_3$ | nBu | N3 |
| 260. | CH$_3$ | I | H |
| 261. | CH$_3$ | CH$_3$ | H |
| 262. | CH$_3$ | Bu | H |
| 263. | CH$_3$ | OCH$_3$ | H |
| 264. | CH$_3$ | OBu | H |
| 265. | CH$_3$ | SCH$_3$ | H |
| 266. | CH$_3$ | SBu | H |
| 267. | CH$_3$ | NHCH$_3$ | H |
| 268. | CH$_3$ | NHBu | H |
| 269. | CH$_3$ | N(CH$_3$)$_2$ | H |
| 270. | CH$_3$ | NBu$_2$ | H |
| 271. | CH$_3$ | NCH$_3$Bu | H |
| 272. | CH$_3$ | NEt$_2$ | H |
| 273. | CH$_3$ | NEtBu | H |
| 274. | CH$_3$ | CF$_3$ | H |
| 275. | CH$_3$ | OPh | H |
| 276. | CH$_3$ | CH$_2$OCH$_3$ | H |
| 277. | CH$_3$ | OCF$_3$ | H |
| 278. | CH$_3$ | OCF$_2$CF$_3$ | H |
| 279. | CH$_3$ | Ph | H |
| 280. | CH$_3$ | N$_3$ | H |

TABLE B-6-continued

I.6

| | R$_3$ | R$_6$ | R$_7$ |
|---|---|---|---|
| 281. | CH$_3$ | CH$_3$ | CH$_3$ |
| 282. | CH$_3$ | Bu | CH$_3$ |
| 283. | CH$_3$ | OCH$_3$ | CH$_3$ |
| 284. | CH$_3$ | OBu | CH$_3$ |
| 285. | CH$_3$ | SCH$_3$ | CH$_3$ |
| 286. | CH$_3$ | SBu | CH$_3$ |
| 287. | CH$_3$ | NHCH$_3$ | CH$_3$ |
| 288. | CH$_3$ | NHBu | CH$_3$ |
| 289. | CH$_3$ | N(CH$_3$)$_2$ | CH$_3$ |
| 290. | CH$_3$ | NBu$_2$ | CH$_3$ |
| 291. | CH$_3$ | NCH$_3$Bu | CH$_3$ |
| 292. | CH$_3$ | NEt$_2$ | CH$_3$ |
| 293. | CH$_3$ | NEtBu | CH$_3$ |
| 294. | CH$_3$ | CF$_3$ | CH$_3$ |
| 295. | CH$_3$ | OPh | CH$_3$ |
| 296. | CH$_3$ | CH$_2$OCH$_3$ | CH$_3$ |
| 297. | CH$_3$ | OCF$_3$ | CH$_3$ |
| 298. | CH$_3$ | OCF$_2$CF$_3$ | CH$_3$ |
| 299. | CH$_3$ | Ph | CH$_3$ |
| 300. | CH$_3$ | N$_3$ | CH$_3$ |
| 301. | CH$_3$ | CH$_3$ | nBu |
| 302. | CH$_3$ | Bu | nBu |
| 303. | CH$_3$ | OCH$_3$ | nBu |
| 304. | CH$_3$ | OBu | nBu |
| 305. | CH$_3$ | SCH$_3$ | nBu |
| 306. | CH$_3$ | SBu | nBu |
| 307. | CH$_3$ | NHCH$_3$ | nBu |
| 308. | CH$_3$ | NHBu | nBu |
| 309. | CH$_3$ | N(CH$_3$)$_2$ | nBu |
| 310. | CH$_3$ | NBu$_2$ | nBu |
| 311. | CH$_3$ | NCH$_3$Bu | nBu |
| 312. | CH$_3$ | NEt$_2$ | nBu |
| 313. | CH$_3$ | NEtBu | nBu |
| 314. | CH$_3$ | CF$_3$ | nBu |
| 315. | CH$_3$ | OPh | nBu |
| 316. | CH$_3$ | CH$_2$OCH$_3$ | nBu |
| 317. | CH$_3$ | OCF$_3$ | nBu |
| 318. | CH$_3$ | OCF$_2$CF$_3$ | nBu |
| 319. | CH$_3$ | Ph | nBu |
| 320. | CH$_3$ | N$_3$ | nBu |
| 321. | CH$_3$ | NHCH$_3$ | Cl |
| 322. | CH$_3$ | NHBu | Cl |
| 323. | CH$_3$ | N(CH$_3$)$_2$ | Cl |
| 324. | CH$_3$ | NBu$_2$ | Cl |
| 325. | CH$_3$ | NCH$_3$Bu | Cl |
| 326. | CH$_3$ | NEt$_2$ | Cl |
| 327. | CH$_3$ | NEtBu | Cl |
| 328. | CH$_3$ | SCH$_3$ | Cl |
| 329. | CH$_3$ | SBu | Cl |
| 330. | CH$_3$ | OCH$_3$ | Cl |
| 331. | CH$_3$ | OBu | Cl |
| 332. | CH$_3$ | CF$_3$ | Cl |
| 333. | CH$_3$ | OPh | Cl |
| 334. | CH$_3$ | CH$_2$OCH$_3$ | Cl |
| 335. | CH$_3$ | OCF$_3$ | Cl |
| 336. | CH$_3$ | OCF$_2$CF$_3$ | Cl |

TABLE B-6-continued

I.6

[Structure: pyrimidine with R10-N-phenyl(R1)m substituent, connected to pyridine (with (O)n on N) connected to pyridazinone with R3, R6, R7 substituents]

| | R3 | R6 | R7 |
|---|---|---|---|
| 337. | CH3 | Ph | Cl |
| 338. | CH3 | N3 | Cl |
| 339. | CH3 | NHCH3 | NHCH3 |
| 340. | CH3 | NHBu | NHBu |
| 341. | CH3 | N(CH3)2 | N(CH3)2 |
| 342. | CH3 | NBu2 | NBu2 |
| 343. | CH3 | NCH3Bu | NCH3Bu |
| 344. | CH3 | NEt2 | NEt2 |
| 345. | CH3 | NEtBu | NEtBu |
| 346. | CH3 | SCH3 | SCH3 |
| 347. | CH3 | SBu | SBu |
| 348. | CH3 | OCH3 | OCH3 |
| 349. | CH3 | OBu | OBu |
| 350. | CH3 | CF3 | CF3 |
| 351. | CH3 | OPh | OPh |
| 352. | CH3 | CH2OCH3 | CH2OCH3 |
| 353. | CH3 | OCF3 | OCF3 |
| 354. | CH3 | OCF2CF3 | OCF2CF3 |
| 355. | CH3 | Ph | Ph |
| 356. | CH3 | N3 | N3 |
| 357. | nBu | H | H |
| 358. | nBu | Cl | Cl |
| 359. | nBu | Cl | NHCH3 |
| 360. | nBu | Cl | NHBu |
| 361. | nBu | Cl | N(CH3)2 |
| 362. | nBu | Cl | NBu2 |
| 363. | nBu | Cl | NCH3Bu |
| 364. | nBu | Cl | NEt2 |
| 365. | nBu | Cl | NEtBu |
| 366. | nBu | Cl | SCH3 |
| 367. | nBu | Cl | SBu |
| 368. | nBu | Cl | OCH3 |
| 369. | nBu | Cl | OBu |
| 370. | nBu | Cl | CF3 |
| 371. | nBu | Cl | OPh |
| 372. | nBu | Cl | CH2OCH3 |
| 373. | nBu | Cl | OCF3 |
| 374. | nBu | Cl | OCF2CF3 |
| 375. | nBu | Cl | Ph |
| 376. | nBu | Cl | N3 |
| 377. | nBu | H | I |
| 378. | nBu | H | CH3 |
| 379. | nBu | H | Bu |
| 380. | nBu | H | OCH3 |
| 381. | nBu | H | OBu |
| 382. | nBu | H | SCH3 |
| 383. | nBu | H | SBu |
| 384. | nBu | H | NHCH3 |
| 385. | nBu | H | NHBu |
| 386. | nBu | H | N(CH3)2 |
| 387. | nBu | H | NBu2 |
| 388. | nBu | H | NCH3Bu |
| 389. | nBu | H | NEt2 |
| 390. | nBu | H | NEtBu |
| 391. | nBu | H | CF3 |
| 392. | nBu | H | OPh |

TABLE B-6-continued

I.6

| | R3 | R6 | R7 |
|---|---|---|---|
| 393. | nBu | H | CH2OCH3 |
| 394. | nBu | H | OCF3 |
| 395. | nBu | H | OCF2CF3 |
| 396. | nBu | H | Ph |
| 397. | nBu | H | N3 |
| 398. | nBu | CH3 | CH3 |
| 399. | nBu | CH3 | Bu |
| 400. | nBu | CH3 | OCH3 |
| 401. | nBu | CH3 | OBu |
| 402. | nBu | CH3 | SCH3 |
| 403. | nBu | CH3 | SBu |
| 404. | nBu | CH3 | NHCH3 |
| 405. | nBu | CH3 | NHBu |
| 406. | nBu | CH3 | N(CH3)2 |
| 407. | nBu | CH3 | NBu2 |
| 408. | nBu | CH3 | NCH3Bu |
| 409. | nBu | CH3 | NEt2 |
| 410. | nBu | CH3 | NEtBu |
| 411. | nBu | CH3 | CF3 |
| 412. | nBu | CH3 | OPh |
| 413. | nBu | CH3 | CH2OCH3 |
| 414. | nBu | CH3 | OCF3 |
| 415. | nBu | CH3 | OCF2CF3 |
| 416. | nBu | CH3 | Ph |
| 417. | nBu | CH3 | N3 |
| 418. | nBu | nBu | CH3 |
| 419. | nBu | nBu | Bu |
| 420. | nBu | nBu | OCH3 |
| 421. | nBu | nBu | OBu |
| 422. | nBu | nBu | SCH3 |
| 423. | nBu | nBu | SBu |
| 424. | nBu | nBu | NHCH3 |
| 425. | nBu | nBu | NHBu |
| 426. | nBu | nBu | N(CH3)2 |
| 427. | nBu | nBu | NBu2 |
| 428. | nBu | nBu | NCH3Bu |
| 429. | nBu | nBu | NEt2 |
| 430. | nBu | nBu | NEtBu |
| 431. | nBu | nBu | CF3 |
| 432. | nBu | nBu | OPh |
| 433. | nBu | nBu | CH2OCH3 |
| 434. | nBu | nBu | OCF3 |
| 435. | nBu | nBu | OCF2CF3 |
| 436. | nBu | nBu | Ph |
| 437. | nBu | nBu | N3 |
| 438. | nBu | I | H |
| 439. | nBu | CH3 | H |
| 440. | nBu | Bu | H |
| 441. | nBu | OCH3 | H |
| 442. | nBu | OBu | H |
| 443. | nBu | SCH3 | H |
| 444. | nBu | SBu | H |
| 445. | nBu | NHCH3 | H |
| 446. | nBu | NHBu | H |
| 447. | nBu | N(CH3)2 | H |
| 448. | nBu | NBu2 | H |

TABLE B-6-continued

I.6

|  | R₃ | R₆ | R₇ |
|---|---|---|---|
| 449. | nBu | NCH₃Bu | H |
| 450. | nBu | NEt₂ | H |
| 451. | nBu | NEtBu | H |
| 452. | nBu | CF₃ | H |
| 453. | nBu | OPh | H |
| 454. | nBu | CH₂OCH₃ | H |
| 455. | nBu | OCF₃ | H |
| 456. | nBu | OCF₂CF₃ | H |
| 457. | nBu | Ph | H |
| 458. | nBu | N₃ | H |
| 459. | nBu | CH₃ | CH₃ |
| 460. | nBu | Bu | CH₃ |
| 461. | nBu | OCH₃ | CH₃ |
| 462. | nBu | OBu | CH₃ |
| 463. | nBu | SCH₃ | CH₃ |
| 464. | nBu | SBu | CH₃ |
| 465. | nBu | NHCH₃ | CH₃ |
| 466. | nBu | NHBu | CH₃ |
| 467. | nBu | N(CH₃)₂ | CH₃ |
| 468. | nBu | NBu₂ | CH₃ |
| 469. | nBu | NCH₃Bu | CH₃ |
| 470. | nBu | NEt₂ | CH₃ |
| 471. | nBu | NEtBu | CH₃ |
| 472. | nBu | CF₃ | CH₃ |
| 473. | nBu | OPh | CH₃ |
| 474. | nBu | CH₂OCH₃ | CH₃ |
| 475. | nBu | OCF₃ | CH₃ |
| 476. | nBu | OCF₂CF₃ | CH₃ |
| 477. | nBu | Ph | CH₃ |
| 478. | nBu | N₃ | CH₃ |
| 479. | nBu | CH₃ | nBu |
| 480. | nBu | nBu | nBu |
| 481. | nBu | OCH₃ | nBu |
| 482. | nBu | OBu | nBu |
| 483. | nBu | SCH₃ | nBu |
| 484. | nBu | SBu | nBu |
| 485. | nBu | NHCH₃ | nBu |
| 486. | nBu | NHBu | nBu |
| 487. | nBu | N(CH₃)₂ | nBu |
| 488. | nBu | NBu₂ | nBu |
| 489. | nBu | NCH₃Bu | nBu |
| 490. | nBu | NEt₂ | nBu |
| 491. | nBu | NEtBu | nBu |
| 492. | nBu | CF₃ | nBu |
| 493. | nBu | OPh | nBu |
| 494. | nBu | CH₂OCH₃ | nBu |
| 495. | nBu | OCF₃ | nBu |
| 496. | nBu | OCF₂CF₃ | nBu |
| 497. | nBu | Ph | nBu |
| 498. | nBu | N₃ | nBu |
| 499. | nBu | NHCH₃ | Cl |
| 500. | nBu | NHBu | Cl |
| 501. | nBu | N(CH₃)₂ | Cl |
| 502. | nBu | NBu₂ | Cl |
| 503. | nBu | NCH₃Bu | Cl |
| 504. | nBu | NEt₂ | Cl |

TABLE B-6-continued

I.6

| | R₃ | R₆ | R₇ |
|---|---|---|---|
| 505. | nBu | NEtBu | Cl |
| 506. | nBu | SCH₃ | Cl |
| 507. | nBu | SBu | Cl |
| 508. | nBu | OCH₃ | Cl |
| 509. | nBu | OBu | Cl |
| 510. | nBu | CF₃ | Cl |
| 511. | nBu | OPh | Cl |
| 512. | nBu | CH₂OCH₃ | Cl |
| 513. | nBu | OCF₃ | Cl |
| 514. | nBu | OCF₂CF₃ | Cl |
| 515. | nBu | Ph | Cl |
| 516. | nBu | N₃ | Cl |
| 517. | nBu | NHCH₃ | NHCH₃ |
| 518. | nBu | NHBu | NHBu |
| 519. | nBu | N(CH₃)₂ | N(CH₃)₂ |
| 520. | nBu | NBu₂ | NBu₂ |
| 521. | nBu | NCH₃Bu | NCH₃Bu |
| 522. | nBu | NEt₂ | NEt₂ |
| 523. | nBu | NEtBu | NEtBu |
| 524. | nBu | SCH₃ | SCH₃ |
| 525. | nBu | SBu | SBu |
| 526. | nBu | OCH₃ | OCH₃ |
| 527. | nBu | OBu | OBu |
| 528. | nBu | CF₃ | CF₃ |
| 529. | nBu | OPh | OPh |
| 530. | nBu | CH₂OCH₃ | CH₂OCH₃ |
| 531. | nBu | OCF₃ | OCF₃ |
| 532. | nBu | OCF₂CF₃ | OCF₂CF₃ |
| 533. | nBu | Ph | Ph |
| 534. | nBu | N₃ | N₃ |
| 535. | Ph | H | H |
| 536. | Ph | CH₃ | CH₃ |
| 537. | Ph | CH₃ | H |
| 538. | Ph | H | CH₃ |
| 539. | CH₂OCH₃ | H | H |
| 540. | CH₂OCH₃ | CH₃ | CH₃ |
| 541. | CH₂OCH₃ | CH₃ | H |
| 542. | CH₂OCH₃ | H | CH₃ |
| 543. | CF₃ | H | H |
| 544. | CF₃ | CH₃ | CH₃ |
| 545. | CF₃ | CH₃ | H |
| 546. | CF₃ | H | CH₃ |
| 547. | OH | H | H |
| 548. | OH | CH₃ | CH₃ |
| 549. | OH | CH₃ | H |
| 550. | OH | H | CH₃ |
| 551. | OH | CHO | H |
| 552. | OH | CHO | CH₃ |
| 553. | OH | H | CF₃ |
| 554. | OH | CF₃ | H |
| 555. | OH | CF₃ | CF₃ |
| 556. | OH | CH₂OCH₃ | CH₃ |
| 557. | OH | CH₃ | CH₂OCH₃ |
| 558. | OH | CH₂OCH₃ | H |
| 559. | OH | H | CH₂OCH₃ |
| 560. | H | CHO | H |

TABLE B-6-continued

I.6

|  | R$_3$ | R$_6$ | R$_7$ |
|---|---|---|---|
| 561. | CH$_3$ | CHO | H |
| 562. | CF$_3$ | CHO | H |
| 563. | CH$_2$OCH$_3$ | CHO | H |
| 564. | nBu | CHO | H |
| 565. | H | CHO | CH$_3$ |
| 566. | CH$_3$ | CHO | CH$_3$ |
| 567. | CF$_3$ | CHO | CH$_3$ |
| 568. | CH$_2$OCH$_3$ | CHO | CH$_3$ |
| 569. | nBu | CHO | CH$_3$ |
| 570. | H | H | CHO |
| 571. | CH$_3$ | H | CHO |
| 572. | CF$_3$ | H | CHO |
| 573. | CH$_2$OCH$_3$ | H | CHO |
| 574. | nBu | H | CHO |
| 575. | H | CH$_3$ | CHO |
| 576. | CH$_3$ | CH$_3$ | CHO |
| 577. | CF$_3$ | CH$_3$ | CHO |
| 578. | CH$_2$OCH$_3$ | CH$_3$ | CHO |
| 579. | nBu | CH$_3$ | CHO |
| 580. | H | Cl | CH$_3$ |
| 581. | H | CH$_3$ | Cl |
| 582. | H | CF$_3$ | Cl |
| 583. | H | Cl | CF$_3$ |
| 584. | CH$_3$ | Cl | CH$_3$ |
| 585. | CH$_3$ | CH$_3$ | Cl |
| 586. | CH$_3$ | CF$_3$ | Cl |
| 587. | CH$_3$ | Cl | CF$_3$ |
| 588. | CF$_3$ | Cl | CH$_3$ |
| 589. | CF$_3$ | CH$_3$ | Cl |
| 590. | CF$_3$ | CF$_3$ | Cl |
| 591. | CF$_3$ | Cl | CF$_3$ |
| 592. | OCH$_3$ | H | H |
| 593. | OCH$_3$ | CH$_3$ | CH$_3$ |
| 594. | OCH$_3$ | CH$_3$ | H |
| 595. | OCH$_3$ | H | CH$_3$ |
| 596. | OCH$_3$ | CHO | H |
| 597. | OCH$_3$ | CHO | CH$_3$ |
| 598. | OCH$_3$ | H | CF$_3$ |
| 599. | OCH$_3$ | CF$_3$ | H |
| 600. | OCH$_3$ | CF$_3$ | CF$_3$ |
| 601. | OCH$_3$ | CH$_2$OCH$_3$ | CH$_3$ |
| 602. | OCH$_3$ | CH$_3$ | CH$_2$OCH$_3$ |
| 603. | OCH$_3$ | CH$_2$OCH$_3$ | H |
| 604. | OCH$_3$ | H | CH$_2$OCH$_3$ |
| 605. | H | Cl | OCH$_2$CH$_3$ |
| 606. | H | Cl | SCH$_2$CH$_3$ |
| 607. | H | Cl | Morpholin |
| 608. | H | Cl | Pyperidin |
| 609. | H | Pyperidin | Pyperidin |

TABLE B-6-continued

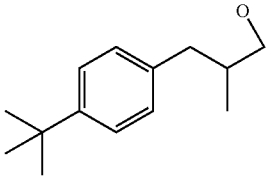

I.6

|   | R₃ | R₆ | R₇ |
|---|---|---|---|
| 610. | H | 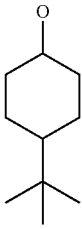 | Cl |
| 611. | H | 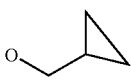 | Cl |
| 612. | H | CH₃(CH₂)₁₃O | Cl |
| 613. | H | OCH₂Ph-3-Cl | Cl |
| 614. | H | Cl | OCH₂Ph-3-Cl |
| 615. | H | O(CH₂)₂ C≡CH | Cl |
| 616. | H | OCH(CH₃)=CH₂ | Cl |
| 617. | H | O(CH₂)₂ CH=CH₂ | Cl |
| 618. | H | Cl | O(CH₂)₂CH=CH2 |
| 619. | H | 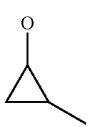 | Cl |
| 620. | H | O(CH₂)₂Ph-4-CN | Cl |
| 621. | H | Cl | O(CH₂)₂Ph-4-CN |
| 622. | H | OCH₂CH₂CH₃ | Cl |
| 623. | H | O(CH₂)₂O(CH₂)₂OCH₃ | Cl |
| 624. | H | CH₃CH₂CH(CH₃)O OCH(CH₃)CH₂CH₃ | Cl |
| 625. | H | OCH₂CH=CH₂ | Cl |
| 626. | H | Cl | OCH₂ CH=CH₂ |
| 627. | H | Cl | OCH₂ C≡CH |
| 628. | H | O(CH₂)₂ C≡CCH₃ | Cl |
| 629. | H | OCH₂ C≡CCH₃ | Cl |
| 630. | H | Cl | OCH₂ C≡CCH₃ |
| 631. | H | OCH(CH₃)-cycloprop. | Cl |
| 632. | H | OCH₂C(CH₃)=CH₂ | Cl |
| 633. | H | Cl | OCH₂C(CH₃)=CH₂ |
| 634. | H |  | Cl |

TABLE B-6-continued
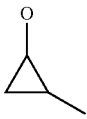
I.6
|  | R₃ | R₆ | R₇ |
|---|---|---|---|
| 635. | H | Cl | 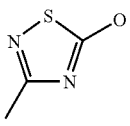 |
| 636. | H | O(CH₂)₂OPh-2-Cl | Cl |
| 637. | H | O—Cl, m-ClPhCH(CH₃)O | Cl |
| 638. | H | O(CH₂)₂SCH₂Ph-4-Cl | Cl |
| 639. | H | O(CH₂)₂Ph-2-Cl | Cl |
| 640. | H | O(CH₂)₂Ph-3-CF₃ | Cl |
| 641. | H | O(CH₂)₂Ph-4-CH₃ | Cl |
| 642. | H | 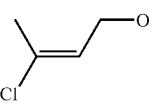 | Cl |
| 643. | H | 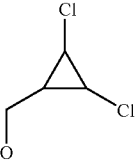 | Cl |
| 644. | H | O (CH₂)₂ CF₃ | Cl |
| 645. | H | 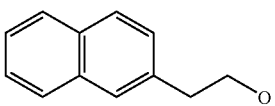 | Cl |
| 646. | H | O (CH₂)₁₁C(O)OCH₃ | Cl |
| 647. | H |  | Cl |
| 648. | H | O(CH₂)₂SCH₃ | Cl |
| 649. | H | O(CH₂)₇CH₃ | Cl |
| 650. | H | OCH₂Ph-3-OCH₃ | Cl |

TABLE B-6-continued
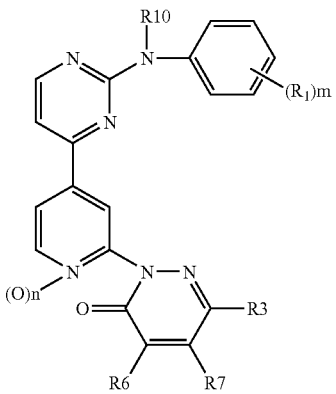
I.6
|   | R3 | R6 | R7 |
|---|---|---|---|
| 651. | H | 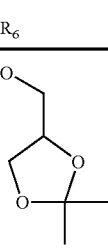 | Cl |
| 652. | H | OC$_{12}$H$_{24}$ | Cl |
| 653. | H | O(CH$_2$)$_2$O(CH$_2$)$_5$CH$_3$ | Cl |
| 654. | H | O C$_{10}$H$_{18}$ | Cl |
| 655. | H | 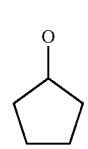 | Cl |
| 656. | H | O(CH$_2$)$_2$SCH$_2$CH$_3$ | Cl |
| 657. | H | 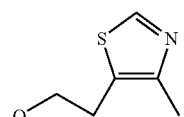 | Cl |
| 658. | H | OCH$_2$CH=CH(CH$_2$)$_2$CH$_3$ | Cl |
| 659. | H | O(CH$_2$)$_2$Ph-3,4-(OCH$_3$)$_2$ | Cl |
| 660. | H | O(CH$_2$)$_2$Ph-4-Cl | Cl |
| 661. | H | CF$_3$(CF$_2$)$_5$CH$_2$O | Cl |
| 662. | H | 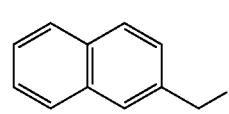 | Cl |
| 663. | H | OCH$_2$Ph-2-I | Cl |
| 664. | H | CH$_3$(CH$_2$)$_2$O(CH$_2$)$_2$O(CH$_2$)$_2$O(CH$_2$)$_2$O | Cl |
| 665. | H | 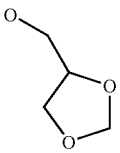 | Cl |
| 666. | H | O(CH$_2$)$_3$-4-(C$_5$H$_4$N) | Cl |

TABLE B-6-continued
I.6
| | R₃ | R₆ | R₇ |
|---|---|---|---|
| 667. | H | 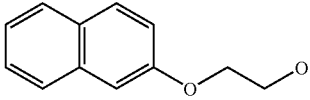 | Cl |
| 668. | H | 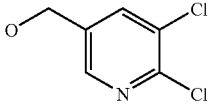 | Cl |
| 669. | H | O(CH₂)₁₁Br | Cl |
| 670. | H | O(CH₂)₂S Ph | Cl |
| 671. | H | 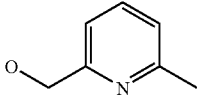 | Cl |
| 672. | H | 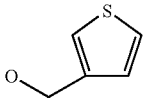 | Cl |
| 673. | H | O(CH₂)₆Ph | Cl |
| 674. | H | 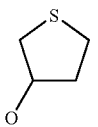 | Cl |
| 675. | H | O(CH₂)₉CH=CH₂ | Cl |
| 676. | H | 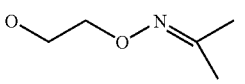 | Cl |
| 677. | H |  | Cl |
| 678. | H | OCH₂Ph-3-CF₃ | Cl |
| 679. | H | OCH₂-3-(C₅H₄N) | Cl |
| 680. | H | OCH₂Si(CH₃)₃ | Cl |
| 681. | H | O(CH₂)₄Cl | Cl |

TABLE B-6-continued

I.6

[Structure showing a pyrimidine with R10-N-phenyl-(R1)m substituent, connected to a pyridine N-oxide (O)n, linked to a pyridazinone with R3, R6, R7 substituents]

| | R₃ | R₆ | R₇ |
|---|---|---|---|
| 682. | H | [4-bromophenyl-substituted dioxolanone with CH₂O- linker] | Cl |
| 683. | H | [4-CF₃-benzyl-O-phenyl-O-phenyl-O-CH₂CH₂-O- group] | Cl |
| 684. | H | [2-nitrophenyl-S-CH₂CH₂-O- group] | Cl |
| 685. | H | SEt | SEt |
| 686. | H | Cl | OiPr |
| 687. | H | Cl | NH₂ |
| 688. | H | Cl | N(CH₃)NH₂ |
| 689. | H | [morpholinyl] | [morpholinyl] |
| 690. | H | Cl | NHPr |
| 691. | H | Cl | NHPh |
| 692. | H | Cl | NHCH(CH₂)₂ |
| 693. | H | NHPr | Cl |
| 694. | H | NHCH(CH₂)₂ | Cl |
| 695. | H | Cl | NH C₅H₉ |
| 696. | H | NH C₅H₉ | Cl |
| 697. | H | Cl | [valine methyl ester NH- group] |

TABLE B-6-continued

I.6

| | $R_3$ | $R_6$ | $R_7$ |
|---|---|---|---|
| 698. | H | Cl | N(CH$_3$)(OCH$_3$) |
| 699. | H | Cl | NHCH$_2$C≡CH |
| 700. | H | Cl | NHCH(CH$_3$)CH$_2$OCH$_3$ |
| 701. | H | Cl | NHEt |
| 702. | H | NHCH$_2$C≡CH | Cl |
| 703. | H | NHEt | Cl |
| 704. | H | Br | Br |
| 705. | H | iPr | Br |
| 706. | H | OBu | Ph |
| 707. | H | Ph-3,5-(CF$_3$)$_2$ | Ph-3,5-(CF$_3$)$_2$ |
| 708. | H | Ph-4-CH$_3$ | Ph-4-CH$_3$ |
| 709. | H | OiPr | Ph |
| 710. | H | OiPr | Ph-4-CH$_3$ |
| 711. | H | OiPr | Ph-3,5-(CF$_3$)$_2$ |
| 712. | H | OiPr | Ph-4- Si (CH$_3$)$_3$ |
| 713. | H | Ph-4-Si (CH$_3$)$_3$ | Ph-4- Si (CH$_3$)$_3$ |
| 714. | H | OCH$_2$C≡CH | Cl |
| 715. | H | NHCH$_2$Ph | Cl |
| 716. | H | Cl | NHCH$_2$Ph |
| 717. | H | NH$_2$ | Cl |
| 718. | H | 1,3-dioxan-5-yloxy | Cl |
| 719. | H | (tetrahydrofuran-2-yl)methoxy | Cl |
| 720. | H | oxetan-3-yloxy | Cl |
| 721. | H | Cl | 1,3-dioxan-5-yloxy |
| 722. | H | Cl | (tetrahydrofuran-2-yl)methoxy |
| 723. | H | OiPr | Cl |

TABLE B-6-continued

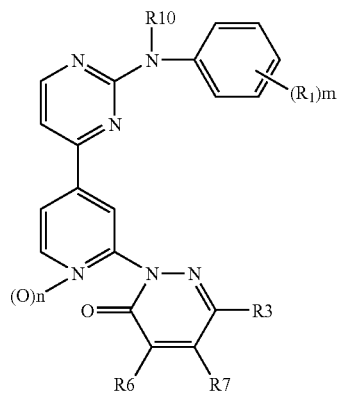

I.6

| | R₃ | R₆ | R₇ |
|---|---|---|---|
| 724. | H | OEt | Cl |
| 725. | H | NHCH(CH₃)CH₂OCH₃ | Cl |
| 726. | H | SCH₂CH₃ | Cl |

TABLE B-7

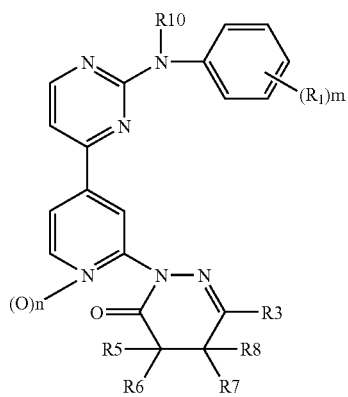

I.7

TABLE B-7-continued

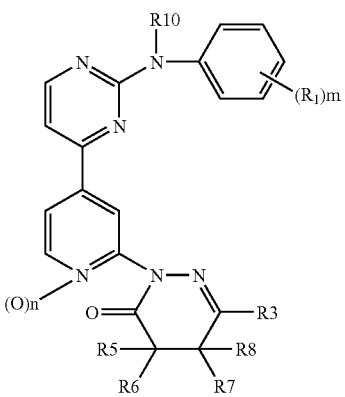

I.7

| N° | R₃ | R₅ | R₆ | R₇ | R₈ |
|---|---|---|---|---|---|
| 1. | H | H | H | H | H |
| 2. | H | CH₃ | H | H | H |
| 3. | H | nBu | H | H | H |
| 4. | H | CF₃ | H | H | H |
| 5. | H | CF₂CF₃ | H | H | H |
| 6. | H | CH₂OCH₃ | H | H | H |
| 7. | H | OCH₃ | H | H | H |
| 8. | H | Ph | H | H | H |
| 9. | H | —CH₂Ph | H | H | H |
| 10. | H | H | H | CH₃ | H |
| 11. | H | H | H | nBu | H |
| 12. | H | H | H | CF₃ | H |
| 13. | H | H | H | CF₂CF₃ | H |
| 14. | H | H | H | CH₂OCH₃ | H |
| 15. | H | H | H | OCH₃ | H |
| 16. | H | H | H | Ph | H |
| 17. | H | H | H | —CH₂Ph | H |
| 18. | H | CH₃ | CH₃ | H | H |
| 19. | H | nBu | CH₃ | H | H |
| 20. | H | CF₃ | CH₃ | H | H |
| 21. | H | CF₂CF₃ | CH₃ | H | H |
| 22. | H | CH₂OCH₃ | CH₃ | H | H |
| 23. | H | OCH₃ | CH₃ | H | H |
| 24. | H | Ph | CH₃ | H | H |
| 25. | H | —CH₂Ph | CH₃ | H | H |
| 26. | H | H | H | CH₃ | CH₃ |
| 27. | H | H | H | CH₃ | nBu |
| 28. | H | H | H | CH₃ | CF₃ |
| 29. | H | H | H | CH₃ | CF₂CF₃ |
| 30. | H | H | H | CH₃ | CH₂OCH₃ |
| 31. | H | H | H | CH₃ | OCH₃ |
| 32. | H | H | H | CH₃ | Ph |
| 33. | H | H | H | CH₃ | —CH₂Ph |
| 34. | H | CH₃ | H | H | CH₃ |
| 35. | H | nBu | H | H | CH₃ |
| 36. | H | CF₃ | H | H | CH₃ |
| 37. | H | CF₂CF₃ | H | H | CH₃ |
| 38. | H | CH₂OCH₃ | H | H | CH₃ |
| 39. | H | OCH₃ | H | H | CH₃ |
| 40. | H | Ph | H | H | CH₃ |
| 41. | H | —CH₂Ph | H | H | CH₃ |
| 42. | H | H | CH₃ | nBu | H |
| 43. | H | H | CH₃ | CF₃ | H |
| 44. | H | H | CH₃ | CF₂CF₃ | H |
| 45. | H | H | CH₃ | CH₂OCH₃ | H |
| 46. | H | H | CH₃ | OCH₃ | H |
| 47. | H | H | CH₃ | Ph | H |
| 48. | H | H | CH₃ | —CH₂Ph | H |
| 49. | H | CH₃ | H | CH₃ | CH₃ |
| 50. | H | nBu | H | CH₃ | CH₃ |

TABLE B-7-continued

I.7

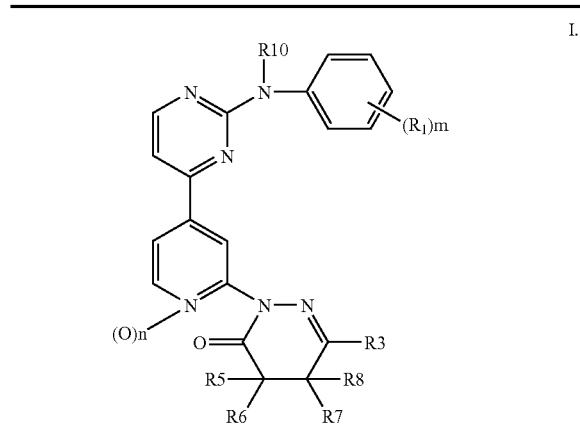

| N° | R₃ | R₅ | R₆ | R₇ | R₈ |
|---|---|---|---|---|---|
| 51. | H | CF₃ | H | CH₃ | CH₃ |
| 52. | H | CF₂CF₃ | H | CH₃ | CH₃ |
| 53. | H | CH₂OCH₃ | H | CH₃ | CH₃ |
| 54. | H | OCH₃ | H | CH₃ | CH₃ |
| 55. | H | Ph | H | CH₃ | CH₃ |
| 56. | H | —CH₂Ph | H | CH₃ | CH₃ |
| 57. | H | CH₃ | CH₃ | CH₃ | H |
| 58. | H | CH₃ | CH₃ | nBu | H |
| 59. | H | CH₃ | CH₃ | CF₃ | H |
| 60. | H | CH₃ | CH₃ | CF₂CF₃ | H |
| 61. | H | CH₃ | CH₃ | CH₂OCH₃ | H |
| 62. | H | CH₃ | CH₃ | OCH₃ | H |
| 63. | H | CH₃ | CH₃ | Ph | H |
| 64. | H | CH₃ | CH₃ | —CH₂Ph | H |
| 65. | H | nBu | CH₃ | CH₃ | H |
| 66. | H | CF₃ | CH₃ | CH₃ | H |
| 67. | H | CF₂CF₃ | CH₃ | CH₃ | H |
| 68. | H | CH₂OCH₃ | CH₃ | CH₃ | H |
| 69. | H | OCH₃ | CH₃ | CH₃ | H |
| 70. | H | Ph | CH₃ | CH₃ | H |
| 71. | H | —CH₂Ph | CH₃ | CH₃ | H |
| 72. | H | CH₃ | H | CH₃ | nBu |
| 73. | H | CH₃ | H | CH₃ | CF₃ |
| 74. | H | CH₃ | H | CH₃ | CF₂CF₃ |
| 75. | H | CH₃ | H | CH₃ | CH₂OCH₃ |
| 76. | H | CH₃ | H | CH₃ | OCH₃ |
| 77. | H | CH₃ | H | CH₃ | Ph |
| 78. | H | CH₃ | H | CH₃ | —CH₂Ph |
| 79. | H | CH₃ | CH₃ | CH₃ | CH₃ |
| 80. | H | nBu | CH₃ | CH₃ | CH₃ |
| 81. | H | CF₃ | CH₃ | CH₃ | CH₃ |
| 82. | H | CF₂CF₃ | CH₃ | CH₃ | CH₃ |
| 83. | H | CH₂OCH₃ | CH₃ | CH₃ | CH₃ |
| 84. | H | OCH₃ | CH₃ | CH₃ | CH₃ |
| 85. | H | Ph | CH₃ | CH₃ | CH₃ |
| 86. | H | —CH₂Ph | CH₃ | CH₃ | CH₃ |
| 87. | H | CH₃ | CH₃ | CH₃ | nBu |
| 88. | H | CH₃ | CH₃ | CH₃ | CF₃ |
| 89. | H | CH₃ | CH₃ | CH₃ | CF₂CF₃ |
| 90. | H | CH₃ | CH₃ | CH₃ | CH₂OCH₃ |
| 91. | H | CH₃ | CH₃ | CH₃ | OCH₃ |
| 92. | H | CH₃ | CH₃ | CH₃ | Ph |
| 93. | H | CH₃ | CH₃ | CH₃ | —CH₂Ph |
| 94. | H | nBnu | nBu | H | H |
| 95. | H | CF₃ | nBu | H | H |
| 96. | H | CF₂CF₃ | nBu | H | H |
| 97. | H | CH₂OCH₃ | nBu | H | H |
| 98. | H | OCH₃ | nBu | H | H |
| 99. | H | Ph | nBu | H | H |
| 100. | H | —CH₂Ph | nBu | H | H |
| 101. | H | H | H | Bu | nBu |
| 102. | H | H | H | CF₃ | nBu |
| 103. | H | H | H | CF₂CF₃ | nBu |
| 104. | H | H | H | CH₂OCH₃ | nBu |
| 105. | H | H | H | OCH₃ | nBu |
| 106. | H | H | H | Ph | nBu |
| 107. | H | H | H | —CH₂Ph | nBu |
| 108. | H | nBu | H | H | H |
| 109. | H | nBu | H | H | CH₃ |
| 110. | H | nBu | H | H | nBu |
| 111. | H | nBu | H | H | CF₃ |
| 112. | H | nBu | H | H | CF₂CF₃ |
| 113. | H | nBu | H | H | CH₂OCH₃ |
| 114. | H | nBu | H | H | OCH₃ |
| 115 | H | nBu | H | H | Ph |
| 116. | H | nBu | H | H | —CH₂Ph |
| 117. | H | H | H | nBu | H |
| 118. | H | H | CH₃ | nBu | H |
| 119. | H | H | nBu | nBu | H |
| 120. | H | H | CF₃ | nBu | H |
| 121. | H | H | CF₂CF₃ | nBu | H |
| 122. | H | H | CH₂OCH₃ | nBu | H |
| 123. | H | H | OCH₃ | nBu | H |
| 124. | H | H | Ph | nBu | H |
| 125. | H | H | —CH₂Ph | nBu | H |
| 126. | H | CH₃ | nBu | nBu | H |
| 127. | H | nBu | nBu | nBu | H |
| 128. | H | CF₃ | nBu | nBu | H |
| 129. | H | CF₂CF₃ | nBu | nBu | H |
| 130. | H | CH₂OCH₃ | nBu | nBu | H |
| 131. | H | OCH₃ | nBu | nBu | H |
| 132. | H | Ph | nBu | Bu | H |
| 133. | H | —CH₂Ph | nBu | nBu | H |
| 134. | H | CH₃ | H | nBu | nBu |
| 135. | H | nBu | H | nBu | nBu |
| 136. | H | CF₃ | H | nBu | nBu |
| 137. | H | CF₂CF₃ | H | nBu | nBu |
| 138. | H | CH₂OCH₃ | H | nBu | nBu |
| 139. | H | OCH₃ | H | nBu | nBu |
| 140. | H | Ph | H | nBu | nBu |
| 141. | H | —CH₂Ph | H | nBu | nBu |
| 142. | H | nBu | nBu | CH₃ | H |
| 143. | H | nBu | nBu | CF₃ | H |
| 144. | H | nBu | nBu | CF₂CF₃ | H |
| 145. | H | nBu | nBu | CH₂OCH₃ | H |
| 146. | H | nBu | nBu | OCH₃ | H |
| 147. | H | nBu | nBu | Ph | H |
| 148. | H | nBu | nBu | —CH₂Ph | H |
| 149. | H | nBu | H | CH₃ | nBu |
| 150. | H | nBu | H | CF₃ | nBu |
| 151. | H | nBu | H | CF₂CF₃ | nBu |
| 152. | H | nBu | H | CH₂OCH₃ | nBu |
| 153. | H | nBu | H | OCH₃ | nBu |
| 154. | H | nBu | H | Ph | nBu |
| 155. | H | nBu | H | —CH₂Ph | nBu |
| 156. | H | CH₃ | nBu | nBu | nBu |
| 157. | H | Bu | nBu | nBu | nBu |
| 158. | H | CF₃ | nBu | nBu | nBu |
| 159. | H | CF₂CF₃ | nBu | nBu | nBu |
| 160. | H | CH₂OCH₃ | nBu | nBu | nBu |
| 161. | H | OCH₃ | nBu | nBu | nBu |
| 162. | H | Ph | nBu | nBu | nBu |

TABLE B-7-continued

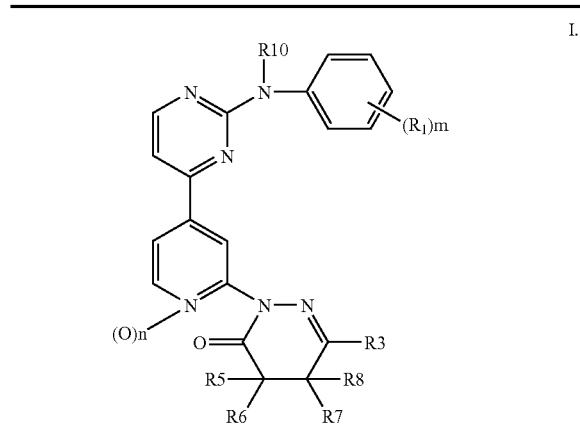

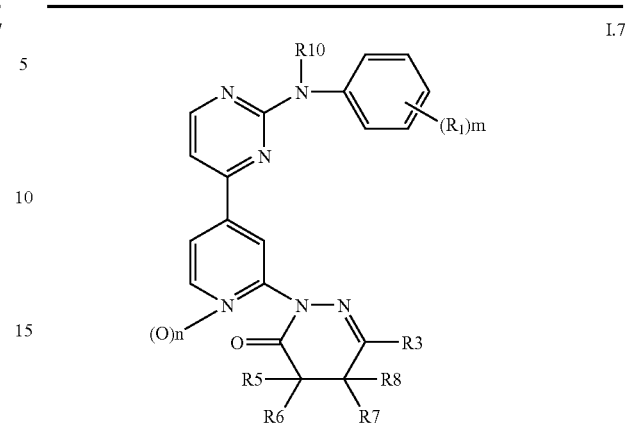

| N° | R3 | R5 | R6 | R7 | R8 |
|---|---|---|---|---|---|
| 163. | H | —CH2Ph | nBu | nBu | nBu |
| 164. | H | nBu | nBu | nBu | CH3 |
| 165. | H | nBu | nBu | nBu | CF3 |
| 166. | H | nBu | nBu | nBu | CF2CF3 |
| 167. | H | nBu | nBu | nBu | CH2OCH3 |
| 168. | H | nBu | nBu | nBu | OCH3 |
| 169. | H | nBu | nBu | nBu | Ph |
| 170. | H | nBu | Bu | nBu | —CH2Ph |
| 171. | H | nBu | CH3 | nBu | CH3 |
| 172. | H | nBu | CH3 | nBu | CF3 |
| 173. | H | nBu | CH3 | nBu | CF2CF3 |
| 174. | H | nBu | CH3 | nBu | CH2OCH3 |
| 175. | H | nBu | CH3 | nBu | OCH3 |
| 176. | H | nBu | CH3 | nBu | Ph |
| 177. | H | nBu | CH3 | nBu | —CH2Ph |
| 178. | H | CF3 | nBu | nBu | CH3 |
| 179. | H | CF2CF3 | nBu | nBu | CH3 |
| 180. | H | CH2OCH3 | nBu | nBu | CH3 |
| 181. | H | OCH3 | nBu | nBu | CH3 |
| 182. | H | Ph | nBu | nBu | CH3 |
| 183. | H | —CH2Ph | nBu | nBu | CH3 |
| 184. | H | CH3 | CH3 | nBu | nBu |
| 185. | H | CF3 | CH3 | nBu | nBu |
| 186. | H | CF2CF3 | CH3 | nBu | nBu |
| 187. | H | CH2OCH3 | CH3 | nBu | nBu |
| 188. | H | OCH3 | CH3 | nBu | nBu |
| 189. | H | Ph | CH3 | nBu | nBu |
| 190. | H | —CH2Ph | CH3 | nBu | nBu |
| 191. | H | nBu | nBu | CH3 | CH3 |
| 192. | H | nBu | nBu | CF3 | CH3 |
| 193. | H | nBu | nBu | CF2CF3 | CH3 |
| 194. | H | nBu | nBu | CH2OCH3 | CH3 |
| 195. | H | nBu | nBu | OCH3 | CH3 |
| 196. | H | nBu | nBu | Ph | CH3 |
| 197. | H | nBu | nBu | —CH2Ph | CH3 |
| 198. | H | nBu | CH3 | CH3 | CF3 |
| 199. | H | nBu | CH3 | CH3 | CF2CF3 |
| 200. | H | nBu | CH3 | CH3 | CH2OCH3 |
| 201. | H | nBu | CH3 | CH3 | OCH3 |
| 202. | H | nBu | CH3 | CH3 | Ph |
| 203. | H | nBu | CH3 | CH3 | —CH2Ph |
| 204. | H | CF3 | CH3 | CH3 | nBu |
| 205. | H | CF2CF3 | CH3 | CH3 | nBu |
| 206. | H | CH2OCH3 | CH3 | CH3 | nBu |
| 207. | H | OCH3 | CH3 | CH3 | nBu |
| 208. | H | Ph | CH3 | CH3 | nBu |
| 209. | H | —CH2Ph | CH3 | CH3 | nBu |
| 210. | H | CF3 | nBu | CH3 | CH3 |
| 211. | H | CF2CF3 | nBu | CH3 | CH3 |
| 212. | H | CH2OCH3 | nBu | CH3 | CH3 |
| 213. | H | OCH3 | nBu | CH3 | CH3 |
| 214. | H | Ph | nBu | CH3 | CH3 |
| 215. | H | —CH2Ph | nBu | CH3 | CH3 |
| 216. | H | CH3 | CH3 | CF3 | nBu |
| 217. | H | CH3 | CH3 | CF2CF3 | nBu |
| 218. | H | CH3 | CH3 | CH2OCH3 | nBu |
| 219. | H | CH3 | CH3 | OCH3 | nBu |
| 220. | H | CH3 | CH3 | Ph | nBu |
| 221. | H | CH3 | CH3 | —CH2Ph | nBu |
| 222. | H | CF3 | nBu | H | CH3 |
| 223. | H | CF2CF3 | nBu | H | CH3 |
| 224. | H | CH2OCH3 | nBu | H | CH3 |
| 225. | H | OCH3 | nBu | H | CH3 |
| 226. | H | Ph | nBu | H | CH3 |
| 227. | H | —CH2Ph | nBu | H | CH3 |
| 228. | H | H | CH3 | CF3 | nBu |
| 229. | H | H | CH3 | CF2CF3 | nBu |
| 230. | H | H | CH3 | CH2OCH3 | nBu |
| 231. | H | H | CH3 | OCH3 | nBu |
| 232. | H | H | CH3 | Ph | nBu |
| 233. | H | H | CH3 | —CH2Ph | nBu |
| 234. | H | nBu | H | CH3 | CF3 |
| 235. | H | nBu | H | CH3 | CF2CF3 |
| 236. | H | nBu | H | CH3 | CH2OCH3 |
| 237. | H | nBu | H | CH3 | OCH3 |
| 238. | H | nBu | H | CH3 | Ph |
| 239. | H | nBu | H | CH3 | —CH2Ph |
| 240. | H | CF3 | CH3 | nBu | H |
| 241. | H | CF2CF3 | CH3 | nBu | H |
| 242. | H | CH2OCH3 | CH3 | nBu | H |
| 243. | H | OCH3 | CH3 | nBu | H |
| 244. | H | Ph | CH3 | nBu | H |
| 245. | H | —CH2Ph | CH3 | nBu | H |
| 246. | H | CF3 | Bu | CH3 | H |
| 247. | H | CF2CF3 | Bu | CH3 | H |
| 248. | H | CH2OCH3 | Bu | CH3 | H |
| 249. | H | OCH3 | Bu | CH3 | H |
| 250. | H | Ph | Bu | CH3 | H |
| 251. | H | —CH2Ph | Bu | CH3 | H |
| 252. | H | CH3 | H | CF3 | nBu |
| 253. | H | CH3 | H | CF2CF3 | nBu |
| 254. | H | CH3 | H | CH2OCH3 | nBu |
| 255. | H | CH3 | H | OCH3 | nBu |
| 256. | H | CH3 | H | Ph | nBu |
| 257. | H | CH3 | H | —CH2Ph | nBu |
| 258. | H | nBu | CH3 | H | CF3 |
| 259. | H | nBu | CH3 | H | CF2CF3 |
| 260. | H | nBu | CH3 | H | CH2OCH3 |
| 261. | H | nBu | CH3 | H | OCH3 |
| 262. | H | nBu | CH3 | H | Ph |
| 263. | H | nBu | CH3 | H | —CH2Ph |
| 264. | H | CF3 | H | CH3 | nBu |
| 265. | H | CF2CF3 | H | CH3 | nBu |
| 266. | H | CH2OCH3 | H | CH3 | nBu |
| 267. | H | OCH3 | H | CH3 | nBu |
| 268. | H | Ph | H | CH3 | nBu |
| 269. | H | —CH2Ph | H | CH3 | nBu |
| 270. | CH3 | H | H | H | H |
| 271. | CH3 | CH3 | H | H | H |
| 272. | CH3 | nBu | H | H | H |
| 273. | CH3 | CF3 | H | H | H |
| 274. | CH3 | CF2CF3 | H | H | H |

TABLE B-7-continued

I.7

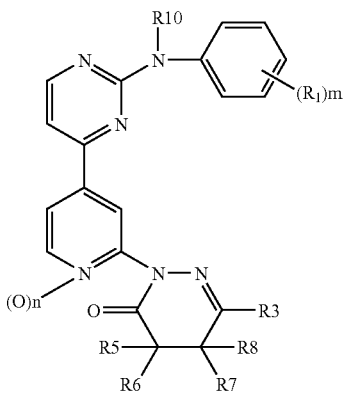

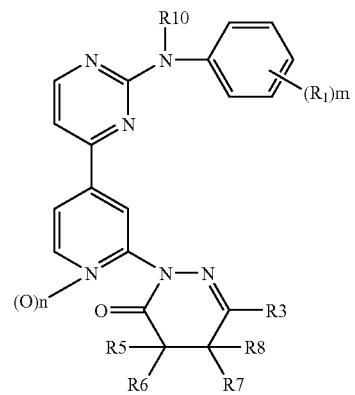

| N° | R₃ | R₅ | R₆ | R₇ | R₈ |
|---|---|---|---|---|---|
| 275. | CH₃ | CH₂OCH₃ | H | H | H |
| 276. | CH₃ | OCH₃ | H | H | H |
| 277. | CH₃ | Ph | H | H | H |
| 278. | CH₃ | —CH₂Ph | H | H | H |
| 279. | CH₃ | H | H | CH₃ | H |
| 280. | CH₃ | H | H | nBu | H |
| 281. | CH₃ | H | H | CF₃ | H |
| 282. | CH₃ | H | H | CF₂CF₃ | H |
| 283. | CH₃ | H | H | CH₂OCH₃ | H |
| 284. | CH₃ | H | H | OCH₃ | H |
| 285. | CH₃ | H | H | Ph | H |
| 286. | CH₃ | H | H | —CH₂Ph | H |
| 287. | CH₃ | CH₃ | CH₃ | H | H |
| 288. | CH₃ | nBu | CH₃ | H | H |
| 289. | CH₃ | CF₃ | CH₃ | H | H |
| 290. | CH₃ | CF₂CF₃ | CH₃ | H | H |
| 291. | CH₃ | CH₂OCH₃ | CH₃ | H | H |
| 292. | CH₃ | OCH₃ | CH₃ | H | H |
| 293. | CH₃ | Ph | CH₃ | H | H |
| 294. | CH₃ | —CH₂Ph | CH₃ | H | H |
| 295. | CH₃ | H | H | CH₃ | CH₃ |
| 296. | CH₃ | H | H | CH₃ | nBu |
| 297. | CH₃ | H | H | CH₃ | CF₃ |
| 298. | CH₃ | H | H | CH₃ | CF₂CF₃ |
| 299. | CH₃ | H | H | CH₃ | CH₂OCH₃ |
| 300. | CH₃ | H | H | CH₃ | OCH₃ |
| 301. | CH₃ | H | H | CH₃ | Ph |
| 302. | CH₃ | H | H | CH₃ | —CH₂Ph |
| 303. | CH₃ | CH₃ | H | H | CH₃ |
| 304. | CH₃ | Bu | H | H | CH₃ |
| 305. | CH₃ | CF₃ | H | H | CH₃ |
| 306. | CH₃ | CF₂CF₃ | H | H | CH₃ |
| 307. | CH₃ | CH₂OCH₃ | H | H | CH₃ |
| 308. | CH₃ | OCH₃ | H | H | CH₃ |
| 309. | CH₃ | Ph | H | H | CH₃ |
| 310. | CH₃ | —CH₂Ph | H | H | CH₃ |
| 311. | CH₃ | H | CH₃ | nBu | H |
| 312. | CH₃ | H | CH₃ | CF₃ | H |
| 313. | CH₃ | H | CH₃ | CF₂CF₃ | H |
| 314. | CH₃ | H | CH₃ | CH₂OCH₃ | H |
| 315. | CH₃ | H | CH₃ | OCH₃ | H |
| 316. | CH₃ | H | CH₃ | Ph | H |
| 317. | CH₃ | H | CH₃ | —CH₂Ph | H |
| 318. | CH₃ | CH₃ | H | CH₃ | CH₃ |
| 319. | CH₃ | nBu | H | CH₃ | CH₃ |
| 320. | CH₃ | CF₃ | H | CH₃ | CH₃ |
| 321. | CH₃ | CF₂CF₃ | H | CH₃ | CH₃ |
| 322. | CH₃ | CH₂OCH₃ | H | CH₃ | CH₃ |
| 323. | CH₃ | OCH₃ | H | CH₃ | CH₃ |
| 324. | CH₃ | Ph | H | CH₃ | CH₃ |
| 325. | CH₃ | —CH₂Ph | H | CH₃ | CH₃ |
| 326. | CH₃ | CH₃ | CH₃ | CH₃ | H |
| 327. | CH₃ | CH₃ | CH₃ | nBu | H |
| 328. | CH₃ | CH₃ | CH₃ | CF₃ | H |
| 329. | CH₃ | CH₃ | CH₃ | CF₂CF₃ | H |
| 330. | CH₃ | CH₃ | CH₃ | CH₂OCH₃ | H |
| 331. | CH₃ | CH₃ | CH₃ | OCH₃ | H |
| 332. | CH₃ | CH₃ | CH₃ | Ph | H |
| 333. | CH₃ | CH₃ | CH₃ | —CH₂Ph | H |
| 334. | CH₃ | nBu | CH₃ | CH₃ | H |
| 335. | CH₃ | CF₃ | CH₃ | CH₃ | H |
| 336. | CH₃ | CF₂CF₃ | CH₃ | CH₃ | H |
| 337. | CH₃ | CH₂OCH₃ | CH₃ | CH₃ | H |
| 338. | CH₃ | OCH₃ | CH₃ | CH₃ | H |
| 339. | CH₃ | Ph | CH₃ | CH₃ | H |
| 340. | CH₃ | —CH₂Ph | CH₃ | CH₃ | H |
| 341. | CH₃ | CH₃ | H | CH₃ | nBu |
| 342. | CH₃ | CH₃ | H | CH₃ | CF₃ |
| 343. | CH₃ | CH₃ | H | CH₃ | CF₂CF₃ |
| 344. | CH₃ | CH₃ | H | CH₃ | CH₂OCH₃ |
| 345. | CH₃ | CH₃ | H | CH₃ | OCH₃ |
| 346. | CH₃ | CH₃ | H | CH₃ | Ph |
| 347. | CH₃ | CH₃ | H | CH₃ | —CH₂Ph |
| 348. | CH₃ | CH₃ | CH₃ | CH₃ | CH₃ |
| 349. | CH₃ | nBu | CH₃ | CH₃ | CH₃ |
| 350. | CH₃ | CF₃ | CH₃ | CH₃ | CH₃ |
| 351. | CH₃ | CF₂CF₃ | CH₃ | CH₃ | CH₃ |
| 352. | CH₃ | CH₂OCH₃ | CH₃ | CH₃ | CH₃ |
| 353. | CH₃ | OCH₃ | CH₃ | CH₃ | CH₃ |
| 354. | CH₃ | Ph | CH₃ | CH₃ | CH₃ |
| 355. | CH₃ | —CH₂Ph | CH₃ | CH₃ | CH₃ |
| 356. | CH₃ | CH₃ | CH₃ | CH₃ | nBu |
| 357. | CH₃ | CH₃ | CH₃ | CH₃ | CF₃ |
| 358. | CH₃ | CH₃ | CH₃ | CH₃ | CF₂CF₃ |
| 359. | CH₃ | CH₃ | CH₃ | CH₃ | CH₂OCH₃ |
| 360. | CH₃ | CH₃ | CH₃ | CH₃ | OCH₃ |
| 361. | CH₃ | CH₃ | CH₃ | CH₃ | Ph |
| 362. | CH₃ | CH₃ | CH₃ | CH₃ | —CH₂Ph |
| 363. | CH₃ | nBu | nBu | H | H |
| 364. | CH₃ | CF₃ | nBu | H | H |
| 365. | CH₃ | CF₂CF₃ | nBu | H | H |
| 366. | CH₃ | CH₂OCH₃ | nBu | H | H |
| 367. | CH₃ | OCH₃ | nBu | H | H |
| 368. | CH₃ | Ph | nBu | H | H |
| 369. | CH₃ | —CH₂Ph | nBu | H | H |
| 370. | CH₃ | H | H | nBu | nBu |
| 371. | CH₃ | H | H | CF₃ | nBu |
| 372. | CH₃ | H | H | CF₂CF₃ | nBu |
| 373. | CH₃ | H | H | CH₂OCH₃ | nBu |
| 374. | CH₃ | H | H | OCH₃ | nBu |
| 375. | CH₃ | H | H | Ph | nBu |
| 376. | CH₃ | H | H | —CH₂Ph | nBu |
| 377. | CH₃ | nBu | H | H | H |
| 378. | CH₃ | nBu | H | H | CH₃ |
| 379. | CH₃ | nBu | H | H | nBu |
| 380. | CH₃ | nBu | H | H | CF₃ |
| 381. | CH₃ | nBu | H | H | CF₂CF₃ |
| 382. | CH₃ | nBu | H | H | CH₂OCH₃ |
| 383. | CH₃ | nBu | H | H | OCH₃ |
| 384. | CH₃ | nBu | H | H | Ph |
| 385. | CH₃ | nBu | H | H | —CH₂Ph |
| 386. | CH₃ | H | H | nBu | H |

TABLE B-7-continued

I.7

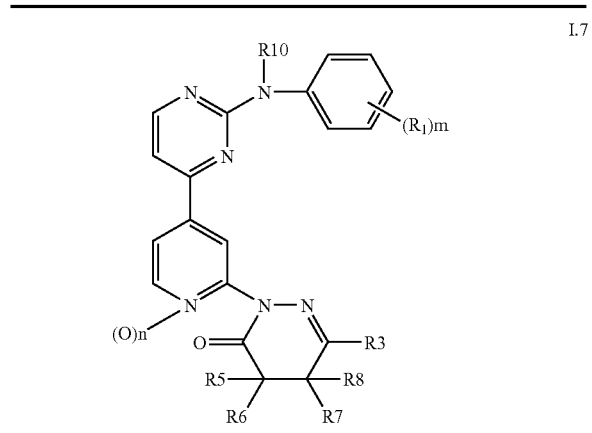

| N° | $R_3$ | $R_5$ | $R_6$ | $R_7$ | $R_8$ |
|---|---|---|---|---|---|
| 387. | $CH_3$ | H | $CH_3$ | nBu | H |
| 388. | $CH_3$ | H | Bu | nBu | H |
| 389. | $CH_3$ | H | $CF_3$ | nBu | H |
| 390. | $CH_3$ | H | $CF_2CF_3$ | nBu | H |
| 391. | $CH_3$ | H | $CH_2OCH_3$ | nBu | H |
| 392. | $CH_3$ | H | $OCH_3$ | nBu | H |
| 393. | $CH_3$ | H | Ph | nBu | H |
| 394. | $CH_3$ | H | —$CH_2Ph$ | nBu | H |
| 395. | $CH_3$ | $CH_3$ | nBu | nBu | H |
| 396. | $CH_3$ | nBu | nBu | nBu | H |
| 397. | $CH_3$ | $CF_3$ | nBu | nBu | H |
| 398. | $CH_3$ | $CF_2CF_3$ | nBu | nBu | H |
| 399. | $CH_3$ | $CH_2OCH_3$ | nBu | nBu | H |
| 400. | $CH_3$ | $OCH_3$ | nBu | nBu | H |
| 401. | $CH_3$ | Ph | nBu | nBu | H |
| 402. | $CH_3$ | —$CH_2Ph$ | nBu | nBu | H |
| 403. | $CH_3$ | $CH_3$ | H | nBu | nBu |
| 404. | $CH_3$ | nBu | H | nBu | nBu |
| 405. | $CH_3$ | $CF_3$ | H | nBu | nBu |
| 406. | $CH_3$ | $CF_2CF_3$ | H | nBu | nBu |
| 407. | $CH_3$ | $CH_2OCH_3$ | H | nBu | nBu |
| 408. | $CH_3$ | $OCH_3$ | H | nBu | nBu |
| 409. | $CH_3$ | Ph | H | nBu | nBu |
| 410. | $CH_3$ | —$CH_2Ph$ | H | nBu | nBu |
| 411. | $CH_3$ | nBu | nBu | $CH_3$ | H |
| 412. | $CH_3$ | nBu | nBu | $CF_3$ | H |
| 413. | $CH_3$ | nBu | nBu | $CF_2CF_3$ | H |
| 414. | $CH_3$ | nBu | nBu | $CH_2OCH_3$ | H |
| 415. | $CH_3$ | nBu | nBu | $OCH_3$ | H |
| 416. | $CH_3$ | nBu | nBu | Ph | H |
| 417. | $CH_3$ | nBu | nBu | —$CH_2Ph$ | H |
| 418. | $CH_3$ | nBu | H | $CH_3$ | nBu |
| 419. | $CH_3$ | nBu | H | $CF_3$ | nBu |
| 420. | $CH_3$ | nBu | H | $CF_2CF_3$ | nBu |
| 421. | $CH_3$ | nBu | H | $CH_2OCH_3$ | nBu |
| 422. | $CH_3$ | nBu | H | $OCH_3$ | nBu |
| 423. | $CH_3$ | nBu | H | Ph | nBu |
| 424. | $CH_3$ | nBu | H | —$CH_2Ph$ | nBu |
| 425. | $CH_3$ | $CH_3$ | nBu | nBu | nBu |
| 426. | $CH_3$ | Bu | nBu | nBu | nBu |
| 427. | $CH_3$ | $CF_3$ | nBu | nBu | nBu |
| 428. | $CH_3$ | $CF_2CF_3$ | nBu | nBu | nBu |
| 429. | $CH_3$ | $CH_2OCH_3$ | nBu | nBu | nBu |
| 430. | $CH_3$ | $OCH_3$ | nBu | nBu | nBu |
| 431. | $CH_3$ | Ph | nBu | nBu | nBu |
| 432. | $CH_3$ | —$CH_2Ph$ | nBu | nBu | nBu |
| 433. | $CH_3$ | nBu | nBu | nBu | $CH_3$ |
| 434. | $CH_3$ | nBu | nBu | nBu | $CF_3$ |
| 435. | $CH_3$ | nBu | nBu | nBu | $CF_2CF_3$ |
| 436. | $CH_3$ | nBu | nBu | nBu | $CH_2OCH_3$ |
| 437. | $CH_3$ | nBu | nBu | nBu | $OCH_3$ |
| 438. | $CH_3$ | nBu | nBu | nBu | Ph |
| 439. | $CH_3$ | nBu | nBu | nBu | —$CH_2Ph$ |
| 440. | $CH_3$ | nBu | $CH_3$ | nBu | $CH_3$ |
| 441. | $CH_3$ | nBu | $CH_3$ | nBu | $CF_3$ |
| 442. | $CH_3$ | nBu | $CH_3$ | nBu | $CF_2CF_3$ |

TABLE B-7-continued

I.7

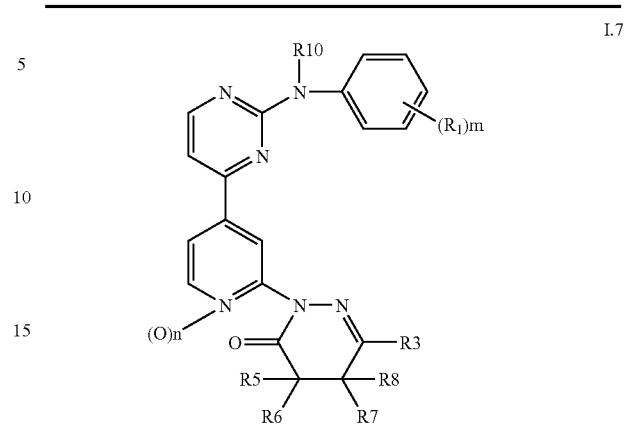

| N° | $R_3$ | $R_5$ | $R_6$ | $R_7$ | $R_8$ |
|---|---|---|---|---|---|
| 443. | $CH_3$ | nBu | $CH_3$ | nBu | $CH_2OCH_3$ |
| 444. | $CH_3$ | nBu | $CH_3$ | nBu | $OCH_3$ |
| 445. | $CH_3$ | nBu | $CH_3$ | nBu | Ph |
| 446. | $CH_3$ | nBu | $CH_3$ | nBu | —$CH_2Ph$ |
| 447. | $CH_3$ | $CF_3$ | nBu | nBu | $CH_3$ |
| 448. | $CH_3$ | $CF_2CF_3$ | nBu | nBu | $CH_3$ |
| 449. | $CH_3$ | $CH_2OCH_3$ | nBu | nBu | $CH_3$ |
| 450. | $CH_3$ | $OCH_3$ | nBu | nBu | $CH_3$ |
| 451. | $CH_3$ | Ph | nBu | nBu | $CH_3$ |
| 452. | $CH_3$ | —$CH_2Ph$ | nBu | nBu | $CH_3$ |
| 453. | $CH_3$ | $CH_3$ | $CH_3$ | nBu | nBu |
| 454. | $CH_3$ | $CF_3$ | $CH_3$ | nBu | nBu |
| 455. | $CH_3$ | $CF_2CF_3$ | $CH_3$ | nBu | nBu |
| 456. | $CH_3$ | $CH_2OCH_3$ | $CH_3$ | nBu | nBu |
| 457. | $CH_3$ | $OCH_3$ | $CH_3$ | nBu | nBu |
| 458. | $CH_3$ | Ph | $CH_3$ | nBu | nBu |
| 459. | $CH_3$ | —$CH_2Ph$ | $CH_3$ | nBu | nBu |
| 460. | $CH_3$ | nBu | nBu | $CH_3$ | $CH_3$ |
| 461. | $CH_3$ | nBu | nBu | $CH_3$ | $CF_3$ |
| 462. | $CH_3$ | nBu | nBu | $CH_3$ | $CF_2CF_3$ |
| 463. | $CH_3$ | nBu | nBu | $CH_3$ | $CH_2OCH_3$ |
| 464. | $CH_3$ | nBu | nBu | $CH_3$ | $OCH_3$ |
| 465. | $CH_3$ | nBu | nBu | $CH_3$ | Ph |
| 466. | $CH_3$ | nBu | nBu | $CH_3$ | —$CH_2Ph$ |
| 467. | $CH_3$ | nBu | $CH_3$ | $CH_3$ | $CF_3$ |
| 468. | $CH_3$ | nBu | $CH_3$ | $CH_3$ | $CF_2CF_3$ |
| 469. | $CH_3$ | nBu | $CH_3$ | $CH_3$ | $CH_2OCH_3$ |
| 470. | $CH_3$ | nBu | $CH_3$ | $CH_3$ | $OCH_3$ |
| 471. | $CH_3$ | nBu | $CH_3$ | $CH_3$ | Ph |
| 472. | $CH_3$ | nBu | $CH_3$ | $CH_3$ | —$CH_2Ph$ |
| 473. | $CH_3$ | $CF_3$ | $CH_3$ | $CH_3$ | nBu |
| 474. | $CH_3$ | $CF_2CF_3$ | $CH_3$ | $CH_3$ | nBu |
| 475. | $CH_3$ | $CH_2OCH_3$ | $CH_3$ | $CH_3$ | nBu |
| 476. | $CH_3$ | $OCH_3$ | $CH_3$ | $CH_3$ | nBu |
| 477. | $CH_3$ | Ph | $CH_3$ | $CH_3$ | nBu |
| 478. | $CH_3$ | —$CH_2Ph$ | $CH_3$ | $CH_3$ | nBu |
| 479. | $CH_3$ | $CF_3$ | nBu | $CH_3$ | $CH_3$ |
| 480. | $CH_3$ | $CF_2CF_3$ | nBu | $CH_3$ | $CH_3$ |
| 481. | $CH_3$ | $CH_2OCH_3$ | nBu | $CH_3$ | $CH_3$ |
| 482. | $CH_3$ | $OCH_3$ | nBu | $CH_3$ | $CH_3$ |
| 483. | $CH_3$ | Ph | nBu | $CH_3$ | $CH_3$ |
| 484. | $CH_3$ | —$CH_2Ph$ | nBu | $CH_3$ | $CH_3$ |
| 485. | $CH_3$ | $CH_3$ | $CH_3$ | $CF_3$ | nBu |
| 486. | $CH_3$ | $CH_3$ | $CH_3$ | $CF_2CF_3$ | nBu |
| 487. | $CH_3$ | $CH_3$ | $CH_3$ | $CH_2OCH_3$ | nBu |
| 488. | $CH_3$ | $CH_3$ | $CH_3$ | $OCH_3$ | nBu |
| 489. | $CH_3$ | $CH_3$ | $CH_3$ | Ph | nBu |
| 490. | $CH_3$ | $CH_3$ | $CH_3$ | —$CH_2Ph$ | nBu |
| 491. | $CH_3$ | $CF_3$ | nBu | H | $CH_3$ |
| 492. | $CH_3$ | $CF_2CF_3$ | nBu | H | $CH_3$ |
| 493. | $CH_3$ | $CH_2OCH_3$ | nBu | H | $CH_3$ |
| 494. | $CH_3$ | $OCH_3$ | nBu | H | $CH_3$ |
| 495. | $CH_3$ | Ph | nBu | H | $CH_3$ |
| 496. | $CH_3$ | —$CH_2Ph$ | nBu | H | $CH_3$ |
| 497. | $CH_3$ | H | $CH_3$ | $CF_3$ | nBu |
| 498. | $CH_3$ | H | $CH_3$ | $CF_2CF_3$ | nBu |

TABLE B-7-continued

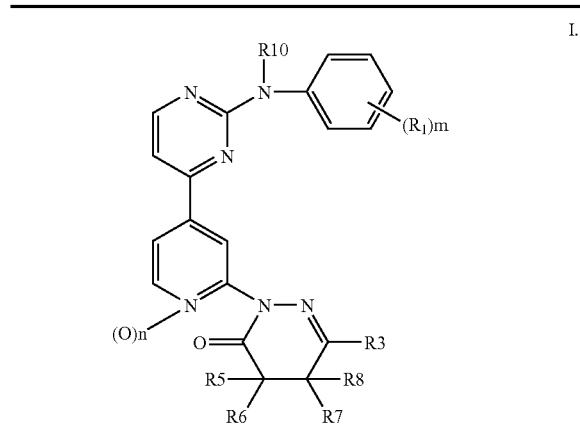

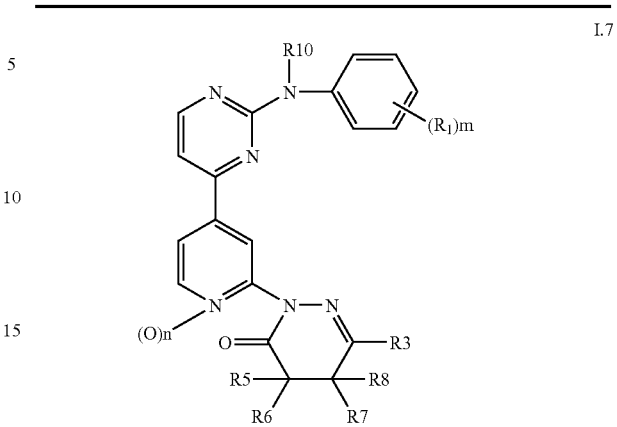

| N° | R3 | R5 | R6 | R7 | R8 |
|---|---|---|---|---|---|
| 499. | CH3 | H | CH3 | CH2OCH3 | nBu |
| 500. | CH3 | H | CH3 | OCH3 | nBu |
| 501. | CH3 | H | CH3 | Ph | nBu |
| 502. | CH3 | H | CH3 | —CH2Ph | nBu |
| 503. | CH3 | nBu | H | CH3 | CF3 |
| 504. | CH3 | nBu | H | CH3 | CF2CF3 |
| 505. | CH3 | nBu | H | CH3 | CH2OCH3 |
| 506. | CH3 | nBu | H | CH3 | OCH3 |
| 507. | CH3 | nBu | H | CH3 | Ph |
| 508. | CH3 | nBu | H | CH3 | —CH2Ph |
| 509. | CH3 | CF3 | CH3 | nBu | H |
| 510. | CH3 | CF2CF3 | CH3 | nBu | H |
| 511. | CH3 | CH2OCH3 | CH3 | nBu | H |
| 512. | CH3 | OCH3 | CH3 | nBu | H |
| 513. | CH3 | Ph | CH3 | nBu | H |
| 514. | CH3 | —CH2Ph | CH3 | nBu | H |
| 515. | CH3 | CF3 | nBu | CH3 | H |
| 516. | CH3 | CF2CF3 | nBu | CH3 | H |
| 517. | CH3 | CH2OCH3 | nBu | CH3 | H |
| 518. | CH3 | OCH3 | nBu | CH3 | H |
| 519. | CH3 | Ph | nBu | CH3 | H |
| 520. | CH3 | —CH2Ph | nBu | CH3 | H |
| 521. | CH3 | CH3 | H | CF3 | nBu |
| 522. | CH3 | CH3 | H | CF2CF3 | nBu |
| 523. | CH3 | CH3 | H | CH2OCH3 | nBu |
| 524. | CH3 | CH3 | H | OCH3 | nBu |
| 525. | CH3 | CH3 | H | Ph | nBu |
| 526. | CH3 | CH3 | H | —CH2Ph | nBu |
| 527. | CH3 | nBu | CH3 | H | CF3 |
| 528. | CH3 | nBu | CH3 | H | CF2CF3 |
| 529. | CH3 | nBu | CH3 | H | CH2OCH3 |
| 530. | CH3 | nBu | CH3 | H | OCH3 |
| 531. | CH3 | nBu | CH3 | H | Ph |
| 532. | CH3 | nBu | CH3 | H | —CH2Ph |
| 533. | CH3 | CF3 | H | CH3 | nBu |
| 534. | CH3 | CF2CF3 | H | CH3 | nBu |
| 535. | CH3 | CH2OCH3 | H | CH3 | nBu |
| 536. | CH3 | OCH3 | H | CH3 | nBu |
| 537. | CH3 | Ph | H | CH3 | nBu |
| 538. | CH3 | —CH2Ph | H | CH3 | nBu |
| 539. | CF3 | H | H | H | H |
| 540. | CF3 | CH3 | H | H | H |
| 541. | CF3 | nBu | H | H | H |
| 542. | CF3 | CF3 | H | H | H |
| 543. | CF3 | CF2CF3 | H | H | H |
| 544. | CF3 | CH2OCH3 | H | H | H |
| 545. | CF3 | OCH3 | H | H | H |
| 546. | CF3 | Ph | H | H | H |
| 547. | CF3 | —CH2Ph | H | H | H |
| 548. | CF3 | H | H | CH3 | H |
| 549. | CF3 | H | H | nBu | H |
| 550. | CF3 | H | H | CF3 | H |
| 551. | CF3 | H | H | CF2CF3 | H |
| 552. | CF3 | H | H | CH2OCH3 | H |
| 553. | CF3 | H | H | OCH3 | H |
| 554. | CF3 | H | H | Ph | H |
| 555. | CF3 | H | H | —CH2Ph | H |
| 556. | CF3 | CH3 | CH3 | H | H |
| 557. | CF3 | nBu | CH3 | H | H |
| 558. | CF3 | CF3 | CH3 | H | H |
| 559. | CF3 | CF2CF3 | CH3 | H | H |
| 560. | CF3 | CH2OCH3 | CH3 | H | H |
| 561. | CF3 | OCH3 | CH3 | H | H |
| 562. | CF3 | Ph | CH3 | H | H |
| 563. | CF3 | —CH2Ph | CH3 | H | H |
| 564. | CF3 | H | H | CH3 | CH3 |
| 565. | CF3 | H | H | CH3 | nBu |
| 566. | CF3 | H | H | CH3 | CF3 |
| 567. | CF3 | H | H | CH3 | CF2CF3 |
| 568. | CF3 | H | H | CH3 | CH2OCH3 |
| 569. | CF3 | H | H | CH3 | OCH3 |
| 570. | CF3 | H | H | CH3 | Ph |
| 571. | CF3 | H | H | CH3 | —CH2Ph |
| 572. | CF3 | CH3 | H | H | CH3 |
| 573. | CF3 | nBu | H | H | CH3 |
| 574. | CF3 | CF3 | H | H | CH3 |
| 575. | CF3 | CF2CF3 | H | H | CH3 |
| 576. | CF3 | CH2OCH3 | H | H | CH3 |
| 577. | CF3 | OCH3 | H | H | CH3 |
| 578. | CF3 | Ph | H | H | CH3 |
| 579. | CF3 | —CH2Ph | H | H | CH3 |
| 580. | CF3 | H | CH3 | nBu | H |
| 581. | CF3 | H | CH3 | CF3 | H |
| 582. | CF3 | H | CH3 | CF2CF3 | H |
| 583. | CF3 | H | CH3 | CH2OCH3 | H |
| 584. | CF3 | H | CH3 | OCH3 | H |
| 585. | CF3 | H | CH3 | Ph | H |
| 586. | CF3 | H | CH3 | —CH2Ph | H |
| 587. | CF3 | CH3 | H | CH3 | CH3 |
| 588. | CF3 | nBu | H | CH3 | CH3 |
| 589. | CF3 | CF3 | H | CH3 | CH3 |
| 590. | CF3 | CF2CF3 | H | CH3 | CH3 |
| 591. | CF3 | CH2OCH3 | H | CH3 | CH3 |
| 592. | CF3 | OCH3 | H | CH3 | CH3 |
| 593. | CF3 | Ph | H | CH3 | CH3 |
| 594. | CF3 | —CH2Ph | H | CH3 | CH3 |
| 595. | CF3 | CH3 | CH3 | CH3 | H |
| 596. | CF3 | CH3 | CH3 | CH3 | nBu |
| 597. | CF3 | CH3 | CH3 | CH3 | CF3 |
| 598. | CF3 | CH3 | CH3 | CH3 | CF2CF3 |
| 599. | CF3 | CH3 | CH3 | CH3 | CH2OCH3 |
| 600. | CF3 | CH3 | CH3 | CH3 | OCH3 |
| 601. | CF3 | CH3 | CH3 | CH3 | Ph |
| 602. | CF3 | CH3 | CH3 | CH3 | —CH2Ph |
| 603. | CF3 | nBu | CH3 | CH3 | H |
| 604. | CF3 | CF3 | CH3 | CH3 | H |
| 605. | CF3 | CF2CF3 | CH3 | CH3 | H |
| 606. | CF3 | CH2OCH3 | CH3 | CH3 | H |
| 607. | CF3 | OCH3 | CH3 | CH3 | H |
| 608. | CF3 | Ph | CH3 | CH3 | H |
| 609. | CF3 | —CH2Ph | CH3 | CH3 | H |
| 610. | CF3 | CH3 | H | CH3 | nBu |

TABLE B-7-continued

I.7

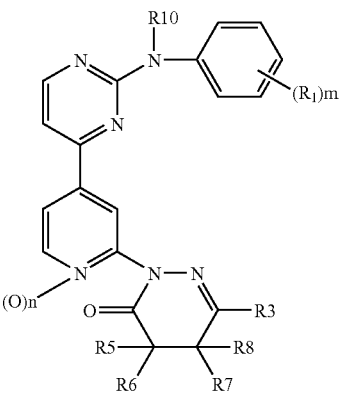

| N° | R₃ | R₅ | R₆ | R₇ | R₈ |
|---|---|---|---|---|---|
| 611. | $CF_3$ | $CH_3$ | H | $CH_3$ | $CF_3$ |
| 612. | $CF_3$ | $CH_3$ | H | $CH_3$ | $CF_2CF_3$ |
| 613. | $CF_3$ | $CH_3$ | H | $CH_3$ | $CH_2OCH_3$ |
| 614. | $CF_3$ | $CH_3$ | H | $CH_3$ | $OCH_3$ |
| 615. | $CF_3$ | $CH_3$ | H | $CH_3$ | Ph |
| 616. | $CF_3$ | $CH_3$ | H | $CH_3$ | —$CH_2Ph$ |
| 617. | $CF_3$ | $CH_3$ | $CH_3$ | $CH_3$ | $CH_3$ |
| 618. | $CF_3$ | nBu | $CH_3$ | $CH_3$ | $CH_3$ |
| 619. | $CF_3$ | $CF_3$ | $CH_3$ | $CH_3$ | $CH_3$ |
| 620. | $CF_3$ | $CF_2CF_3$ | $CH_3$ | $CH_3$ | $CH_3$ |
| 621. | $CF_3$ | $CH_2OCH_3$ | $CH_3$ | $CH_3$ | $CH_3$ |
| 622. | $CF_3$ | $OCH_3$ | $CH_3$ | $CH_3$ | $CH_3$ |
| 623. | $CF_3$ | Ph | $CH_3$ | $CH_3$ | $CH_3$ |
| 624. | $CF_3$ | —$CH_2Ph$ | $CH_3$ | $CH_3$ | $CH_3$ |
| 625. | $CF_3$ | $CH_3$ | $CH_3$ | $CH_3$ | nBu |
| 626. | $CF_3$ | $CH_3$ | $CH_3$ | $CH_3$ | $CF_3$ |
| 627. | $CF_3$ | $CH_3$ | $CH_3$ | $CH_3$ | $CF_2CF_3$ |
| 628. | $CF_3$ | $CH_3$ | $CH_3$ | $CH_3$ | $CH_2OCH_3$ |
| 629. | $CF_3$ | $CH_3$ | $CH_3$ | $CH_3$ | $OCH_3$ |
| 630. | $CF_3$ | $CH_3$ | $CH_3$ | $CH_3$ | Ph |
| 631. | $CF_3$ | $CH_3$ | $CH_3$ | $CH_3$ | —$CH_2Ph$ |
| 632. | $CF_3$ | Bu | nBu | H | H |
| 633. | $CF_3$ | $CF_3$ | nBu | H | H |
| 634. | $CF_3$ | $CF_2CF_3$ | nBu | H | H |
| 635. | $CF_3$ | $CH_2OCH_3$ | nBu | H | H |
| 636. | $CF_3$ | $OCH_3$ | nBu | H | H |
| 637. | $CF_3$ | Ph | nBu | H | H |
| 638. | $CF_3$ | —$CH_2Ph$ | nBu | H | H |
| 639. | $CF_3$ | H | H | nBu | nBu |
| 640. | $CF_3$ | H | H | $CF_3$ | nBu |
| 641. | $CF_3$ | H | H | $CF_2CF_3$ | nBu |
| 642. | $CF_3$ | H | H | $CH_2OCH_3$ | nBu |
| 643. | $CF_3$ | H | H | $OCH_3$ | nBu |
| 644. | $CF_3$ | H | H | Ph | nBu |
| 645. | $CF_3$ | H | H | —$CH_2Ph$ | nBu |
| 646. | $CF_3$ | nBu | H | H | H |
| 647. | $CF_3$ | nBu | H | H | $CH_3$ |
| 648. | $CF_3$ | nBu | H | H | Bu |
| 649. | $CF_3$ | nBu | H | H | $CF_3$ |
| 650. | $CF_3$ | nBu | H | H | $CF_2CF_3$ |
| 651. | $CF_3$ | nBu | H | H | $CH_2OCH_3$ |
| 652. | $CF_3$ | nBu | H | H | $OCH_3$ |
| 653. | $CF_3$ | nBu | H | H | Ph |
| 654. | $CF_3$ | nBu | H | H | —$CH_2Ph$ |
| 655. | $CF_3$ | H | H | nBu | H |
| 656. | $CF_3$ | H | $CH_3$ | nBu | H |
| 657. | $CF_3$ | H | Bu | nBu | H |
| 658. | $CF_3$ | H | $CF_3$ | nBu | H |
| 659. | $CF_3$ | H | $CF_2CF_3$ | nBu | H |
| 660. | $CF_3$ | H | $CH_2OCH_3$ | nBu | H |
| 661. | $CF_3$ | H | $OCH_3$ | nBu | H |
| 662. | $CF_3$ | H | Ph | nBu | H |
| 663. | $CF_3$ | H | —$CH_2Ph$ | nBu | H |
| 664. | $CF_3$ | $CH_3$ | nBu | nBu | H |
| 665. | $CF_3$ | Bu | nBu | nBu | H |
| 666. | $CF_3$ | $CF_3$ | nBu | nBu | H |
| 667. | $CF_3$ | $CF_2CF_3$ | nBu | nBu | H |
| 668. | $CF_3$ | $CH_2OCH_3$ | nBu | nBu | H |
| 669. | $CF_3$ | $OCH_3$ | nBu | nBu | H |
| 670. | $CF_3$ | Ph | nBu | nBu | H |
| 671. | $CF_3$ | —$CH_2Ph$ | nBu | nBu | H |
| 672. | $CF_3$ | $CH_3$ | H | nBu | nBu |
| 673. | $CF_3$ | nBu | H | nBu | nBu |
| 674. | $CF_3$ | $CF_3$ | H | nBu | nBu |
| 675. | $CF_3$ | $CF_2CF_3$ | H | nBu | nBu |
| 676. | $CF_3$ | $CH_2OCH_3$ | H | nBu | nBu |
| 677. | $CF_3$ | $OCH_3$ | H | nBu | nBu |
| 678. | $CF_3$ | Ph | H | nBu | nBu |
| 679. | $CF_3$ | —$CH_2Ph$ | H | nBu | nBu |
| 680. | $CF_3$ | nBu | nBu | $CH_3$ | H |
| 681. | $CF_3$ | nBu | nBu | $CF_3$ | H |
| 682. | $CF_3$ | nBu | nBu | $CF_2CF_3$ | H |
| 683. | $CF_3$ | nBu | nBu | $CH_2OCH_3$ | H |
| 684. | $CF_3$ | nBu | nBu | $OCH_3$ | H |
| 685. | $CF_3$ | nBu | nBu | Ph | H |
| 686. | $CF_3$ | nBu | nBu | —$CH_2Ph$ | H |
| 687. | $CF_3$ | nBu | H | $CH_3$ | nBu |
| 688. | $CF_3$ | nBu | H | $CF_3$ | nBu |
| 689. | $CF_3$ | nBu | H | $CF_2CF_3$ | nBu |
| 690. | $CF_3$ | nBu | H | $CH_2OCH_3$ | nBu |
| 691. | $CF_3$ | nBu | H | $OCH_3$ | nBu |
| 692. | $CF_3$ | nBu | H | Ph | nBu |
| 693. | $CF_3$ | nBu | H | —$CH_2Ph$ | nBu |
| 694. | $CF_3$ | $CH_3$ | nBu | nBu | nBu |
| 695. | $CF_3$ | nBu | nBu | nBu | nBu |
| 696. | $CF_3$ | $CF_3$ | nBu | nBu | nBu |
| 697. | $CF_3$ | $CF_2CF_3$ | nBu | nBu | nBu |
| 698. | $CF_3$ | $CH_2OCH_3$ | nBu | nBu | nBu |
| 699. | $CF_3$ | $OCH_3$ | nBu | nBu | nBu |
| 700. | $CF_3$ | Ph | nBu | nBu | nBu |
| 701. | $CF_3$ | —$CH_2Ph$ | nBu | nBu | nBu |
| 702. | $CF_3$ | nBu | nBu | nBu | $CH_3$ |
| 703. | $CF_3$ | nBu | nBu | nBu | $CF_3$ |
| 704. | $CF_3$ | nBu | nBu | nBu | $CF_2CF_3$ |
| 705. | $CF_3$ | nBu | nBu | nBu | $CH_2OCH_3$ |
| 706. | $CF_3$ | nBu | nBu | nBu | $OCH_3$ |
| 707. | $CF_3$ | nBu | nBu | nBu | Ph |
| 708. | $CF_3$ | nBu | nBu | nBu | —$CH_2Ph$ |
| 709. | $CF_3$ | nBu | $CH_3$ | nBu | $CH_3$ |
| 710. | $CF_3$ | nBu | $CH_3$ | nBu | $CF_3$ |
| 711. | $CF_3$ | nBu | $CH_3$ | nBu | $CF_2CF_3$ |
| 712. | $CF_3$ | nBu | $CH_3$ | nBu | $CH_2OCH_3$ |
| 713. | $CF_3$ | nBu | $CH_3$ | nBu | $OCH_3$ |
| 714. | $CF_3$ | nBu | $CH_3$ | nBu | Ph |
| 715. | $CF_3$ | nBu | $CH_3$ | nBu | —$CH_2Ph$ |
| 716. | $CF_3$ | $CF_3$ | nBu | nBu | $CH_3$ |
| 717. | $CF_3$ | $CF_2CF_3$ | nBu | nBu | $CH_3$ |
| 718. | $CF_3$ | $CH_2OCH_3$ | nBu | nBu | $CH_3$ |
| 719. | $CF_3$ | $OCH_3$ | nBu | nBu | $CH_3$ |
| 720. | $CF_3$ | Ph | nBu | nBu | $CH_3$ |
| 721. | $CF_3$ | —$CH_2Ph$ | nBu | nBu | $CH_3$ |
| 722. | $CF_3$ | $CH_3$ | $CH_3$ | nBu | nBu |

TABLE B-7-continued

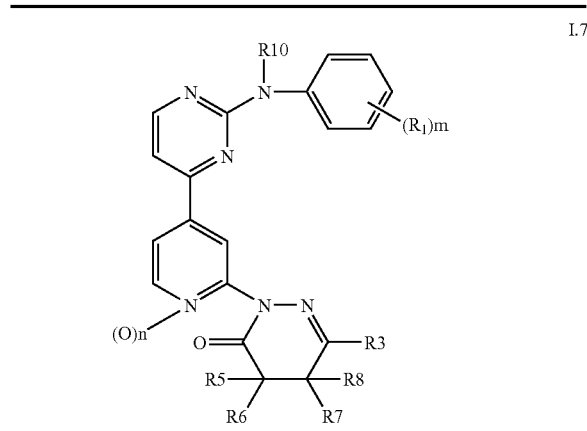

I.7

| N° | $R_3$ | $R_5$ | $R_6$ | $R_7$ | $R_8$ |
|---|---|---|---|---|---|
| 723. | $CF_3$ | $CF_3$ | $CH_3$ | nBu | nBu |
| 724. | $CF_3$ | $CF_2CH_3$ | $CH_3$ | nBu | nBu |
| 725. | $CF_3$ | $CH_2OCH_3$ | $CH_3$ | nBu | nBu |
| 726. | $CF_3$ | $OCH_3$ | $CH_3$ | nBu | nBu |
| 727. | $CF_3$ | Ph | $CH_3$ | nBu | nBu |
| 728. | $CF_3$ | —$CH_2Ph$ | $CH_3$ | nBu | nBu |
| 729. | $CF_3$ | nBu | nBu | $CH_3$ | $CH_3$ |
| 730. | $CF_3$ | nBu | nBu | $CF_3$ | $CH_3$ |
| 731. | $CF_3$ | nBu | nBu | $CF_2CF_3$ | $CH_3$ |
| 732. | $CF_3$ | nBu | nBu | $CH_2OCH_3$ | $CH_3$ |
| 733. | $CF_3$ | nBu | nBu | $OCH_3$ | $CH_3$ |
| 734. | $CF_3$ | nBu | nBu | Ph | $CH_3$ |
| 735. | $CF_3$ | nBu | nBu | —$CH_2Ph$ | $CH_3$ |
| 736. | $CF_3$ | nBu | $CH_3$ | $CH_3$ | $CF_3$ |
| 737. | $CF_3$ | nBu | $CH_3$ | $CH_3$ | $CF_2CF_3$ |
| 738. | $CF_3$ | nBu | $CH_3$ | $CH_3$ | $CH_2OCH_3$ |
| 739. | $CF_3$ | nBu | $CH_3$ | $CH_3$ | $OCH_3$ |
| 740. | $CF_3$ | nBu | $CH_3$ | $CH_3$ | Ph |
| 741. | $CF_3$ | nBu | $CH_3$ | $CH_3$ | —$CH_2Ph$ |
| 742. | $CF_3$ | $CF_3$ | $CH_3$ | $CH_3$ | nBu |
| 743. | $CF_3$ | $CF_2CF_3$ | $CH_3$ | $CH_3$ | nBu |
| 744. | $CF_3$ | $CH_2OCH_3$ | $CH_3$ | $CH_3$ | nBu |
| 745. | $CF_3$ | $OCH_3$ | $CH_3$ | $CH_3$ | nBu |
| 746. | $CF_3$ | Ph | $CH_3$ | $CH_3$ | nBu |
| 747. | $CF_3$ | —$CH_2Ph$ | $CH_3$ | $CH_3$ | nBu |
| 748. | $CF_3$ | $CF_3$ | nBu | $CH_3$ | $CH_3$ |
| 749. | $CF_3$ | $CF_2CF_3$ | nBu | $CH_3$ | $CH_3$ |
| 750. | $CF_3$ | $CH_2OCH_3$ | nBu | $CH_3$ | $CH_3$ |
| 751. | $CF_3$ | $OCH_3$ | nBu | $CH_3$ | $CH_3$ |
| 752. | $CF_3$ | Ph | nBu | $CH_3$ | $CH_3$ |
| 753. | $CF_3$ | —$CH_2Ph$ | nBu | $CH_3$ | $CH_3$ |
| 754. | $CF_3$ | $CH_3$ | $CH_3$ | $CF_3$ | nBu |
| 755. | $CF_3$ | $CH_3$ | $CH_3$ | $CF_2CF_3$ | nBu |
| 756. | $CF_3$ | $CH_3$ | $CH_3$ | $CH_2OCH_3$ | nBu |
| 757. | $CF_3$ | $CH_3$ | $CH_3$ | $OCH_3$ | nBu |
| 758. | $CF_3$ | $CH_3$ | $CH_3$ | Ph | nBu |
| 759. | $CF_3$ | $CH_3$ | $CH_3$ | —$CH_2Ph$ | nBu |
| 760. | $CF_3$ | $CF_3$ | nBu | H | $CH_3$ |
| 761. | $CF_3$ | $CF_2CF_3$ | nBu | H | $CH_3$ |
| 762. | $CF_3$ | $CH_2OCH_3$ | nBu | H | $CH_3$ |
| 763. | $CF_3$ | $OCH_3$ | nBu | H | $CH_3$ |
| 764. | $CF_3$ | Ph | nBu | H | $CH_3$ |
| 765. | $CF_3$ | —$CH_2Ph$ | nBu | H | $CH_3$ |
| 766. | $CF_3$ | H | $CH_3$ | $CF_3$ | nBu |
| 767. | $CF_3$ | H | $CH_3$ | $CF_2CF_3$ | nBu |
| 768. | $CF_3$ | H | $CH_3$ | $CH_2OCH_3$ | nBu |
| 769. | $CF_3$ | H | $CH_3$ | $OCH_3$ | nBu |
| 770. | $CF_3$ | H | $CH_3$ | Ph | nBu |
| 771. | $CF_3$ | H | $CH_3$ | —$CH_2Ph$ | nBu |
| 772. | $CF_3$ | nBu | H | $CH_3$ | $CF_3$ |
| 773. | $CF_3$ | nBu | H | $CH_3$ | $CF_2CF_3$ |
| 774. | $CF_3$ | nBu | H | $CH_3$ | $CH_2OCH_3$ |
| 775. | $CF_3$ | nBu | H | $CH_3$ | $OCH_3$ |
| 776. | $CF_3$ | nBu | H | $CH_3$ | Ph |
| 777. | $CF_3$ | nBu | H | $CH_3$ | —$CH_2Ph$ |
| 778. | $CF_3$ | $CF_3$ | $CH_3$ | nBu | H |

TABLE B-7-continued

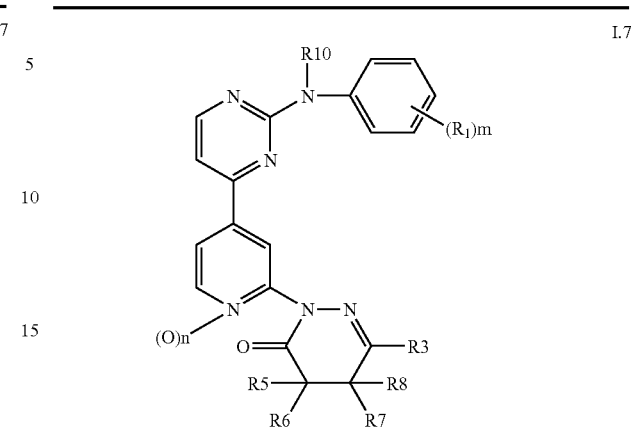

I.7

| N° | $R_3$ | $R_5$ | $R_6$ | $R_7$ | $R_8$ |
|---|---|---|---|---|---|
| 779. | $CF_3$ | $CF_2CF_3$ | $CH_3$ | nBu | H |
| 780. | $CF_3$ | $CH_2OCH_3$ | $CH_3$ | nBu | H |
| 781. | $CF_3$ | $OCH_3$ | $CH_3$ | nBu | H |
| 782. | $CF_3$ | Ph | $CH_3$ | nBu | H |
| 783. | $CF_3$ | —$CH_2Ph$ | $CH_3$ | nBu | H |
| 784. | $CF_3$ | $CF_3$ | nBu | $CH_3$ | H |
| 785. | $CF_3$ | $CF_2CF_3$ | nBu | $CH_3$ | H |
| 786. | $CF_3$ | $CH_2OCH_3$ | nBu | $CH_3$ | H |
| 787. | $CF_3$ | $OCH_3$ | nBu | $CH_3$ | H |
| 788. | $CF_3$ | Ph | nBu | $CH_3$ | H |
| 789. | $CF_3$ | —$CH_2Ph$ | nBu | $CH_3$ | H |
| 790. | $CF_3$ | $CH_3$ | H | $CF_3$ | nBu |
| 791. | $CF_3$ | $CH_3$ | H | $CF_2CF_3$ | nBu |
| 792. | $CF_3$ | $CH_3$ | H | $CH_2OCH_3$ | nBu |
| 793. | $CF_3$ | $CH_3$ | H | $OCH_3$ | nBu |
| 794. | $CF_3$ | $CH_3$ | H | Ph | nBu |
| 795. | $CF_3$ | $CH_3$ | H | —$CH_2Ph$ | nBu |
| 796. | $CF_3$ | nBu | $CH_3$ | H | $CF_3$ |
| 797. | $CF_3$ | nBu | $CH_3$ | H | $CF_2CF_3$ |
| 798. | $CF_3$ | nBu | $CH_3$ | H | $CH_2OCH_3$ |
| 799. | $CF_3$ | nBu | $CH_3$ | H | $OCH_3$ |
| 800. | $CF_3$ | nBu | $CH_3$ | H | Ph |
| 801. | $CF_3$ | nBu | $CH_3$ | H | —$CH_2Ph$ |
| 802. | $CF_3$ | $CF_3$ | H | $CH_3$ | nBu |
| 803. | $CF_3$ | $CF_2CF_3$ | H | $CH_3$ | nBu |
| 804. | $CF_3$ | $CH_2OCH_3$ | H | $CH_3$ | nBu |
| 805. | $CF_3$ | $OCH_3$ | H | $CH_3$ | nBu |
| 806. | $CF_3$ | Ph | H | $CH_3$ | nBu |
| 807. | $CF_3$ | —$CH_2Ph$ | H | $CH_3$ | nBu |
| 808. | Ph | H | H | H | H |
| 809. | Ph | $CH_3$ | H | H | H |
| 810. | Ph | H | H | $CH_3$ | H |
| 811. | Ph | $CH_3$ | $CH_3$ | H | H |
| 812. | Ph | H | H | $CH_3$ | $CH_3$ |
| 813. | Ph | $CF_3$ | H | H | H |
| 814. | Ph | H | H | $CF_3$ | H |
| 815. | OH | H | H | H | H |
| 816. | OH | $CH_3$ | H | H | H |
| 817. | OH | H | H | $CH_3$ | H |
| 818. | OH | $CH_3$ | $CH_3$ | H | H |
| 819. | OH | H | H | $CH_3$ | $CH_3$ |
| 820. | OH | H | H | $CF_3$ | H |
| 821. | OH | $CF_3$ | H | H | $CH_3$ |
| 822. | OH | $CF_3$ | H | H | H |
| 823. | OH | $CH_3$ | H | $CF_3$ | H |
| 824. | OH | H | H | $CH_2OCH_3$ | H |
| 825. | OH | $CH_2OCH_3$ | H | H | H |
| 826. | OH | $CH_2OCH_3$ | H | $CH_3$ | H |
| 827. | OH | H | $CH_3$ | $CH_2OCH_3$ | H |
| 828. | OH | $CH_2OCH_3$ | H | $CH_3$ | H |
| 829. | OH | H | $CH_3$ | $CH_2OCH_3$ | H |
| 830. | $CH_3$ | H | $(CH_2)_4$ | | H |

TABLE B-8

I.8

[Structure: pyrimidine linked to N(R10)-phenyl(R1)m, with pyridine N-oxide bearing pyridazine-dione ring with R5, R6, R7, R8, R9 substituents]

| | R5 | R6 | R7 | R8 | R9 |
|---|---|---|---|---|---|
| 1. | H | H | H | H | H |
| 2. | CH₃ | H | H | H | H |
| 3. | n-Bu | H | H | H | H |
| 4. | CF₃ | H | H | H | H |
| 5. | CF₂CF₃ | H | H | H | H |
| 6. | CH₂OCH₃ | H | H | H | H |
| 7. | OCH₃ | H | H | H | H |
| 8. | Ph | H | H | H | H |
| 9. | —CH₂Ph | H | H | H | H |
| 10. | H | H | CH₃ | H | H |
| 11. | H | H | n-Bu | H | H |
| 12. | H | H | CF₃ | H | H |
| 13. | H | H | CF₂CF₃ | H | H |
| 14. | H | H | CH₂OCH₃ | H | H |
| 15. | H | H | OCH₃ | H | H |
| 16. | H | H | Ph | H | H |
| 17. | H | H | —CH₂Ph | H | H |
| 18. | CH₃ | CH₃ | H | H | H |
| 19. | n-Bu | CH₃ | H | H | H |
| 20. | CF₃ | CH₃ | H | H | H |
| 21. | CF₂CF₃ | CH₃ | H | H | H |
| 22. | CH₂OCH₃ | CH₃ | H | H | H |
| 23. | OCH₃ | CH₃ | H | H | H |
| 24. | Ph | CH₃ | H | H | H |
| 25. | —CH₂Ph | CH₃ | H | H | H |
| 26. | H | H | CH₃ | CH₃ | H |
| 27. | H | H | CH₃ | n-Bu | H |
| 28. | H | H | CH₃ | CF₃ | H |
| 29. | H | H | CH₃ | CF₂CF₃ | H |
| 30. | H | H | CH₃ | CH₂OCH₃ | H |
| 31. | H | H | CH₃ | OCH₃ | H |
| 32. | H | H | CH₃ | Ph | H |
| 33. | H | H | CH₃ | CH₂Ph | H |
| 34. | CH₃ | H | H | CH₃ | H |
| 35. | n-Bu | H | H | CH₃ | H |
| 36. | CF₃ | H | H | CH₃ | H |
| 37. | CF₂CF₃ | H | H | CH₃ | H |
| 38. | CH₂OCH₃ | H | H | CH₃ | H |
| 39. | OCH₃ | H | H | CH₃ | H |
| 40. | Ph | H | H | CH₃ | H |
| 41. | —CH₂Ph | H | H | CH₃ | H |
| 42. | H | CH₃ | n-Bu | H | H |
| 43. | H | CH₃ | CF₃ | H | H |
| 44. | H | CH₃ | CF₂CF₃ | H | H |
| 45. | H | CH₃ | CH₂OCH₃ | H | H |
| 46. | H | CH₃ | OCH₃ | H | H |
| 47. | H | CH₃ | Ph | H | H |
| 48. | H | CH₃ | —CH₂Ph | H | H |
| 49. | CH₃ | H | CH₃ | CH₃ | H |
| 50. | n-Bu | H | CH₃ | CH₃ | H |
| 51. | CF₃ | H | CH₃ | CH₃ | H |
| 52. | CF₂CF₃ | H | CH₃ | CH₃ | H |
| 53. | CH₂OCH₃ | H | CH₃ | CH₃ | H |
| 54. | OCH₃ | H | CH₃ | CH₃ | H |
| 55. | Ph | H | CH₃ | CH₃ | H |
| 56. | CH₂Ph | H | CH₃ | CH₃ | H |
| 57. | CH₃ | CH₃ | CH₃ | H | H |
| 58. | CH₃ | CH₃ | n-Bu | H | H |
| 59. | CH₃ | CH₃ | CF₃ | H | H |
| 60. | CH₃ | CH₃ | CF₂CF₃ | H | H |
| 61. | CH₃ | CH₃ | CH₂OCH₃ | H | H |
| 62. | CH₃ | CH₃ | OCH₃ | H | H |
| 63. | CH₃ | CH₃ | Ph | H | H |
| 64. | CH₃ | CH₃ | —CH₂Ph | H | H |
| 65. | n-Bu | CH₃ | CH₃ | H | H |
| 66. | CF₃ | CH₃ | CH₃ | H | H |
| 67. | CF₂CF₃ | CH₃ | CH₃ | H | H |
| 68. | CH₂OCH₃ | CH₃ | CH₃ | H | H |
| 69. | OCH₃ | CH₃ | CH₃ | H | H |
| 70. | Ph | CH₃ | CH₃ | H | H |
| 71. | CH₂Ph | CH₃ | CH₃ | H | H |
| 72. | CH₃ | H | CH₃ | n-Bu | H |
| 73. | CH₃ | H | CH₃ | CF₃ | H |
| 74. | CH₃ | H | CH₃ | CF₂CF₃ | H |
| 75. | CH₃ | H | CH₃ | CH₂OCH₃ | H |
| 76. | CH₃ | H | CH₃ | OCH₃ | H |
| 77. | CH₃ | H | CH₃ | Ph | H |
| 78. | CH₃ | H | CH₃ | CH₂Ph | H |
| 79. | CH₃ | CH₃ | CH₃ | CH₃ | H |
| 80. | n-Bu | CH₃ | CH₃ | CH₃ | H |
| 81. | CF₃ | CH₃ | CH₃ | CH₃ | H |
| 82. | CF₂CF₃ | CH₃ | CH₃ | CH₃ | H |
| 83. | CH₂OCH₃ | CH₃ | CH₃ | CH₃ | H |
| 84. | OCH₃ | CH₃ | CH₃ | CH₃ | H |
| 85. | Ph | CH₃ | CH₃ | CH₃ | H |
| 86. | CH₂Ph | CH₃ | CH₃ | CH₃ | H |
| 87. | CH₃ | CH₃ | CH₃ | n-Bu | H |
| 88. | CH₃ | CH₃ | CH₃ | CF₃ | H |
| 89. | CH₃ | CH₃ | CH₃ | CF₂CF₃ | H |
| 90. | CH₃ | CH₃ | CH₃ | CH₂CH₃ | H |
| 91. | CH₃ | CH₃ | CH₃ | OCH₃ | H |
| 92. | CH₃ | CH₃ | CH₃ | Ph | H |
| 93. | CH₃ | CH₃ | CH₃ | CH₂Ph | H |
| 94. | n-Bu | n-Bu | H | H | H |
| 95. | CF₃ | n-Bu | H | H | H |
| 96. | CF₂CF₃ | n-Bu | H | H | H |
| 97. | CH₂OCH₃ | n-Bu | H | H | H |
| 98. | OCH₃ | n-Bu | H | H | H |
| 99. | Ph | n-Bu | H | H | H |
| 100. | CH₂Ph | n-Bu | H | H | H |
| 101. | H | H | n-Bu | n-Bu | H |
| 102. | H | H | CF₃ | n-Bu | H |
| 103. | H | H | CF₂CF₃ | n-Bu | H |
| 104. | H | H | CH₂OCH₃ | n-Bu | H |
| 105. | H | H | OCH₃ | n-Bu | H |
| 106. | H | H | Ph | n-Bu | H |
| 107. | H | H | —CH₂Ph | n-Bu | H |
| 108. | n-Bu | H | H | H | H |
| 109. | n-Bu | H | H | CH₃ | H |
| 110. | n-Bu | H | H | v | H |
| 111. | n-Bu | H | H | CF₃ | H |
| 112. | n-Bu | H | H | CF₂CF₃ | H |

TABLE B-8-continued

I.8

|     | R₅ | R₆ | R₇ | R₈ | R₉ |
|---|---|---|---|---|---|
| 113. | n-Bu | H | H | CH₂OCH₃ | H |
| 114. | n-Bu | H | H | OCH₃ | H |
| 115. | n-Bu | H | H | Ph | H |
| 116. | n-Bu | H | H | —CH₂Ph | H |
| 117. | H | H | n-Bu | H | H |
| 118. | H | CH₃ | n-Bu | H | H |
| 119. | H | n-Bu | n-Bu | H | H |
| 120. | H | CF₃ | n-Bu | H | H |
| 121. | H | CF₂CF₃ | n-Bu | H | H |
| 122. | H | CH₂OCH₃ | n-Bu | H | H |
| 123. | H | OCH₃ | n-Bu | H | H |
| 124. | H | Ph | n-Bu | H | H |
| 125. | H | —CH₂Ph | n-Bu | H | H |
| 126. | CH₃ | n-Bu | n-Bu | H | H |
| 127. | n-Bu | n-Bu | n-Bu | H | H |
| 128. | CF₃ | n-Bu | n-Bu | H | H |
| 129. | CF₂CF₃ | n-Bu | n-Bu | H | H |
| 130. | CH₂OCH₃ | n-Bu | n-Bu | H | H |
| 131. | OCH₃ | n-Bu | n-Bu | H | H |
| 132. | Ph | n-Bu | n-Bu | H | H |
| 133. | —CH₂Ph | n-Bu | n-Bu | H | H |
| 134. | CH₃ | H | n-Bu | n-Bu | H |
| 135. | n-Bu | H | n-Bu | n-Bu | H |
| 136. | CF₃ | H | n-Bu | n-Bu | H |
| 137. | CF₂CF₃ | H | n-Bu | n-Bu | H |
| 138. | CH₂OCH₃ | H | n-Bu | n-Bu | H |
| 139. | OCH₃ | H | n-Bu | n-Bu | H |
| 140. | Ph | H | n-Bu | n-Bu | H |
| 141. | —CH₂Ph | H | n-Bu | n-Bu | H |
| 142. | n-Bu | n-Bu | CH₃ | H | H |
| 143. | n-Bu | n-Bu | CF₃ | H | H |
| 144. | n-Bu | n-Bu | CF₂CF₃ | H | H |
| 145. | n-Bu | n-Bu | CH₂OCH₃ | H | H |
| 146. | n-Bu | n-Bu | OCH₃ | H | H |
| 147. | n-Bu | n-Bu | Ph | H | H |
| 148. | n-Bu | n-Bu | —CH₂Ph | H | H |
| 149. | n-Bu | H | CH₃ | n-Bu | H |
| 150. | n-Bu | H | CF₃ | n-Bu | H |
| 151. | n-Bu | H | CF₂CF₃ | n-Bu | H |
| 152. | n-Bu | H | CH₂OCH₃ | n-Bu | H |
| 153. | n-Bu | H | OCH₃ | n-Bu | H |
| 154. | n-Bu | H | Ph | n-Bu | H |
| 155. | n-Bu | H | —CH₂Ph | n-Bu | H |
| 156. | CH₃ | n-Bu | n-Bu | n-Bu | H |
| 157. | n-Bu | n-Bu | n-Bu | n-Bu | H |
| 158. | CF₃ | n-Bu | n-Bu | n-Bu | H |
| 159. | CF₂CF₃ | n-Bu | n-Bu | n-Bu | H |
| 160. | CH₂OCH₃ | n-Bu | n-Bu | n-Bu | H |
| 161. | OCH₃ | n-Bu | n-Bu | n-Bu | H |
| 162. | Ph | n-Bu | n-Bu | n-Bu | H |
| 163. | —CH₂Ph | n-Bu | n-Bu | n-Bu | H |
| 164. | n-Bu | n-Bu | n-Bu | CH₃ | H |
| 165. | n-Bu | n-Bu | n-Bu | CF3 | H |
| 166. | n-Bu | n-Bu | n-Bu | CF₂CF₃ | H |
| 167. | n-Bu | n-Bu | n-Bu | CH₂OCH₃ | H |
| 168. | n-Bu | n-Bu | n-Bu | OCH₃ | H |
| 169. | n-Bu | n-Bu | n-Bu | Ph | H |
| 170. | n-Bu | n-Bu | n-Bu | —CH₂Ph | H |
| 171. | n-Bu | CH₃ | n-Bu | CH₃ | H |
| 172. | n-Bu | CH₃ | n-Bu | CF₃ | H |
| 173. | n-Bu | CH₃ | n-Bu | CF₂CF₃ | H |
| 174. | n-Bu | CH₃ | n-Bu | CH₂OCH₃ | H |
| 175. | n-Bu | CH₃ | n-Bu | OCH₃ | H |
| 176. | n-Bu | CH₃ | n-Bu | Ph | H |
| 177. | n-Bu | CH₃ | n-Bu | —CH₂Ph | H |
| 178. | CF₃ | n-Bu | n-Bu | CH₃ | H |
| 179. | CF₂CF₃ | n-Bu | n-Bu | CH₃ | H |
| 180. | CH₂OCH₃ | n-Bu | n-Bu | CH₃ | H |
| 181. | OCH₃ | n-Bu | n-Bu | CH₃ | H |
| 182. | Ph | n-Bu | n-Bu | CH₃ | H |
| 183. | —CH₂Ph | n-Bu | n-Bu | CH₃ | H |
| 184. | CH₃ | CH₃ | n-Bu | n-Bu | H |
| 185. | CF₃ | CH₃ | n-Bu | n | H |
| 186. | CF₂CF₃ | CH₃ | n-Bu | n | H |
| 187. | CH₂OCH₃ | CH₃ | n-Bu | n | H |
| 188. | OCH₃ | CH₃ | n-Bu | n | H |
| 189. | Ph | CH₃ | n-Bu | n | H |
| 190. | —CH₂Ph | CH₃ | n-Bu | n | H |
| 191. | n-Bu | n-Bu | CH₃ | CH₃ | H |
| 192. | n-Bu | n-Bu | CF₃ | CH₃ | H |
| 193. | n-Bu | n-Bu | CF₂CF₃ | CH₃ | H |
| 194. | n-Bu | n-Bu | CH₂OCH₃ | CH₃ | H |
| 195. | n-Bu | n-Bu | OCH₃ | CH₃ | H |
| 196. | n-Bu | n-Bu | Ph | CH₃ | H |
| 197. | n-Bu | n-Bu | —CH₂Ph | CH₃ | H |
| 198. | n-Bu | CH₃ | CH₃ | CF₃ | H |
| 199. | n-Bu | CH₃ | CH₃ | CF₂CF₃ | H |
| 200. | n-Bu | CH₃ | CH₃ | CH₂OCH₃ | H |
| 201. | n-Bu | CH₃ | CH₃ | OCH₃ | H |
| 202. | n-Bu | CH₃ | CH₃ | Ph | H |
| 203. | n-Bu | CH₃ | CH₃ | —CH₂Ph | H |
| 204. | CF₃ | CH₃ | CH₃ | n-Bu | H |
| 205. | CF₂CF₃ | CH₃ | CH₃ | n-Bu | H |
| 206. | CH₂OCH₃ | CH₃ | CH₃ | n-Bu | H |
| 207. | OCH₃ | CH₃ | CH₃ | n-Bu | H |
| 208. | Ph | CH₃ | CH₃ | n-Bu | H |
| 209. | —CH₂Ph | CH₃ | CH₃ | n-Bu | H |
| 210. | CF₃ | n-Bu | CH₃ | CH₃ | H |
| 211. | CF₂CF₃ | n-Bu | CH₃ | CH₃ | H |
| 212. | CH₂OCH₃ | n-Bu | CH₃ | CH₃ | H |
| 213. | OCH₃ | n-Bu | CH₃ | CH₃ | H |
| 214. | Ph | n-Bu | CH₃ | CH₃ | H |
| 215. | —CH₂Ph | n-Bu | CH₃ | CH₃ | H |
| 216. | CH₃ | CH₃ | CF₃ | n-Bu | H |
| 217. | CH₃ | CH₃ | CF₂CF₃ | n-Bu | H |
| 218. | CH₃ | CH₃ | CH₂OCH₃ | n-Bu | H |
| 219. | CH₃ | CH₃ | OCH₃ | n-Bu | H |
| 220. | CH₃ | CH₃ | Ph | n-Bu | H |
| 221. | CH₃ | CH₃ | —CH₂Ph | n-Bu | H |
| 222. | CF₃ | n-Bu | H | CH₃ | H |
| 223. | CF₂CF₃ | n-Bu | H | CH₃ | H |
| 224. | CH₂OCH₃ | n-Bu | H | CH₃ | H |

TABLE B-8-continued

I.8

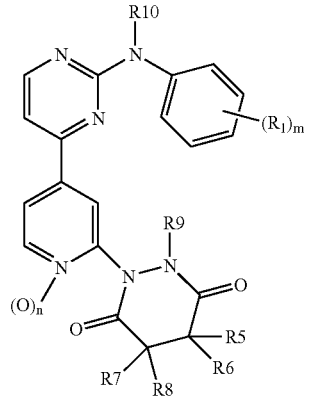

| | R5 | R6 | R7 | R8 | R9 |
|---|---|---|---|---|---|
| 225. | $OCH_3$ | n-Bu | H | $CH_3$ | H |
| 226. | Ph | n-Bu | H | $CH_3$ | H |
| 227. | —$CH_2Ph$ | n-Bu | H | $CH_3$ | H |
| 228. | H | $CH_3$ | $CF_3$ | n-Bu | H |
| 229. | H | $CH_3$ | $CF_2CF_3$ | n-Bu | H |
| 230. | H | $CH_3$ | $CH_2OCH_3$ | n-Bu | H |
| 231. | H | $CH_3$ | $OCH_3$ | n-Bu | H |
| 232. | H | $CH_3$ | Ph | n-Bu | H |
| 233. | H | $CH_3$ | —$CH_2Ph$ | n-Bu | H |
| 234. | n-Bu | H | $CH_3$ | $CF_3$ | H |
| 235. | n-Bu | H | $CH_3$ | $CF_2CF_3$ | H |
| 236. | n-Bu | H | $CH_3$ | $CH_2OCH_3$ | H |
| 237. | n-Bu | H | $CH_3$ | $OCH_3$ | H |
| 238. | n-Bu | H | $CH_3$ | Ph | H |
| 239. | n-Bu | H | $CH_3$ | —$CH_2Ph$ | H |
| 240. | $CF_3$ | $CH_3$ | n-Bu | H | H |
| 241. | $CF_2CF_3$ | $CH_3$ | n-Bu | H | H |
| 242. | $CH_2OCH_3$ | $CH_3$ | n-Bu | H | H |
| 243. | $OCH_3$ | $CH_3$ | n-Bu | H | H |
| 244. | Ph | $CH_3$ | n-Bu | H | H |
| 245. | —$CH_2Ph$ | $CH_3$ | n-Bu | H | H |
| 246. | $CF_3$ | n-Bu | $CH_3$ | H | H |
| 247. | $CF_2CF_3$ | n-Bu | $CH_3$ | H | H |
| 248. | $CH_2OCH_3$ | n-Bu | $CH_3$ | H | H |
| 249. | $OCH_3$ | n-Bu | $CH_3$ | H | H |
| 250. | Ph | n-Bu | $CH_3$ | H | H |
| 251. | —$CH_2Ph$ | n-Bu | $CH_3$ | H | H |
| 252. | $CH_3$ | H | $CF_3$ | n-Bu | H |
| 253. | $CH_3$ | H | $CF_2CF_3$ | n-Bu | H |
| 254. | $CH_3$ | H | $CH_2OCH_3$ | n-Bu | H |
| 255. | $CH_3$ | H | $OCH_3$ | n-Bu | H |
| 256. | $CH_3$ | H | Ph | n-Bu | H |
| 257. | $CH_3$ | H | —$CH_2Ph$ | n-Bu | H |
| 258. | n-Bu | $CH_3$ | H | $CF_3$ | H |
| 259. | n-Bu | $CH_3$ | H | $CF_2CF_3$ | H |
| 260. | n-Bu | $CH_3$ | H | $CH_2OCH_3$ | H |
| 261. | n-Bu | $CH_3$ | H | $OCH_3$ | H |
| 262. | n-Bu | $CH_3$ | H | Ph | H |
| 263. | n-Bu | $CH_3$ | H | —$CH_2Ph$ | H |
| 264. | $CF_3$ | H | $CH_3$ | n-Bu | H |
| 265. | $CF_2CF_3$ | H | $CH_3$ | n-Bu | H |
| 266. | $CH_2OCH_3$ | H | $CH_3$ | n-Bu | H |
| 267. | $OCH_3$ | H | $CH_3$ | n-Bu | H |
| 268. | Ph | H | $CH_3$ | n-Bu | H |
| 269. | —$CH_2Ph$ | H | $CH_3$ | n-Bu | H |
| 270. | H | H | H | H | $CH_3$ |
| 271. | $CH_3$ | H | H | H | $CH_3$ |
| 272. | n-Bu | H | H | H | $CH_3$ |
| 273. | $CF_3$ | H | H | H | $CH_3$ |
| 274. | $CF_2CF_3$ | H | H | H | $CH_3$ |
| 275. | $CH_2OCH_3$ | H | H | H | $CH_3$ |
| 276. | $OCH_3$ | H | H | H | $CH_3$ |
| 277. | Ph | H | H | H | $CH_3$ |
| 278. | —$CH_2Ph$ | H | H | H | $CH_3$ |
| 279. | H | H | $CH_3$ | H | $CH_3$ |
| 280. | H | H | n-Bu | H | $CH_3$ |

TABLE B-8-continued

I.8

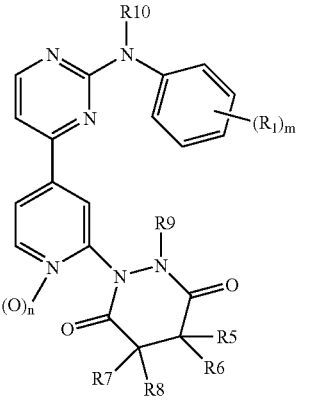

| | R5 | R6 | R7 | R8 | R9 |
|---|---|---|---|---|---|
| 281. | H | H | $CF_3$ | H | $CH_3$ |
| 282. | H | H | $CF_2CF_3$ | H | $CH_3$ |
| 283. | H | H | $CH_2OCH_3$ | H | $CH_3$ |
| 284. | H | H | $OCH_3$ | H | $CH_3$ |
| 285. | H | H | Ph | H | $CH_3$ |
| 286. | H | H | —$CH_2Ph$ | H | $CH_3$ |
| 287. | $CH_3$ | $CH_3$ | H | H | $CH_3$ |
| 288. | n-Bu | $CH_3$ | H | H | $CH_3$ |
| 289. | $CF_3$ | $CH_3$ | H | H | $CH_3$ |
| 290. | $CF_2CF_3$ | $CH_3$ | H | H | $CH_3$ |
| 291. | $CH_2OCH_3$ | $CH_3$ | H | H | $CH_3$ |
| 292. | $OCH_3$ | $CH_3$ | H | H | $CH_3$ |
| 293. | Ph | $CH_3$ | H | H | $CH_3$ |
| 294. | —$CH_2Ph$ | $CH_3$ | H | H | $CH_3$ |
| 295. | H | H | $CH_3$ | $CH_3$ | $CH_3$ |
| 296. | H | H | $CH_3$ | n-Bu | $CH_3$ |
| 297. | H | H | $CH_3$ | $CF_3$ | $CH_3$ |
| 298. | H | H | $CH_3$ | $CF_2CF_3$ | $CH_3$ |
| 299. | H | H | $CH_3$ | $CH_2OCH_3$ | $CH_3$ |
| 300. | H | H | $CH_3$ | $OCH_3$ | $CH_3$ |
| 301. | H | H | $CH_3$ | Ph | $CH_3$ |
| 302. | H | H | $CH_3$ | —$CH_2Ph$ | $CH_3$ |
| 303. | $CH_3$ | H | H | $CH_3$ | $CH_3$ |
| 304. | n-Bu | H | H | $CH_3$ | $CH_3$ |
| 305. | $CF_3$ | H | H | $CH_3$ | $CH_3$ |
| 306. | $CF_2CF_3$ | H | H | $CH_3$ | $CH_3$ |
| 307. | $CH_2OCH_3$ | H | H | $CH_3$ | $CH_3$ |
| 308. | $OCH_3$ | H | H | $CH_3$ | $CH_3$ |
| 309. | Ph | H | H | $CH_3$ | $CH_3$ |
| 310. | —$CH_2Ph$ | H | H | $CH_3$ | $CH_3$ |
| 311. | H | $CH_3$ | n-Bu | H | $CH_3$ |
| 312. | H | $CH_3$ | $CF_3$ | H | $CH_3$ |
| 313. | H | $CH_3$ | $CF_2CF_3$ | H | $CH_3$ |
| 314. | H | $CH_3$ | $CH_2OCH_3$ | H | $CH_3$ |
| 315. | H | $CH_3$ | $OCH_3$ | H | $CH_3$ |
| 316. | H | $CH_3$ | Ph | H | $CH_3$ |
| 317. | H | $CH_3$ | —$CH_2Ph$ | H | $CH_3$ |
| 318. | $CH_3$ | H | $CH_3$ | $CH_3$ | $CH_3$ |
| 319. | n-Bu | H | $CH_3$ | $CH_3$ | $CH_3$ |
| 320. | $CF_3$ | H | $CH_3$ | $CH_3$ | $CH_3$ |
| 321. | $CF_2CF_3$ | H | $CH_3$ | $CH_3$ | $CH_3$ |
| 322. | $CH_2OCH_3$ | H | $CH_3$ | $CH_3$ | $CH_3$ |
| 323. | $OCH_3$ | H | $CH_3$ | $CH_3$ | $CH_3$ |
| 324. | Ph | H | $CH_3$ | $CH_3$ | $CH_3$ |
| 325. | —$CH_2Ph$ | H | $CH_3$ | $CH_3$ | $CH_3$ |
| 326. | $CH_3$ | $CH_3$ | $CH_3$ | H | $CH_3$ |
| 327. | $CH_3$ | $CH_3$ | n-Bu | H | $CH_3$ |
| 328. | $CH_3$ | $CH_3$ | $CF_3$ | H | $CH_3$ |
| 329. | $CH_3$ | $CH_3$ | $CF_2CF_3$ | H | $CH_3$ |
| 330. | $CH_3$ | $CH_3$ | $CH_2OCH_3$ | H | $CH_3$ |
| 331. | $CH_3$ | $CH_3$ | $OCH_3$ | H | $CH_3$ |
| 332. | $CH_3$ | $CH_3$ | Ph | H | $CH_3$ |
| 333. | $CH_3$ | $CH_3$ | —$CH_2Ph$ | H | $CH_3$ |
| 334. | n-Bu | $CH_3$ | $CH_3$ | H | $CH_3$ |
| 335. | $CF_3$ | $CH_3$ | $CH_3$ | H | $CH_3$ |
| 336. | $CF_2CF_3$ | $CH_3$ | $CH_3$ | H | $CH_3$ |

TABLE B-8-continued

I.8

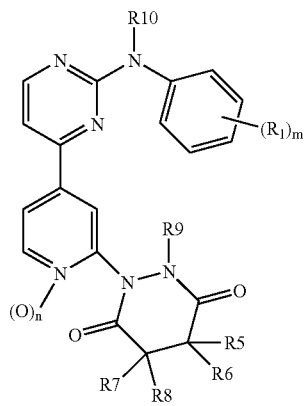

| | $R_5$ | $R_6$ | $R_7$ | $R_8$ | $R_9$ |
|---|---|---|---|---|---|
| 337. | $CH_2OCH_3$ | $CH_3$ | $CH_3$ | H | $CH_3$ |
| 338. | $OCH_3$ | $CH_3$ | $CH_3$ | H | $CH_3$ |
| 339. | Ph | $CH_3$ | $CH_3$ | H | $CH_3$ |
| 340. | —$CH_2Ph$ | $CH_3$ | $CH_3$ | H | $CH_3$ |
| 341. | $CH_3$ | H | $CH_3$ | n-Bu | $CH_3$ |
| 342. | $CH_3$ | H | $CH_3$ | $CF_3$ | $CH_3$ |
| 343. | $CH_3$ | H | $CH_3$ | $CF_2CF_3$ | $CH_3$ |
| 344. | $CH_3$ | H | $CH_3$ | $CH_2OCH_3$ | $CH_3$ |
| 345. | $CH_3$ | H | $CH_3$ | $OCH_3$ | $CH_3$ |
| 346. | $CH_3$ | H | $CH_3$ | Ph | $CH_3$ |
| 347. | $CH_3$ | H | $CH_3$ | —$CH_2Ph$ | $CH_3$ |
| 348. | $CH_3$ | $CH_3$ | $CH_3$ | $CH_3$ | $CH_3$ |
| 349. | n-Bu | $CH_3$ | $CH_3$ | $CH_3$ | $CH_3$ |
| 350. | $CF_3$ | $CH_3$ | $CH_3$ | $CH_3$ | $CH_3$ |
| 351. | $CF_2CF_3$ | $CH_3$ | $CH_3$ | $CH_3$ | $CH_3$ |
| 352. | $CH_2OCH_3$ | $CH_3$ | $CH_3$ | $CH_3$ | $CH_3$ |
| 353. | $OCH_3$ | $CH_3$ | $CH_3$ | $CH_3$ | $CH_3$ |
| 354. | Ph | $CH_3$ | $CH_3$ | $CH_3$ | $CH_3$ |
| 355. | —$CH_2Ph$ | $CH_3$ | $CH_3$ | $CH_3$ | $CH_3$ |
| 356. | $CH_3$ | $CH_3$ | $CH_3$ | n-Bu | $CH_3$ |
| 357. | $CH_3$ | $CH_3$ | $CH_3$ | $CF_3$ | $CH_3$ |
| 358. | $CH_3$ | $CH_3$ | $CH_3$ | $CF_2CF_3$ | $CH_3$ |
| 359. | $CH_3$ | $CH_3$ | $CH_3$ | $CH_2OCH_3$ | $CH_3$ |
| 360. | $CH_3$ | $CH_3$ | $CH_3$ | $OCH_3$ | $CH_3$ |
| 361. | $CH_3$ | $CH_3$ | $CH_3$ | Ph | $CH_3$ |
| 362. | $CH_3$ | $CH_3$ | $CH_3$ | —$CH_2Ph$ | $CH_3$ |
| 363. | n-Bu | n-Bu | H | H | $CH_3$ |
| 364. | $CF_3$ | n-Bu | H | H | $CH_3$ |
| 365. | $CF_2CF_3$ | n-Bu | H | H | $CH_3$ |
| 366. | $CH_2OCH_3$ | n-Bu | H | H | $CH_3$ |
| 367. | $OCH_3$ | n-Bu | H | H | $CH_3$ |
| 368. | Ph | n-Bu | H | H | $CH_3$ |
| 369. | —$CH_2Ph$ | n-Bu | H | H | $CH_3$ |
| 370. | H | H | n-Bu | n-Bu | $CH_3$ |
| 371. | H | H | $CF_3$ | n-Bu | $CH_3$ |
| 372. | H | H | $CF_2CF_3$ | n-Bu | $CH_3$ |
| 373. | H | H | $CH_2OCH_3$ | n-Bu | $CH_3$ |
| 374. | H | H | $OCH_3$ | n-Bu | $CH_3$ |
| 375. | H | H | Ph | n-Bu | $CH_3$ |
| 376. | H | H | —$CH_2Ph$ | n-Bu | $CH_3$ |
| 377. | n-Bu | H | H | H | $CH_3$ |
| 378. | n-Bu | H | H | $CH_3$ | $CH_3$ |
| 379. | n-Bu | H | H | n-Bu | $CH_3$ |
| 380. | n-Bu | H | H | $CF_3$ | $CH_3$ |
| 381. | n-Bu | H | H | $CF_2CF_3$ | $CH_3$ |
| 382. | n-Bu | H | H | $CH_2OCH_3$ | $CH_3$ |
| 383. | n-Bu | H | H | $OCH_3$ | $CH_3$ |
| 384. | n-Bu | H | H | Ph | $CH_3$ |
| 385. | n-Bu | H | H | —$CH_2Ph$ | $CH_3$ |
| 386. | H | H | n-Bu | H | $CH_3$ |
| 387. | H | $CH_3$ | n-Bu | H | $CH_3$ |
| 388. | H | n-Bu | n-Bu | H | $CH_3$ |
| 389. | H | $CF_3$ | n-Bu | H | $CH_3$ |
| 390. | H | $CF_2CF_3$ | n-Bu | H | $CH_3$ |
| 391. | H | $CH_2OCH_3$ | n-Bu | H | $CH_3$ |
| 392. | H | $OCH_3$ | n-Bu | H | $CH_3$ |

TABLE B-8-continued

I.8

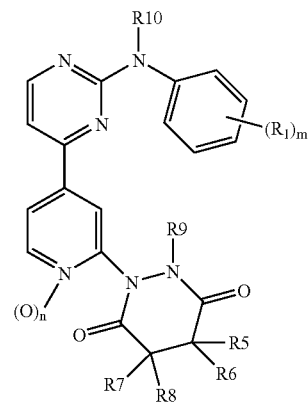

| | $R_5$ | $R_6$ | $R_7$ | $R_8$ | $R_9$ |
|---|---|---|---|---|---|
| 393. | H | Ph | n-Bu | H | $CH_3$ |
| 394. | H | —$CH_2Ph$ | n-Bu | H | $CH_3$ |
| 395. | $CH_3$ | n-Bu | n-Bu | H | $CH_3$ |
| 396. | n-Bu | n-Bu | n-Bu | H | $CH_3$ |
| 397. | $CF_3$ | n-Bu | n-Bu | H | $CH_3$ |
| 398. | $CF_2CF_3$ | n-Bu | n-Bu | H | $CH_3$ |
| 399. | $CH_2OCH_3$ | n-Bu | n-Bu | H | $CH_3$ |
| 400. | $OCH_3$ | n-Bu | n-Bu | H | $CH_3$ |
| 401. | Ph | n-Bu | n-Bu | H | $CH_3$ |
| 402. | —$CH_2Ph$ | n-Bu | n-Bu | H | $CH_3$ |
| 403. | $CH_3$ | H | n-Bu | n-Bu | $CH_3$ |
| 404. | n-Bu | H | n-Bu | n-Bu | $CH_3$ |
| 405. | $CF_3$ | H | n-Bu | n-Bu | $CH_3$ |
| 406. | $CF_2CF_3$ | H | n-Bu | n-Bu | $CH_3$ |
| 407. | $CH_2OCH_3$ | H | n-Bu | n-Bu | $CH_3$ |
| 408. | $OCH_3$ | H | n-Bu | n-Bu | $CH_3$ |
| 409. | Ph | H | n-Bu | n-Bu | $CH_3$ |
| 410. | —$CH_2Ph$ | H | n-Bu | n-Bu | $CH_3$ |
| 411. | n-Bu | n-Bu | $CH_3$ | H | $CH_3$ |
| 412. | n-Bu | n-Bu | $CF_3$ | H | $CH_3$ |
| 413. | n-Bu | n-Bu | $CF_2CF_3$ | H | $CH_3$ |
| 414. | n-Bu | n-Bu | $CH_2OCH_3$ | H | $CH_3$ |
| 415. | n-Bu | n-Bu | $OCH_3$ | H | $CH_3$ |
| 416. | n-Bu | n-Bu | Ph | H | $CH_3$ |
| 417. | n-Bu | n-Bu | —$CH_2Ph$ | H | $CH_3$ |
| 418. | n-Bu | H | $CH_3$ | n-Bu | $CH_3$ |
| 419. | n-Bu | H | $CF_3$ | n-Bu | $CH_3$ |
| 420. | n-Bu | H | $CF_2CF_3$ | n-Bu | $CH_3$ |
| 421. | n-Bu | H | $CH_2OCH_3$ | n-Bu | $CH_3$ |
| 422. | n-Bu | H | $OCH_3$ | n-Bu | $CH_3$ |
| 423. | n-Bu | H | Ph | n-Bu | $CH_3$ |
| 424. | n-Bu | H | —$CH_2Ph$ | n-Bu | $CH_3$ |
| 425. | $CH_3$ | n-Bu | n-Bu | n-Bu | $CH_3$ |
| 426. | n-Bu | n-Bu | n-Bu | n-Bu | $CH_3$ |
| 427. | $CF_3$ | n-Bu | n-Bu | n-Bu | $CH_3$ |
| 428. | $CF_2CF_3$ | n-Bu | n-Bu | n-Bu | $CH_3$ |
| 429. | $CH_2OCH_3$ | n-Bu | n-Bu | n-Bu | $CH_3$ |
| 430. | $OCH_3$ | n-Bu | n-Bu | n-Bu | $CH_3$ |
| 431. | Ph | n-Bu | n-Bu | n-Bu | $CH_3$ |
| 432. | —$CH_2Ph$ | n-Bu | n-Bu | n-Bu | $CH_3$ |
| 433. | n-Bu | n-Bu | n-Bu | $CH_3$ | $CH_3$ |
| 434. | n-Bu | n-Bu | n-Bu | $CF_3$ | $CH_3$ |
| 435. | n-Bu | n-Bu | n-Bu | $CF_2CF_3$ | $CH_3$ |
| 436. | n-Bu | n-Bu | n-Bu | $CH_2OCH_3$ | $CH_3$ |
| 437. | n-Bu | n-Bu | n-Bu | $OCH_3$ | $CH_3$ |
| 438. | n-Bu | n-Bu | n-Bu | Ph | $CH_3$ |
| 439. | n-Bu | n-Bu | n-Bu | —$CH_2Ph$ | $CH_3$ |
| 440. | n-Bu | $CH_3$ | n-Bu | $CH_3$ | $CH_3$ |
| 441. | n-Bu | $CH_3$ | n-Bu | $CF_3$ | $CH_3$ |
| 442. | n-Bu | $CH_3$ | n-Bu | $CF_2CF_3$ | $CH_3$ |
| 443. | n-Bu | $CH_3$ | n-Bu | $CH_2OCH_3$ | $CH_3$ |
| 444. | n-Bu | $CH_3$ | n-Bu | $OCH_3$ | $CH_3$ |
| 445. | n-Bu | $CH_3$ | n-Bu | Ph | $CH_3$ |
| 446. | n-Bu | $CH_3$ | n-Bu | —$CH_2Ph$ | $CH_3$ |
| 447. | $CF_3$ | n-Bu | n-Bu | $CH_3$ | $CH_3$ |
| 448. | $CF_2CF_3$ | n-Bu | n-Bu | $CH_3$ | $CH_3$ |

TABLE B-8-continued

I.8

| | R₅ | R₆ | R₇ | R₈ | R₉ |
|---|---|---|---|---|---|
| 449. | CH₂OCH₃ | n-Bu | n-Bu | CH₃ | CH₃ |
| 450. | OCH₃ | n-Bu | n-Bu | CH₃ | CH₃ |
| 451. | Ph | n-Bu | n-Bu | CH₃ | CH₃ |
| 452. | —CH₂Ph | n-Bu | n-Bu | CH₃ | CH₃ |
| 453. | CH₃ | CH₃ | n-Bu | n-Bu | CH₃ |
| 454. | CF₃ | CH₃ | n-Bu | n-Bu | CH₃ |
| 455. | CF₂CF₃ | CH₃ | n-Bu | n-Bu | CH₃ |
| 456. | CH₂OCH₃ | CH₃ | n-Bu | n-Bu | CH₃ |
| 457. | OCH₃ | CH₃ | n-Bu | n-Bu | CH₃ |
| 458. | Ph | CH₃ | n-Bu | n-Bu | CH₃ |
| 459. | —CH₂Ph | CH₃ | n-Bu | n-Bu | CH₃ |
| 460. | n-Bu | n-Bu | CH₃ | CH₃ | CH₃ |
| 461. | n-Bu | n-Bu | CF₃ | CH₃ | CH₃ |
| 462. | n-Bu | n-Bu | CF₂CF₃ | CH₃ | CH₃ |
| 463. | n-Bu | n-Bu | CH₂OCH₃ | CH₃ | CH₃ |
| 464. | n-Bu | n-Bu | OCH₃ | CH₃ | CH₃ |
| 465. | n-Bu | n-Bu | Ph | CH₃ | CH₃ |
| 466. | n-Bu | n-Bu | —CH₂Ph | CH₃ | CH₃ |
| 467. | n-Bu | CH₃ | CH₃ | CF₃ | CH₃ |
| 468. | n-Bu | CH₃ | CH₃ | CF₂CF₃ | CH₃ |
| 469. | n-Bu | CH₃ | CH₃ | CH₂OCH₃ | CH₃ |
| 470. | n-Bu | CH₃ | CH₃ | OCH₃ | CH₃ |
| 471. | n-Bu | CH₃ | CH₃ | Ph | CH₃ |
| 472. | n-Bu | CH₃ | CH₃ | —CH₂Ph | CH₃ |
| 473. | CF₃ | CH₃ | CH₃ | n-Bu | CH₃ |
| 474. | CF₂CF₃ | CH₃ | CH₃ | n-Bu | CH₃ |
| 475. | CH₂OCH₃ | CH₃ | CH₃ | n-Bu | CH₃ |
| 476. | CH₃ | CH₃ | CH₃ | n-Bu | CH₃ |
| 477. | Ph | CH₃ | CH₃ | n-Bu | CH₃ |
| 478. | —CH₂Ph | CH₃ | CH₃ | n-Bu | CH₃ |
| 479. | CF₃ | n-Bu | CH₃ | CH₃ | CH₃ |
| 480. | CF₂CF₃ | n-Bu | CH₃ | CH₃ | CH₃ |
| 481. | CH₂OCH₃ | n-Bu | CH₃ | CH₃ | CH₃ |
| 482. | OCH₃ | n-Bu | CH₃ | CH₃ | CH₃ |
| 483. | Ph | n-Bu | CH₃ | CH₃ | CH₃ |
| 484. | —CH₂Ph | n-Bu | CH₃ | CH₃ | CH₃ |
| 485. | CH₃ | CH₃ | CF₃ | n-Bu | CH₃ |
| 486. | CH₃ | CH₃ | CF₂CF₃ | n-Bu | CH₃ |
| 487. | CH₃ | CH₃ | CH₂OCH₃ | n-Bu | CH₃ |
| 488. | CH₃ | CH₃ | OCH₃ | n-Bu | CH₃ |
| 489. | CH₃ | CH₃ | Ph | n-Bu | CH₃ |
| 490. | CH₃ | CH₃ | —CH₂Ph | n-Bu | CH₃ |
| 491. | CF₃ | n-Bu | H | CH₃ | CH₃ |
| 492. | CF₂CF₃ | n-Bu | H | CH₃ | CH₃ |
| 493. | CH₂OCH₃ | n-Bu | H | CH₃ | CH₃ |
| 494. | OCH₃ | n-Bu | H | CH₃ | CH₃ |
| 495. | Ph | n-Bu | H | CH₃ | CH₃ |
| 496. | —CH₂Ph | n-Bu | H | CH₃ | CH₃ |
| 497. | H | CH₃ | CF₃ | n-Bu | CH₃ |
| 498. | H | CH₃ | CF₂CF₃ | n-Bu | CH₃ |
| 499. | H | CH₃ | CH₂OCH₃ | n-Bu | CH₃ |
| 500. | H | CH₃ | OCH₃ | n-Bu | CH₃ |
| 501. | H | CH₃ | Ph | n-Bu | CH₃ |
| 502. | H | CH₃ | —CH₂Ph | n-Bu | CH₃ |
| 503. | n-Bu | H | CH₃ | CF₃ | CH₃ |
| 504. | n-Bu | H | CH₃ | CF₂CF₃ | CH₃ |
| 505. | n-Bu | H | CH₃ | CH₂OCH₃ | CH₃ |
| 506. | n-Bu | H | CH₃ | OCH₃ | CH₃ |
| 507. | n-Bu | H | CH₃ | Ph | CH₃ |
| 508. | n-Bu | H | CH₃ | —CH₂Ph | CH₃ |
| 509. | CF₃ | CH₃ | n-Bu | H | CH₃ |
| 510. | CF₂CF₃ | CH₃ | n-Bu | H | CH₃ |
| 511. | CH₂OCH₃ | CH₃ | n-Bu | H | CH₃ |
| 512. | OCH₃ | CH₃ | n-Bu | H | CH₃ |
| 513. | Ph | CH₃ | n-Bu | H | CH₃ |
| 514. | —CH₂Ph | CH₃ | n-Bu | H | CH₃ |
| 515. | CF₃ | n-Bu | CH₃ | H | CH₃ |
| 516. | CF₂CF₃ | n-Bu | CH₃ | H | CH₃ |
| 517. | CH₂OCH₃ | n-Bu | CH₃ | H | CH₃ |
| 518. | OCH₃ | n-Bu | CH₃ | H | CH₃ |
| 519. | Ph | n-Bu | CH₃ | H | CH₃ |
| 520. | —CH₂Ph | n-Bu | CH₃ | H | CH₃ |
| 521. | CH₃ | H | CF₃ | n-Bu | CH₃ |
| 522. | CH₃ | H | CF₂CF₃ | n-Bu | CH₃ |
| 523. | CH₃ | H | CH₂OCH₃ | n-Bu | CH₃ |
| 524. | CH₃ | H | OCH₃ | n-Bu | CH₃ |
| 525. | CH₃ | H | Ph | n-Bu | CH₃ |
| 526. | CH₃ | H | —CH₂Ph | n-Bu | CH₃ |
| 527. | n-Bu | CH₃ | H | CF₃ | CH₃ |
| 528. | n-Bu | CH₃ | H | CF₂CF₃ | CH₃ |
| 529. | n-Bu | CH₃ | H | CH₂OCH₃ | CH₃ |
| 530. | n-Bu | CH₃ | H | OCH₃ | CH₃ |
| 531. | n-Bu | CH₃ | H | Ph | CH₃ |
| 532. | n-Bu | CH₃ | H | —CH₂Ph | CH₃ |
| 533. | CF₃ | H | CH₃ | n-Bu | CH₃ |
| 534. | CF₂CF₃ | H | CH₃ | n-Bu | CH₃ |
| 535. | CH₂OCH₃ | H | CH₃ | n-Bu | CH₃ |
| 536. | OCH₃ | H | CH₃ | n-Bu | CH₃ |
| 537. | Ph | H | CH₃ | n-Bu | CH₃ |
| 538. | —CH₂Ph | H | CH₃ | n-Bu | CH₃ |
| 539. | H | —CH₂— | | H | CH₃ |
| 540. | H | —(CH₂)₄— | | H | CH₃ |

For the following example compounds physico-chemical data have been obtained and are displayed in order to illustrate the working of the present invention, including the outlined methods of synthesis. The number of given data may not be interpreted as a limitation of the invention. Analysis of compounds 6.610 to 6.684: Reversed-phase was performed on a Waters Alliance 2790 LC equiped with a Waters996 UV detector using a YMC CombiScreen ODS-AQ cartridge (30×4.6 mm, S-5 □m, 12 um) Mobile phase: A: H₂O/CH₃CN 10/TFA, B: CH₃CN/TFA 0., C: MeOH.Gradient: 89% A 11% B, 0–3.5 min; 90% B 10% C 0.5 min.

TABLE C

| Comp. No. from Table B | Table A | Melting point [° C.] or ¹H-NMR [δ in ppm] |
|---|---|---|
| 1.001 | 028 | 122–131 |
| 1.002 | 028 | 199–201 |
| 1.003 | 028 | (DMSO); 0.60(t, 3H), 1.19(s, 3H), 1.67(q, 2H), 2.02(s, 3H), 6.93(dd, 1H), 7.26(t, 1H), 7.47(d, 1H), 7.76(dd, 1H), 7.83(dd, 1H), 7.93(dd, 1H), 8.48(d, 1H), 8.55(d, 1H), 8.63(d, 1H), 10.00(s, NH); |
| 1.004 | 028 | 187–192 |
| 1.005 | 028 | (CDCl₃); 1.80(s, 3H), 2.14(s, 3H), 7.00(dd, 1H), 7.22–7.29(m, 7H), 7.39(dd, 1H), 7.72(s, 1H), 7.84(s, 1H), 8.52(d, 1H), 8.70(dd, 1H), 8.77(s, NH); |
| 1.006 | 028 | 167–168 |
| 1.007 | 028 | 90–92 |
| 1.008 | 028 | 95–99 |
| 1.009 | 028 | (DMSO); 1.41(s, 3H), 2.18(s, 3H), 3.10(s, 2H), 7.04(d, 1H), 7.14(s, 5H), 7.38(t, 1H), 7.50(d, 1H), 7.85(d, 1H), 7.92(d, 1H), 7.98(s, 1H), 8.42(s, 1H), 8.55(d, 1H), 8.71(d, 1H), 10.09(s, NH); |
| 1.010 | 028 | 165–168 |
| 1.011 | 028 | 215–219 |
| 1.012 | 028 | 210 |
| 1.050 | 028 | 202–205 |
| 1.051 | 028 | 164–167 |
| 1.052 | 028 | 167–170 |
| 1.053 | 028 | 189–192 |
| 2.002 | 028 | 181–185 |
| 2.003 | 028 | 204–208 |
| 2.004 | 028 | 210 |
| 2.005 | 028 | 190–192 |
| 2.006 | 028 | 199–203 |
| 2.007 | 028 | 180–182 |
| 2.008 | 048 | 127–135 |
| 2.009 | 028 | 87–83 |
| 2.010 | 028 | 195–197 |
| 2.011 | 028 | 187–189 |
| 2.012 | 028 | 218–220 |
| 3.001 | 028 | 163–166 |
| 3.002 | 028 | 189–191 |
| 3.003 | 028 | 158 |
| 3.011 | 028 | (DMSO); 3.32(s, 3H), 4.35(s, 2H), 5.66(s, 1H), 7.03(dd, 1H), 7.35(t, 1H), 7.62(m, 1H), 7.77(m, 1H), 8.00(m, 1H), 8.20(m, 1H), 8.48(m, 1H), 8.62(d, 1H), 8.74(d, 1H), 10.12(s, NH), 12.25(s, 1H); |
| 3.012 | 028 | 158–159 |
| 3.013 | 028 | 167 |
| 3.014 | 028 | 141–150 |
| 3.015 | 028 | (DMSO); 1.74(s, 3H), 2.15(s, 3H), 7.01(dd, 1H), 7.37(t, 1H), 7.46(s, 1H), 7.82(s, 1H), 7.93(d, 2H), 8.55(d, 1H), 8.63(d, 1H), 9.21(s, 1H), 10.07(s, NH), 11.5/12.0(s, 1H); |
| 3.016 | 028 | (DMSO); 1.85(s, 3H), 7.02(dd, 1H), 7.35–7.79(m, 7H), 8.61(d, 1H), 8.74(d, 1H), 10.12(s, NH), 11.7/11.9(s, 1H); |
| 3.017 | 028 | 185–188 |
| 3.018 | 028 | 171–174 |
| 3.019 | 028 | 149–150 |
| 3.020 | 028 | 155–157 |
| 3.027 | 028 | 178–180 |
| 3.028 | 028 | 181–184 |
| 3.029 | 028 | 199–201 |
| 3.030 | 028 | 120–125 |
| 3.031 | 028 | 169–170 |
| 3.032 | 028 | 184 |
| 3.033 | 028 | 171–175 |
| 3.034 | 028 | 163–167 |
| 3.035 | 028 | 152–161 |
| 3.036 | 028 | 115–119 |
| 3.037 | 028 | 182–185 |
| 3.038 | 028 | 160–163 |
| 3.039 | 028 | 210 |
| 3.040 | 028 | 184 |
| 3.041 | 028 | 210 |
| 5.001 | 028 | 143–144 |
| 5.002 | 028 | 151–153 |
| 5.003 | 028 | 166–168 |
| 5.004 | 028 | 200–202 |
| 1.001 | 048 | (DMSO); 1.31(s, 6H), 2.14(s, 3H), 3.42(s, 3H), 5.49(s, 2H), 7.37–7.60(m, 5H), 7.88(dd, 1H), 8.54(s, 1H), 8.61(d, 1H), 8.64(d, 1H); |
| 6.002 | 028 | 238–240 |
| 6.003 | 028 | 120–125 |
| 6.012 | 028 | 229–231 |
| 6.015 | 028 | 173–175 |
| 6.020 | 028 | 184–186 |
| 6.152 | 028 | 213–215 |
| 6.153 | 028 | 118–127 |
| 6.177 | 028 | 184–186 |
| 6.179 | 028 | 187–189 |
| 6.605 | 028 | 196–198 |
| 6.606 | 028 | 79–84 |
| 6.607 | 028 | 153–156 |
| 6.608 | 028 | 110–120 |
| 6.609 | 028 | 213–216 |
| 6.610 | 028 | RT 3.3 MS 614.2(Area MS 100%, AreaUV 100%) |
| 6.611 | 028 | RT 3.23 MS 564.2(Area MS 100%, AreaUV 100%) |
| 6.612 | 028 | RT 3.9 MS 622.3(Area MS 100%, AreaUV 100%) |
| 6.613 | 028 | RT 2.37 MS 550(Area MS 100%, AreaUV 100%) |
| 6.614 | 028 | RT 2.37 MS 550(Area MS 100%, AreaUV 100%) |
| 6.615 | 048 | RT 2.15 MS 478.1(Area MS 100%, AreaUV 100%) |
| 6.616 | 028 | RT 2.4 MS 480.1(Area MS 100%, AreaUV 84%) |
| 6.617 | 028 | RT 2.37 MS 480.1(Area MS 100%, AreaUV 100%) |
| 6.618 | 028 | RT 2.1 MS 480.1(Area MS 100%, AreaUV 88%) |
| 6.619 | 028 | RT 2.32 MS 480.1(Area MS 100%, AreaUV 100%) |
| 6.620 | 028 | RT 2.1 MS 555.1(Area MS 100%, AreaUV 90%) |
| 6.621 | 028 | RT 2.1 MS 555.1(Area MS 100%, AreaUV 90%) |
| 6.622 | 028 | RT 2.1 MS 468.1(Area MS 100%, AreaUV 85%) |
| 6.623 | 028 | RT 1.54 MS 572.1(Area MS 100%, AreaUV 89%) |
| 6.624 | 028 | RT 2.5 MS 482.1(Area MS 100%, AreaUV 100%) |
| 6.625 | 028 | RT 2.24 MS 466.1(Area MS 100%, AreaUV 100%) |
| 6.626 | 028 | RT 1.95 MS 466.1(Area MS 100%, AreaUV 100%) |
| 6.627 | 028 | RT 1.85 MS 464.1(Area MS 100%, AreaUV 100%) |
| 6.628 | 028 | RT 2.1 MS 492.1(Area MS 100%, AreaUV 92%) |
| 6.629 | 028 | RT 2 MS 478.1(Area MS 100%, AreaUV 100%) |
| 6.630 | 028 | RT 2 MS 478.1(Area MS 100%, AreaUV 100%) |
| 6.631 | 028 | RT 2.5 MS 494.1(Area MS 100%, AreaUV 93%) |
| 6.632 | 028 | RT 2.1 MS 480.1(Area MS 100%, AreaUV 74%) |
| 6.633 | 028 | RT 2.1 MS 480.1(Area MS 100%, AreaUV 74%) |
| 6.634 | 028 | RT 2.24 MS 494.1(Area MS 100%, AreaUV 100%) |
| 6.635 | 028 | RT 2.24 MS 494.1(Area MS 100%, AreaUV 100%) |
| 6.636 | 028 | RT 3.1; 3.2 MS 580.1(Area MS 70%, AreaUV 62%) |
| 6.637 | 028 | RT 4 MS 598(Area MS 77%, AreaUV 100%) |

TABLE C-continued

| Comp. No. from Table B | Table A | Melting point [° C.] or ¹H-NMR [δ in ppm] |
|---|---|---|
| 6.638 | 028 | RT 3.47 |
| | | MS 610.1(Area MS 58%, AreaUV 100%) |
| 6.639 | 028 | RT 3.5 |
| | | MS 564.1(Area MS 67%, AreaUV 100%) |
| 6.640 | 028 | RT 3.4 |
| | | MS 598.1(Area MS 79%, AreaUV 80%) |
| 6.641 | 028 | RT 3.22 |
| | | MS 560.1(Area MS 69%, AreaUV 100%) |
| 6.642 | 028 | RT 3.07 |
| | | MS 660.1(Area MS 100%, AreaUV 100%) |
| 6.643 | 028 | RT 3.1 |
| | | MS 514(Area MS 59%, AreaUV 100%) |
| 6.644 | 028 | RT 2.8 |
| | | MS 522.1(Area MS 72%, AreaUV 100%) |
| 6.645 | 028 | RT 3.07 |
| | | MS 548.1(Area MS 80%, AreaUV 100%) |
| 6.646 | 028 | RT 4.4 |
| | | MS 638.2(Area MS 90%, AreaUV 62%) |
| 6.647 | 028 | RT 3.5 |
| | | MS 580.1(Area MS 57%, AreaUV 100%) |
| 6.648 | 028 | RT 2.81; 2.8 |
| | | MS 500.1(Area MS 63%, AreaUV 100%) |
| 6.649 | 028 | RT 4 |
| | | MS 538.2(Area MS 84%, AreaUV 100%) |
| 6.650 | 028 | RT 3.11 |
| | | MS 546.1(Area MS 53%, AreaUV 80%) |
| 6.651 | 028 | RT 2.7; 2.8 |
| | | MS 540.1(Area MS 56%, AreaUV 74%) |
| 6.652 | 028 | RT 4.5 |
| | | MS 592.2(Area MS 62%, AreaUV 100%) |
| 6.653 | 028 | RT 3.5 |
| | | MS 554.2(Area MS 96%, AreaUV 100%) |
| 6.654 | 028 | RT 4.3 |
| | | MS 562.2(Area MS 71%, AreaUV 100%) |
| 6.655 | 028 | RT 3.47 |
| | | MS 494.1(Area MS 100%, AreaUV 100%) |
| 6.656 | 028 | RT 3 |
| | | MS 514.1(Area MS 86%, AreaUV 100%) |
| 6.657 | 028 | RT 2.2 |
| | | MS 551.1(Area MS 74%, AreaUV 100%) |
| 6.658 | 028 | RT 3.36 |
| | | MS 508.1(Area MS 100%, AreaUV 100%) |
| 6.659 | 028 | RT 3.22 |
| | | MS 590.1(Area MS 84%, AreaUV 100%) |
| 6.660 | 028 | RT 3.3 |
| | | MS 564.1(Area MS 69%, AreaUV 74%) |
| 6.661 | 028 | RT 3.8 |
| | | MS 758(Area MS 42%, AreaUV 100%) |
| 6.662 | 028 | RT 3.4 |
| | | MS 566.1(Area MS 78%, AreaUV 100%) |
| 6.663 | 028 | RT 3.4 |
| | | MS 642(Area MS 80%, AreaUV 100%) |
| 6.664 | 028 | RT 3 |
| | | MS 614.2(Area MS 82%, AreaUV 100%) |
| 6.665 | 028 | RT 2.4 |
| | | MS 512.1(Area MS 92%, AreaUV 82%) |
| 6.666 | 028 | RT 2.0; 2.3 |
| | | MS 545.1(Area MS 82%, AreaUV 100%) |
| 6.667 | 028 | RT 3.2 |
| | | MS 494.1(Area MS 74%, AreaUV 100%) |
| 6.668 | 028 | RT 3.4 |
| | | MS 596.1(Area MS 75%, AreaUV 100%) |
| 6.669 | 028 | RT 4.4 |
| | | MS 658.1(Area MS 66%, AreaUV 100%) |
| 6.670 | 028 | RT 3.3 |
| | | MS 562.1(Area MS 81%, AreaUV 100%) |
| 6.671 | 028 | RT 3.1 |
| | | MS 585(Area MS 70%, AreaUV 100%) |
| 6.672 | 028 | RT 2.04; 2.1 |
| | | MS 531.1(Area MS 84%, AreaUV 100%) |
| 6.673 | 028 | RT 3.9 |
| | | MS 586.2(Area MS 88%, AreaUV 100%) |
| 6.674 | 028 | RT 3 |
| | | MS 522(Area MS 91%, AreaUV 100%) |
| 6.675 | 028 | RT 4.3 |
| | | MS 578.2(Area MS 88%, AreaUV 100%) |
| 6.676 | 028 | RT 2.78; 2.8 |
| | | MS 512.1(Area MS 100%, AreaUV 100%) |
| 6.677 | 028 | RT 2.7 |
| | | MS 525.1(Area MS 95%, AreaUV 100%) |
| 6.678 | 028 | RT 3.3 |
| | | MS 584.1(Area MS 91%, AreaUV 100%) |
| 6.679 | 028 | RT 1.8; 2.1 |
| | | MS 517.1(Area MS 72%, AreaUV 100%) |
| 6.680 | 028 | RT 3.7 |
| | | MS 512.1(Area MS 96%, AreaUV 100%) |
| 6.681 | 028 | RT 3 |
| | | MS 516.1(Area MS 54%, AreaUV 38%) |
| 6.682 | 028 | RT 3.5 |
| | | MS 708(Area MS 71%, AreaUV 100%) |
| 6.683 | 028 | RT 3.7 |
| | | MS 720.1(Area MS 81%, AreaUV 100%) |
| 6.684 | 028 | RT 3.1 |
| | | MS 607.1(Area MS 88%, AreaUV 100%) |
| 6.685 | 028 | 80–100 |
| 6.686 | 028 | 183–186 |
| 6.687 | 028 | 212–215 |
| 6.688 | 028 | 176–178 |
| 6.689 | 028 | 183–185 |
| 6.690 | 028 | 110–115 |
| 6.691 | 028 | 119–123 |
| 6.692 | 028 | 117–120 |
| 6.693 | 028 | 83–89 |
| 6.694 | 028 | 90–100 |
| 6.695 | 028 | 73–76 |
| 6.696 | 028 | 110–120 |
| 6.697 | 028 | 145–160 |
| 6.698 | 028 | 84–90 |
| 6.699 | 028 | 239–242 |
| 6.700 | 028 | 90–105 |
| 6.701 | 028 | 232–235 |
| 6.702 | 028 | 178–182 |
| 6.703 | 028 | 142–148 |
| 6.704 | 028 | 222–225 |
| 6.705 | 028 | 75–85 |
| 6.706 | 028 | 142–144 |
| 6.707 | 028 | 235–240 |
| 6.708 | 028 | 141–144 |
| 6.709 | 028 | 80–82 |
| 6.710 | 028 | 82–84 |
| 6.711 | 028 | 174–176 |
| 6.712 | 028 | 201–203 |
| 6.713 | 028 | 120–125 |
| 6.714 | 028 | 198–200 |
| | | RT 2.06 |
| | | MS 464.1(Area MS 100%, AreaUV 100%) |
| 6.715 | 028 | 85–90 |
| 6.716 | 028 | 87–97 |
| 6.717 | 028 | 251–253 |
| 6.718 | 028 | RT 2.41 |
| | | MS 512.1(Area MS 100%, AreaUV 0%) |
| 6.719 | 028 | RT 2.63 |
| | | MS 510.1(Area MS 88%, AreaUV 100%) |
| 6.720 | 028 | RT 2.4 |
| | | MS 482.1(Area MS 90%, AreaUV 82%) |
| 6.721 | 028 | 92–96 |
| 6.722 | 028 | 90–100 |
| 6.723 | 028 | 110–115 |
| 6.724 | 028 | 188–190 |
| 6.725 | 028 | 70–80 |
| 6.726 | 028 | 182–184 |
| 7.001 | 028 | 110–130 |
| 7.270 | 028 | 189–192 |
| 7.271 | 028 | 207–209 |
| 7.277 | 028 | 89–93 |
| 7.303 | 028 | 177–179 |
| 7.808 | 028 | 165–167 |
| 7.830 | 028 | 90–95 |
| 8.270 | 028 | 201–204 |

TABLE C-continued

| Comp. No. from Table B | Table A | Melting point [° C.] or ¹H-NMR [δ in ppm] |
|---|---|---|
| 8.271 | 028 | 193–195 |
| 8.277 | 028 | 105–115 |
| 8.279 | 028 | 95–100 |
| 8.285 | 028 | 98–105 |
| 8.303 | 028 | 105–110 |
| 8.539 | 028 | 80–85 |
| 8.540 | 028 | 95–100 |

In the following, examples of test systems in plant protection are provided which can demonstrate the efficiency of the compounds of the formula I (designated as "active ingredient" or "test compounds"):

BIOLOGICAL EXAMPLES

Example B-1

Effect Against *Puccinia graminis* on Wheat
(Brownrust on Wheat)

a) Residual Protective Activity 1 week old wheat plants cv. Arina are treated with the formulated test-compound (0.02% active substance) in a spray chamber. Two days after application wheat plants are inoculated by spraying a spore suspension ($1 \times 10^5$ ureidospores/ml) on the test plants. After an incubation period of 1 day at +20° C. and 95% relative atmospheric humidity (r. h.) plants are kept for 9 days at +20° C. and 60% r.h. in a greenhouse. The disease incidence is assessed 10 days after inoculation.

At the indicated concentration compounds 1.01/028; 2.02/028; 1.03/028; 1.07/028; 2.03/028; 2.05/028; 2.06/028 exhibited over 70% control of the fungal infection in this test.

Example B-2

Effect Against *Phytophthora infestans* on Tomatoes
(Late Blight on Potato)

a) Residual Protective Activity 3 week old tomato plants cv. Roter Gnom are treated with the formulated test compound (0.02% active substance) in a spray chamber. Two day after application the plants are inoculated by spraying a sporangia suspension ($2 \times 10^4$ sporangia/ml) on the test plants. After an incubation period of 4 days at +18° C. and 95% r. h. in a growth chamber the disease incidence is assessed.

At the indicated concentration compounds 1.01/028; 1.03/028; 1.04/028; 1.07/028 exhibited over 70% control of the fungal infection in this test.

Example B-3

Effect Against *Phytophthora infestans*/Potato (Late Blight on Potato)

5 week old potato plants cv. Bintje are treated with the formulated test compound (0.02% active substance) in a spray chamber. Two days after application the plants are inoculated by spraying a sporangia suspension ($1.4 \times 10^5$ sporangia/ml) on the test plants. After an incubation period of 4 days at +18° C. and 95% r. h. in a growth chamber the disease incidence is assessed.

Example B-4

Effect Against *Plasmopara viticola* on Grapevine
(Grape Downy Mildew)

5 week old grape seedlings cv. Gutedel are treated with the formulated test compound (0.02% active substance) in a spray chamber. One day after application grape plants are inoculated by spraying a sporangia suspension ($4 \times 10^4$ sporangia/ml) on the lower leaf side of the test plants. After an incubation period of 6 days at +22° C. and 95% r. h. in a greenhouse the disease incidence is assessed.

At the indicated concentration compounds 1.01/028;3.01/028; 1.04/028 exhibited over 70% control of the fungal infection in this test.

Example B-5

Residual Protective Activity Against *Venturia inaegualis* on Apples (Scab on Apple)

4 week old apple seedlings cv. McIntosh are treated with the formulated test compound (0.02% active substance) in a spray chamber. One day after application apple plants are inoculated by spraying a spore suspension ($4 \times 10^5$ conidia/ml) on the test plants. After an incubation period of 4 days at +20° C. and 95% r. h. the plants are transferred to standard greenhouse conditions at 20 and 60% r.h. where they stayed for 2 days. After another 4 day incubation period at +20° C. and 95% r. h. the disease incidence is assessed. At the indicated concentration compounds 2.03/028; 1.001/028 exhibited over 70% control of the fungal infection in this test.

Example B-6

Effect Against *Erysiphe graminis* on Barley
(Powdery Mildew on Barley)

a) Residual Protective Activity

Barley plants, cv. Regina of approximately 8 cm height were treated with the formulated test compound (0.02% active substance) in a spray chamber and duste 2 days after inoculation with conidia of the fungus. The infected plants are placed in a greenhouse at +20° C. 6 days after infection, the fungal attack was evaluated.

At the indicated concentration compounds 1.01/028; 1.03/028; 1.04/028, 2.05/028; 2.09/028; 3.014/028; 3.030/028 exhibited over 70% control of the fungal infection in this test.

Example B-7

*Botrytis cinerea*/Grape (*Botrytis* on Grapes)

5 week old grape seedlings cv. Gutedel are treated with the formulated test compound (0.02% active substance) in a spray chamber. Two days after application grape plants are inoculated by spraying a spore suspension ($1.5 \times 10^5$ conidia/ml) on the test plants. After an incubation period of 3 days at +21° C. and 95% r. h. in a greenhouse the disease incidence is assessed.

At the indicated concentration compounds 1.01/028; 1.03/028; 1.04/028, 1.05/028; 1.06/028, 1.07/028;2.03/028; 2.05/028; 2.08/048; 2.09/028; 3.012/028; 3.013/028;3.014/028; 2.012/028 exhibited over 70% control of the fungal infection in this test.

Example B-8

Effect Against *Botrytis cinerea*/Tomato (*Botrytis* on Tomatoes)

4 week old tomato plants cv. Roter Gnom are treated with the formulated test compound 0.02% active substance) in a spray chamber. Two days after application tomato plants are inoculated by spraying a spore suspension ($1 \times 10^5$ conidia/ml) on the test plants. After an incubation period of 4 days at +20° C. and 95% r. h. in a greenhouse the disease incidence is assessed.

At the indicated concentration compounds 1.01/028; 2.02/028; 3.01/028; 1.04/028; 1.06/028; 2.06/028; 2.05/028; 2.08/048; 4.02/028; 7.270/028 exhibited over 70% control of the fungal infection in this test.

Example B-9

Effect Against *Pyricularia oryzae*/Rice (Rice Blast)

3 week old rice plants cv. Sasanishiki are treated with the formulated test compound (0.02% active substance) in a spray chamber. Two days after application rice plants are inoculated by spraying a spore suspension ($1 \times 10^5$ conidia/ml) on the test plants. After an incubation period of 6 days at +25° C. and 95% r. h. the disease incidence is assessed. At the indicated concentration compounds 1.02/028; 1.04/028; 2.03/028; 2.06/028; 2.07/028 exhibited over 70% control of the fungal infection in this test.

Example B-10

Effect Against *Pyrenophora teres* (Helminthosorium)/Barley (Net Blotch on Barley)

1 week old barley plants cv. Regina are treated with a formulated test compound (0.02% active substance) in a spray chamber. Two days. after application barley plants are inoculated by spraying a spore suspension ($3 \times 10^4$ conidia/ml) on the test plants. After an incubation period of 2 days at +20° C. and 95% r.h. the disease incidence is assessed.

At the indicated concentration compounds 1.01/028; 2.02/028; 3.01/028; 5.01/028; 1.03/028; 1.04/028, 1.01/048; 1.06/028, 1.07/028; 1.08/028; 2.03/028; 2.05/028; 2.07/028; 2.08/048; 2.09/028; 3.012/028; 3.013/028; 3.014/028; 2.012/028; 2.011/028; 3.016/028; 3.017/0283.027/028; 3.028/028; 7.270/028 exhibited over 70% control of the fungal infection in this test.

Example B-11

Effect Against *Fusarium culmorum*/Wheat (*Fusarium* Head Blight on Wheat)

A conidia suspension of *F. culmorum* ($7 \times 10^5$ conidia/ml) is mixed with the formulated test compound (0.002% active substance). The mixture is applied into a pouch which has been equipped before with a filter paper. After the application wheat seeds (cv. Orestis) are sown into the upper fault of the filter paper. The prepared pouches are then incubated for 11 days at approx. +10° C. to +18° C. and a relative humidity of 100% with a light period of 14 hours. The evaluation is made by assessing the degree of disease occurrence in the form of brown lesions on the roots.

Example B-12

Effect Against *Septoria nodorum*/Wheat (*Septoria* Leaf Spot on Wheat)

1 week old wheat plants cv. Arina are treated with a formulated test compound (0.02% active substance) in a spray chamber. One day after application wheat plants are inoculated by spraying a spore suspension ($6 \times 10^5$ conidia/ml) on the test plants. After an incubation period of 1 day at +22° C. and 95% r.h. plants are kept for 7 days at +22° C. and 60% r.h. in a greenhouse. The disease incidence is assessed 8 days after inoculation.

At the indicated concentration compounds 1.01/028; 2.02/028; 3.01/028; 5.01/028; 1.03/028; 1.06/028, 1.07/028; 2.03/028; 2.04/028; 2.05/028; 2.06/028; 2.09/028; 3.012/028; 2.012/028; 3.028/028 exhibited over 70% control of the fungal infection in this test.

The invention claimed is:
1. A compound of formula I

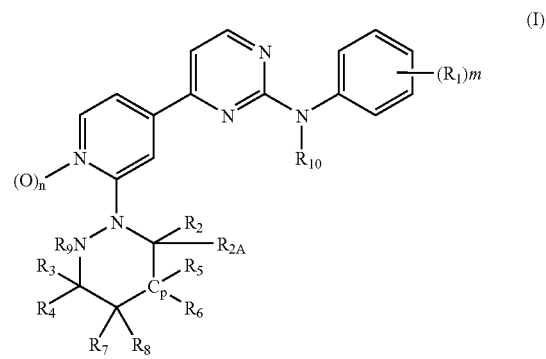

wherein
m is 0, 1, 2 or 3;
n and p are independently of each other 0 or 1;
$R_1$ is halogen, optionally substituted alkyl, optionally substituted alkoxy, optionally substituted alkenyloxy, optionally substituted alkynyloxy, optionally substituted thioalkyl optionally substituted aryl, $COOR_{11}$, $CONR_{12}R_{13}$, $S(O)_qR_{14}$, $SO_2NR_{15}R_{16}$ or $NR_{15a}R_{16a}$; when there is more than on $R_1$ group, they may be the same or different;
q is 1 or 2;
$R_2$, $R_{2a}$, $R_3$, $R_4$, $R_5$, $R_6$, $R_7$, $R_8$ are each independently hydrogen, optionally substituted alkyl, $COR_{17}$, $COOR_{18}$ or optionally substituted aryl, and in addition $R_2$ and $R_3$ may also independently be optionally substituted alkoxy, optionally substituted alkenyloxy, optionally substituted alkynyloxy, or optionally substituted alkylthio, $COOR_{19}$, $CONR_{20}R_{21}$, OH or SH;
$R_6$ and $R_7$ may also be independently halogen, optionally substituted alkoxy, optionally substituted alkenyloxy, optionally substituted alkynyloxy, optionally substituted alkenylamino, optionally substituted alkynylamino, optionally substituted alkylthio, optionally substituted cycloalkyl, optionally substituted heteroaryl, optionally substituted hetrocyclyl, optionally substituted cycloalkyloxy, OH, SH, $N_3$, $NR_{22}R_{23}$ or $N(R_{24})COR_{25}$;

or the ring members $CR_3R_4$ or $CR_2R_{2A}$ are independently of each other a carbonyl group (C=O) or a thonyl group (C=S);

or one or two of the adjacent pairs of groups $R_9$ and $R_4$, $R_4$ and $R_8$, $R_5$ and $R_8$, or, if p is zero, $R_{2A}$ and $R_8$ may form a bond, provided that if there are 2 double bonds in the ring the double bonds are not adjacent each other;

or the pair of groups $R_7$ and $R_8$ or the pair of groups $R_6$ and $R_7$ together with the atom to which they are attached form a $C_3$–$C_7$ saturated ring;

$R_9$ is hydrogen, optionally substituted alkyl, optionally substituted alkenyl or optionally substituted alkynyl;

$R_{10}$ is hydrogen, $C_1$–$C_4$-alkyl, $C_3$–$C_4$-alkenyl, $C_3$–$C_4$-alkynyl, —$CH_2OR_{26}$, $CH_2SR_{27}$, —$C(O)R_{28}$, —$C(O)OR_{29}$, $SO_2R_{30}$, $SOR_{31}$ or $SR_{32}$;

$R_{26}$, $R_{27}$, $R_{28}$, $R_{29}$, $R_{30}$, $R_{31}$, $R_{32}$ are independently $C_1$–$C_8$-alkyl $C_1$–$C_8$-alkoxyalkyl, $C_1$–$C_8$ haloalkyl or phenyl$C_1$–$C_2$-alkyl wherein the phenyl may be substituted by up to three groups selected from halo or $C_1$–$C_4$-alkyl, $R_{11}$, $R_{12}$, $R_{13}$, $R_{14}$, $R_{15}$, $R_{16}R_{15a}$, $R_{16a}$, $R_{17}$, $R_{18}$, $R_{19}$, $R_{20}$, $R_{21}$, $R_{22}$, $R_{23}$, $R_{24}$, and $R_{25}$ are independently H or optionally substituted alkyl; or a salt thereof.

2. A compound according to claim 1, wherein the moiety

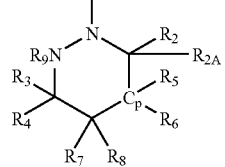

is a 5- and 6-membered ring selected from 2,4-dihydro-pyrazol-3-ones, 2,4-dihydro-pyrazole-3-thione, 1H-pyrazoles, 2H-pyridazin-3-ones, 4,5-dihydro-2H-pyridazin-3-ones, 1,2-dihydro-pyrazol-3-ones, 1,2-dihydro-pyrazole-3-thione, pyrazolidin-3-one, pyrazolidine-3-thione, 2H-pyridazin-3-thione and 4,5-dihydro-2H-pyridazin-3-thione.

3. A compound according to claim 1, wherein $R_1$ is halogen, $C_{1-3}$ haloalkoxy, CH(OH)R, COR, $SO_2NRR'$, CH(NR'R")R, COORa or CONRbRc where Ra, Rb, Rc, R, R', R" are independently H or lower alkyl.

4. A compound according to claim 1, wherein $R_2$, $R_{2A}$, $R_3$, $R_4$, $R_5$, $R_6$, $R_7$, $R_8$ and $R_9$ independently of each other are hydrogen or methyl.

5. A compound according to claim 1, wherein n is zero.

6. A compound according to claim 1, wherein m is 1 and the $R_1$ group is at the 3- or 4-position of the phenyl ring.

7. A compound according to claim 1, wherein $R_7$ is hydrogen, methyl, ethyl, allyl, propargyl, methoxymethyl, thiomethoxymethyl or ethoxymethyl, more preferably hydrogen or methoxymethyl.

8. A compound according to claim 1, where $R_{10}$ is hydrogen, methyl, ethyl, allyl, propargyl, methoxymethyl, thiomethoxymethyl or ethoxymethyl, preferably hydrogen or methoxymethyl.

9. A compound according to claim 1, wherein the compound is selected from (3-Chloro-phenyl)-{4-[2-(3,4,5-trimethyl-pyrazol-1-yl)-pyridin-4-yl]-pyrimidin-2-yl}-amine;

(3-Chloro-phenyl)-{4-[2-(5-methoxy-3-methoxymethyl-pyrazol-1-yl)-pyridin-4-yl]-pyrimidin-2-yl}-amine;

(3-Chloro-phenyl)-{4-[2-(5-methoxy-3-methoxymethyl-4-methyl-pyrazol-1-yl)-pyridin-4-yl]-pyrimidin-2-yl}-amine;

(3-Chloro-phenyl)-{4-[2-(5-methoxy-4-methyl-pyrazol-1-yl)-pyridin-4-yl]-pyrimidin-2}-amine;

(3-Chloro-phenyl)-{4-[2-(5-ethoxy-3,4-dimethyl-pyrazol-1-yl)-pyridin-4-yl]-pyrimidin-2}-amine;

2-{4-[2-(3-Chloro-phenylamino)-pyrimidin-4-yl]-pyridin-2-yl}-5-methoxymethyl-1,4-dimethyl-1,2-dihydro-pyrazol-3-one;

2-(4-{2-[(3-Chloro-phenyl)-methoxymethyl-amino]-pyrimidin-4-yl}-pyridin-2-yl)-1,5-dimetthyl-1,2-dihydro-pyrazol-3-one;

2-{4-[2-(3-Chloro-phenylamino)-pyrimidin-4-yl]-pyridin-2-yl}-1-ethyl-4,5-dimethyl-1,2-dihydro-pyrazol-3-one;

2-{4-[2-(3-Chloro-phenylamino)-pyrimidin-4-yl]-pyridin-2-yl}-1,4-dimethyl-1,2-dihydro-pyrazol-3-one;

2-{4-[2-(3-Chloro-phenylamino)-pyrimidin-4-yl]-pyridin-2-yl}-1,5-dimethyl-1,2-dihydro-pyrazol-3-one;

2-{4-[2-(3-Chloro-phenylamino)-pyrimidin-4-yl]-pyridin-2-yl}-5-methoxymethyl-4,4-dimethyl-2,4-dihydro-pyrazol-3-one;

2-{4-[2-(3-Chloro-phenylamino)-pyrimidin-4-yl]-pyridin-2-yl}-4,4-dimethyl-2,4-dihydro-pyrazol-3-one;

2-{4-[2-(3-Chloro-phenylamino)-pyrimidin-4-yl]-pyridin-2-yl}-4,4,5-trimethyl-2,4-dihydro-pyrazol-3-thione;

5-{4-[2-(3-Chloro-phenylamino)-pyrimidin-4-yl]-pyridin-2-yl}-7-methyl-5,6-diaza-spiro[2.4]hept-6en-4-one;

2-{4-[2-(3-Chloro-phenylamino)-pyrimidin-4-yl]-pyridin-2-yl}-4-ethyl-4,5-dimethyl-2,4-dihydro-pyrazol-3-one;

(3-Chloro-phenyl)-{4-[2-(5-methoxy-3-methyl-pyrazol-1-yl)-pyridin-4-yl]-pyrimidin-2-yl}-amine;

2-{4-[2-(3-Chloro-phenylamino)-pyrimidin-4-yl]-pyridin-2-yl}-1,4,5-trimethyl-1,2-dihydro-pyrazol-3-one;

2-{4-[2-(3-Chloro-phenylamino)-pyrimidin-4-yl]-pyridin-2-yl}-4,4,5-trimethyl-2,4-dihydro-pyrazol-3-one;

2-{4-[2-(3-Chloro-phenylamino)-pyrimidin-4-yl]-pyridin-2-yl}-1,5-dimethyl-1,2-dihydro-pyrazol-3-one;

4,5-Dichloro-2-{4-[2-(3-chloro-phenylamino)-pyrimidin-4-yl]-pyridin-2-yl}-2H-pyridazin-3-one;

2-{4-[2-(3-Chloro-phenylamino)-pyrimidin-4-yl]-pyridin-2-yl}-6-methyl-2H-pyridazin-3-one;

2-{4-[2-(3-Chloro-phenylamino)-pyrimidin-4-yl]-pyridin-2-yl}-6-methyl-4,5-dihydro-2H-pyridazin-3-one;

2-{4-[2-(3-Chloro-phenylamino)-pyrimidin-4-yl]-pyridin-2-yl}-6-Phenyl-4,5-dihydro-2H-pyridazin-3-one;

4-Chloro-2-{4-[2-(3-chloro-phenylamino)-pyrimidin-4-yl]-pyridin-2-yl}-5-ethoxy-2H-pyridazin-3-one;

4-Chloro-2-{4-[2-(3-chloro-phenylamino)-pyrimidin-4-yl]-pyridin-2-yl}-5-ethylsulfanyl-2H-pyridazin-3-one;

5-Azido-4-chloro-2-{4-[2-(3-chloro-phenylamino)-pyrimidin-4-yl]-pyridin-2-yl}-2H-pyridazin-3-one;

1-{4-[2-(3-Chloro-phenylamino)-pyrimidin-4-yl]-pyridin-2-yl}-2-methyl-pyrazolidin-3-one;

(3-Chloro-phenyl)-{4-[2-(5-methoxy-3,4-dimethyl-pyrazol-1-yl)-pyridin-4-yl]-pyrimidin-2-yl}-amine;

2-{4-[2-(3-Chloro-phenylamino)-pyrimidin-4-yl]-pyridin-2-yl}-5-methoxymethyl-1-methyl-1,2-dihydro-pyrazol-3-one;

2-{4-[2-(3-Chloro-phenylamino)-pyrimidin-4-yl]-pyridin-2-yl}-1,5-dimethyl-3-oxo-2,3-dihydro-1H-pyrazole-4-carbaldehyde;

5-Chloro-2-{4-[2-(3-chloro-phenylamino)-pyrimidin-4-yl]-pyridin-2-yl}-4-(oxetan-3-yloxy)-2H-pyridazin-3-one; and 4-Chloro-2-{4-[2-(3-chloro-phenylamino)-pyrimidin-4-yl]-pyridin-2-yl}-5-(tetrahydro-furan-2-ylmethoxy)-2H-pyridazin-3-one.

10. A composition for controlling and protecting against phytopathogenic microorganisms, comprising a compound of formula I according to claim 1 as active ingredient together with a suitable carrier.

11. A method of controlling and preventing an infestation of crop plants by phytopathogenic microorganisms, which comprises the application of a compound of formula I according to claim 1 as active ingredient to the plant, to parts of plants or to the locus thereof.

12. A method according to claim 11, wherein the phytopathogenic microorganisms are fungal organisms.

* * * * *